US005524130A

United States Patent [19]
Ohhashi

[11] Patent Number: 5,524,130
[45] Date of Patent: Jun. 4, 1996

[54] COMPUTED TOMOGRAPHY APPARATUS

[75] Inventor: Akinami Ohhashi, Saitama-ken, Japan

[73] Assignee: Kabushiki Kaisha Toshiba, Kawasaki, Japan

[21] Appl. No.: 112,473

[22] Filed: Aug. 27, 1993

[30] Foreign Application Priority Data

| Aug. 28, 1992 | [JP] | Japan | 4-229873 |
| Aug. 28, 1992 | [JP] | Japan | 4-229874 |
| Jun. 14, 1993 | [JP] | Japan | 5-141791 |
| Jun. 14, 1993 | [JP] | Japan | 5-141938 |

[51] Int. Cl.$^6$ .................................................. A61B 6/03
[52] U.S. Cl. ...................... 378/15; 378/907; 364/413.18
[58] Field of Search .................. 364/413.16, 413.18, 364/413.23, 413; 378/10, 15, 901

[56] References Cited

U.S. PATENT DOCUMENTS

| 4,495,645 | 1/1985 | Ohhashi | 382/6 |
| 5,046,003 | 9/1991 | Crawford | 364/413.15 |
| 5,208,746 | 5/1993 | King et al. | 364/413.16 |
| 5,216,601 | 6/1993 | Crawford et al. | 364/413.16 |
| 5,233,518 | 8/1993 | King et al. | 364/413.18 |
| 5,315,665 | 5/1994 | Ohhashi | 382/6 |

FOREIGN PATENT DOCUMENTS

| 3-186249 | 8/1991 | Japan. |
| 3-186250 | 8/1991 | Japan. |
| 3-188832 | 8/1991 | Japan. |

*Primary Examiner*—David P. Porta
*Assistant Examiner*—David Vernon Bruce
*Attorney, Agent, or Firm*—Finnegan, Henderson, Farabow, Garrett & Dunner

[57] ABSTRACT

A tomographic image at a given slice position is normally reconstructed by executing convolution and back projection calculations of virtual view data obtained by interpolating projection data in a range of 360°+a double fan angle before and after the slice position, and their reflection beam data. A tomographic image at a slice position adjacent to the given position is calculated in such a manner that the convolution and back projection calculations of the difference between data used in reconstruction of the tomographic image at the first slice position, and data necessary for normally reconstructing a tomographic image to be reconstructed at a current slice position are executed, and the calculation result is added to the already reconstructed tomographic image.

19 Claims, 31 Drawing Sheets

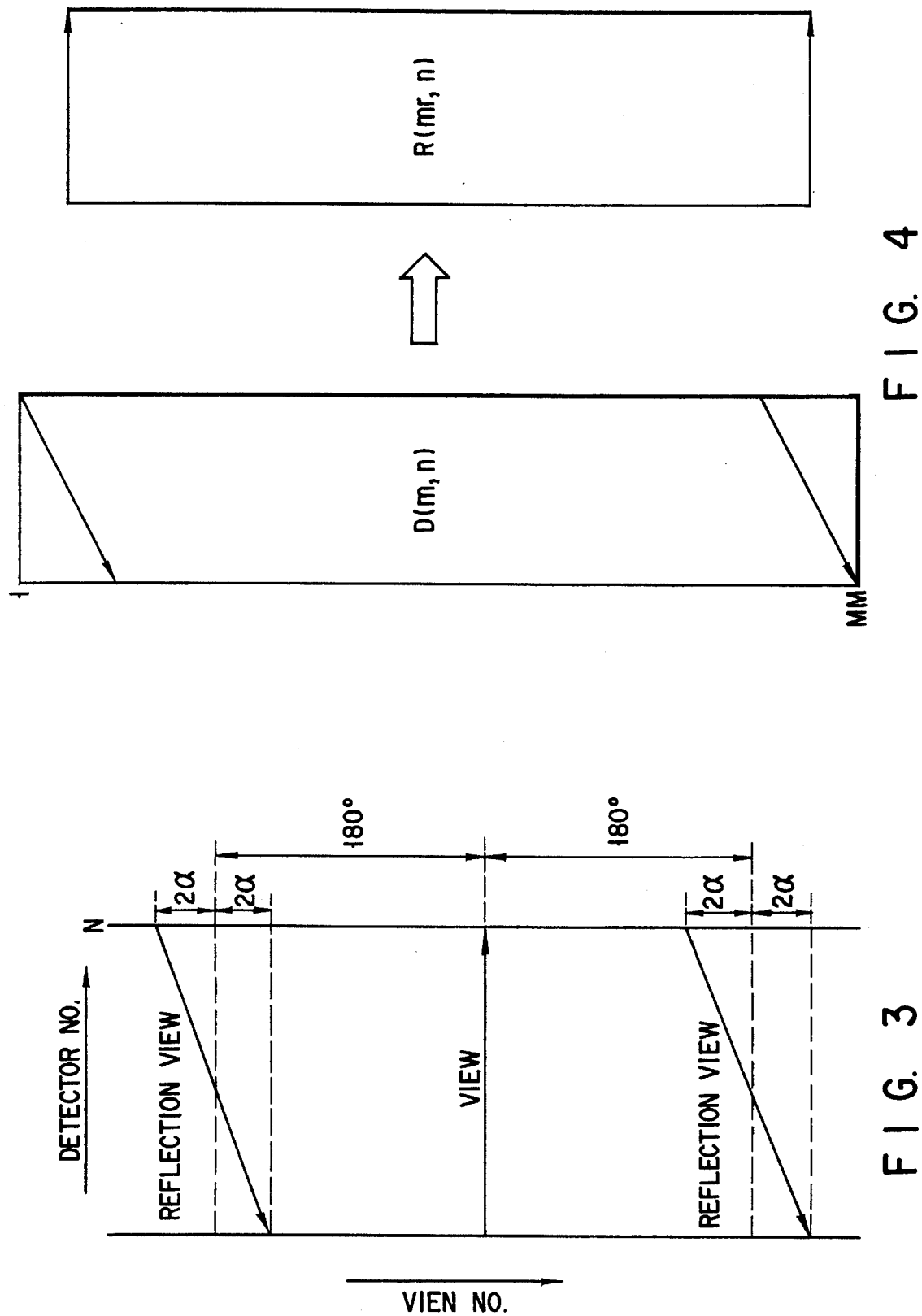

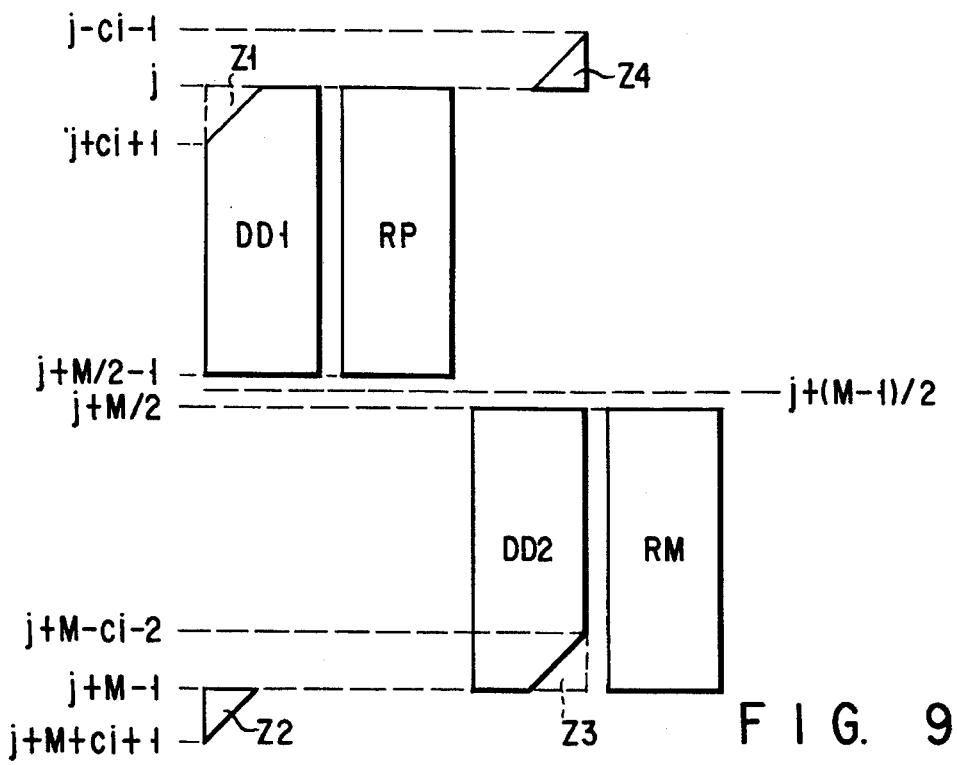
F I G. 9
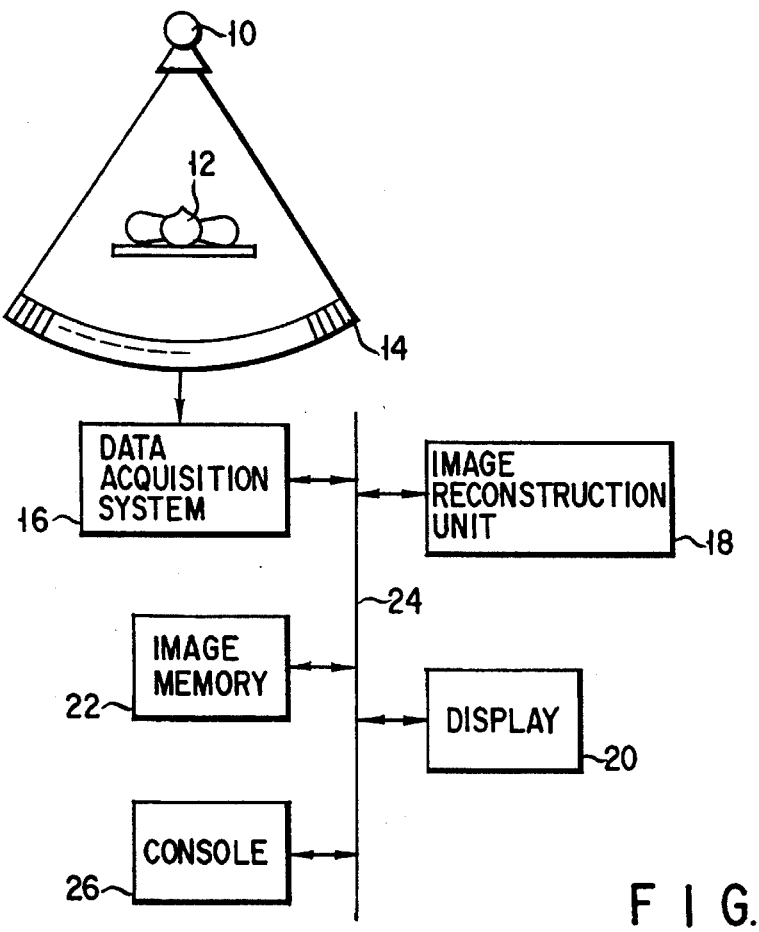
F I G. 10

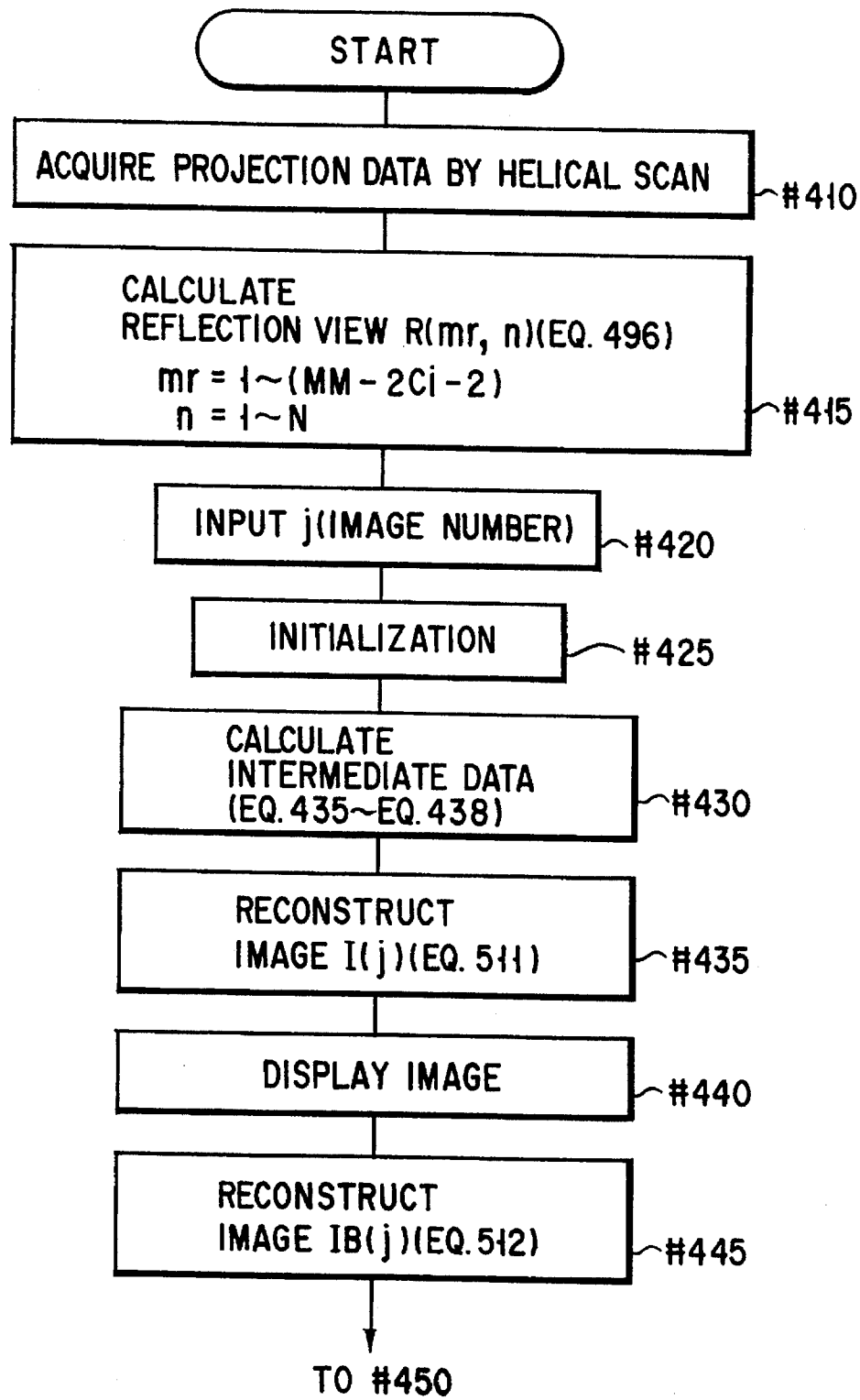
F I G. 17

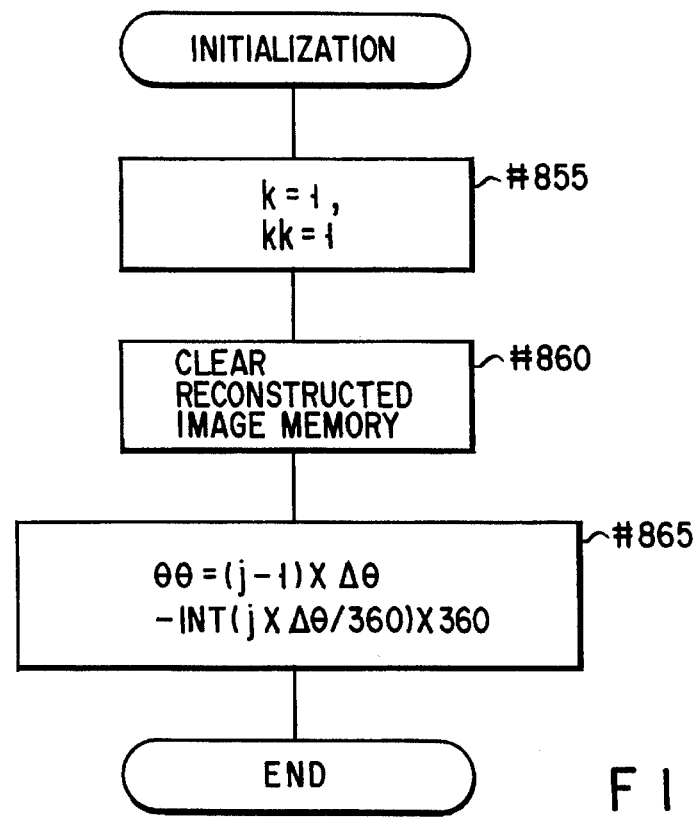
F I G. 24
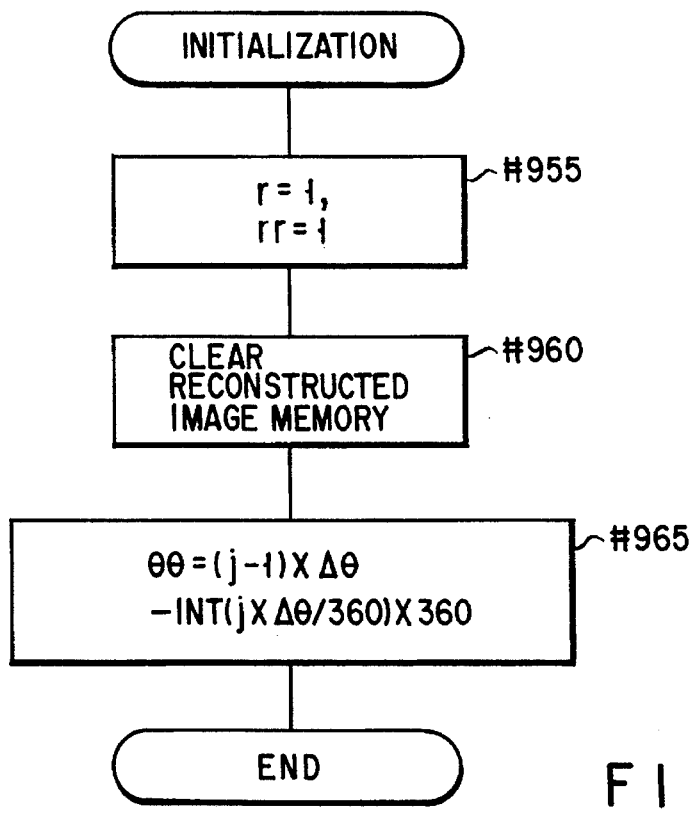
F I G. 27

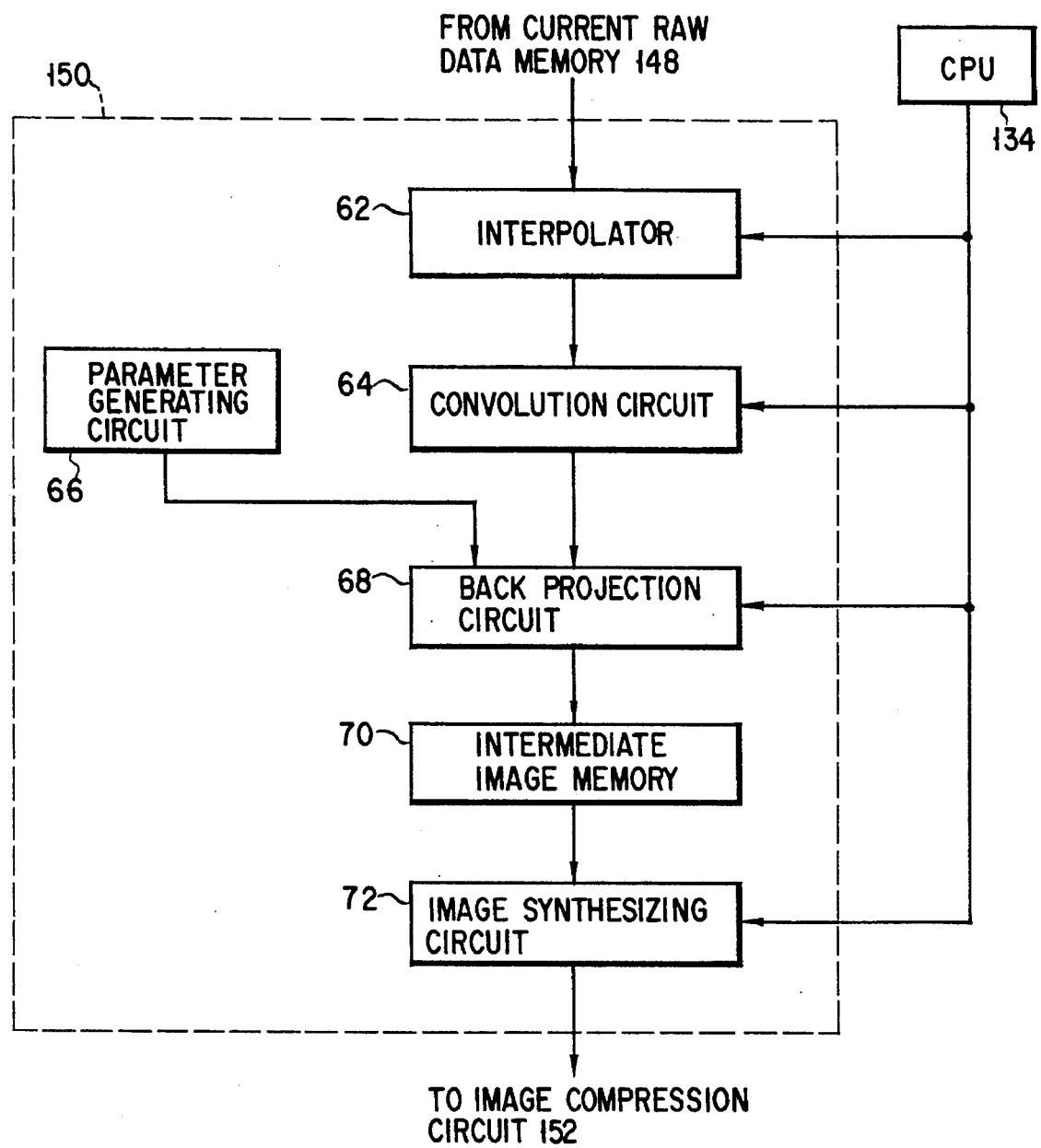
F I G. 30

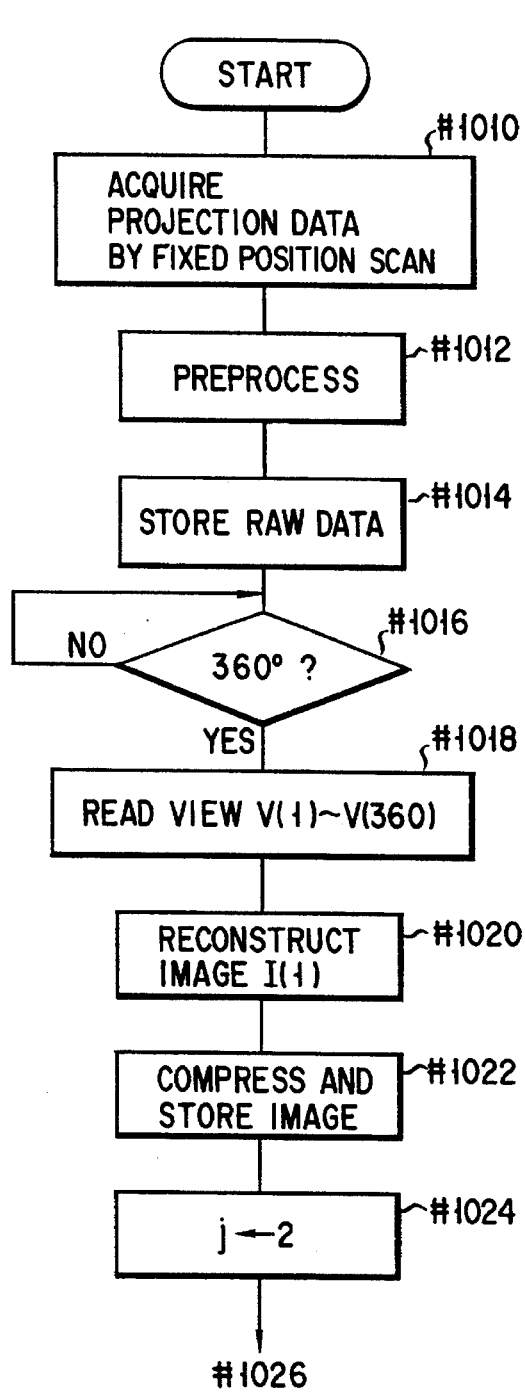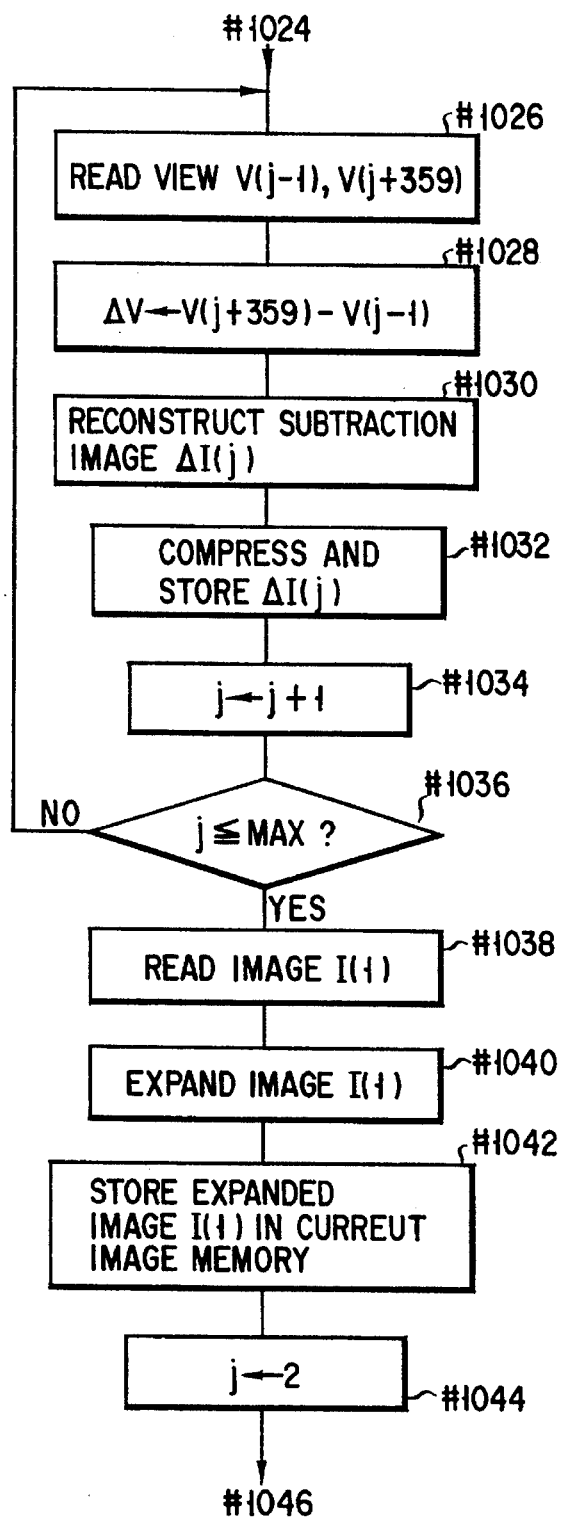
F I G. 31              F I G. 32

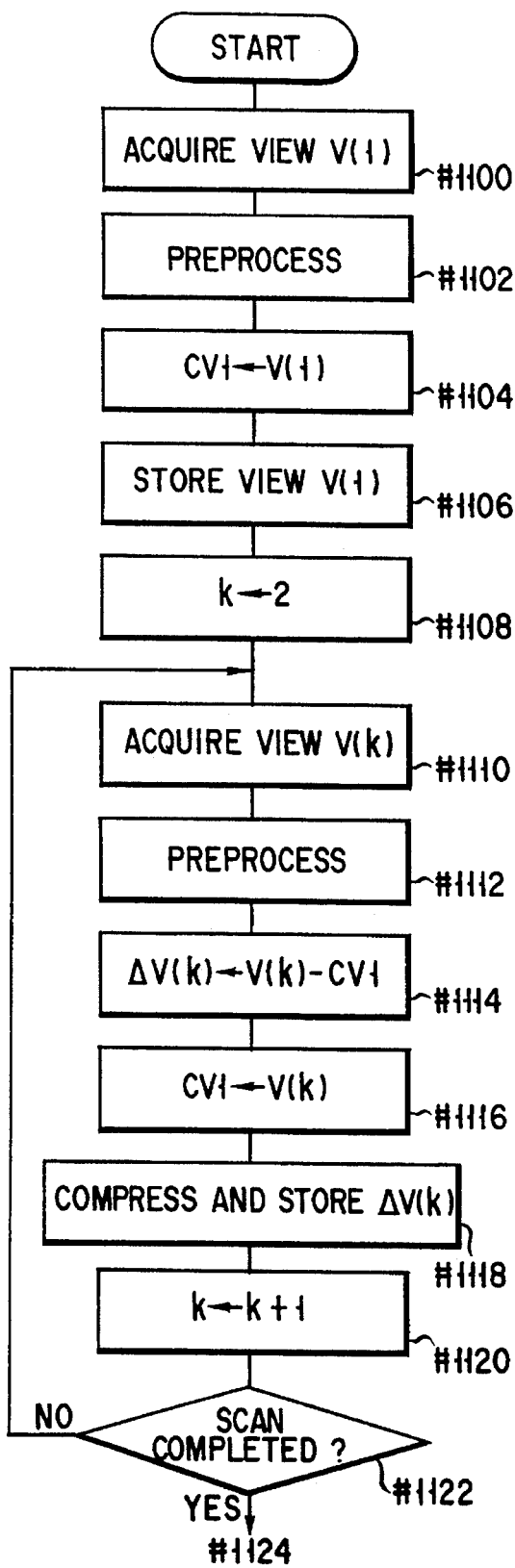
F I G. 34
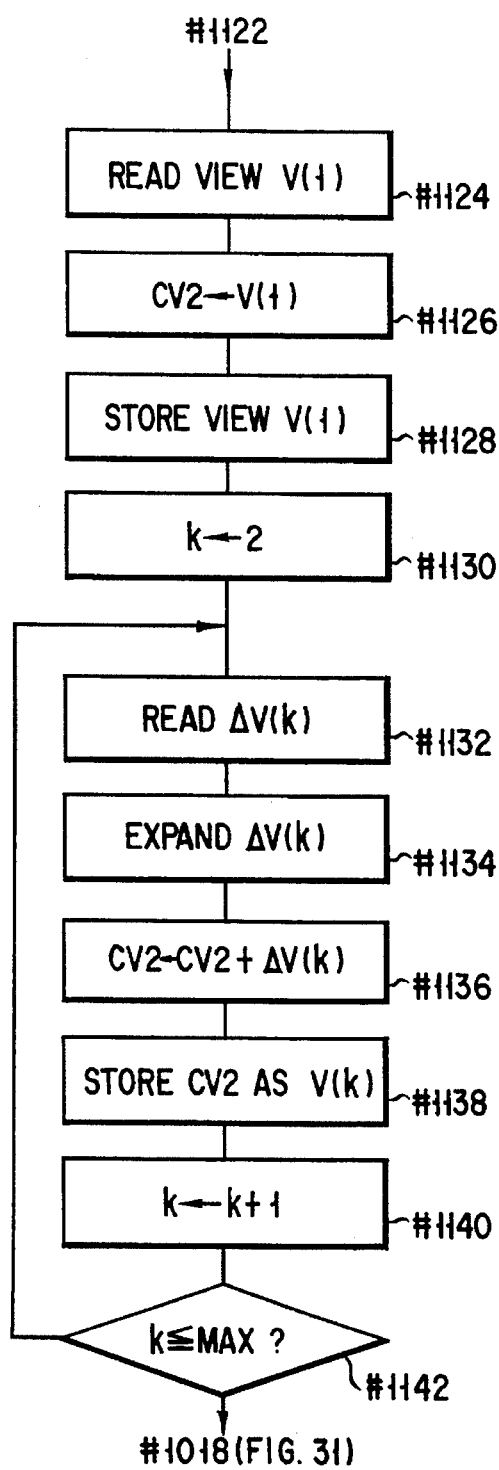
F I G. 35

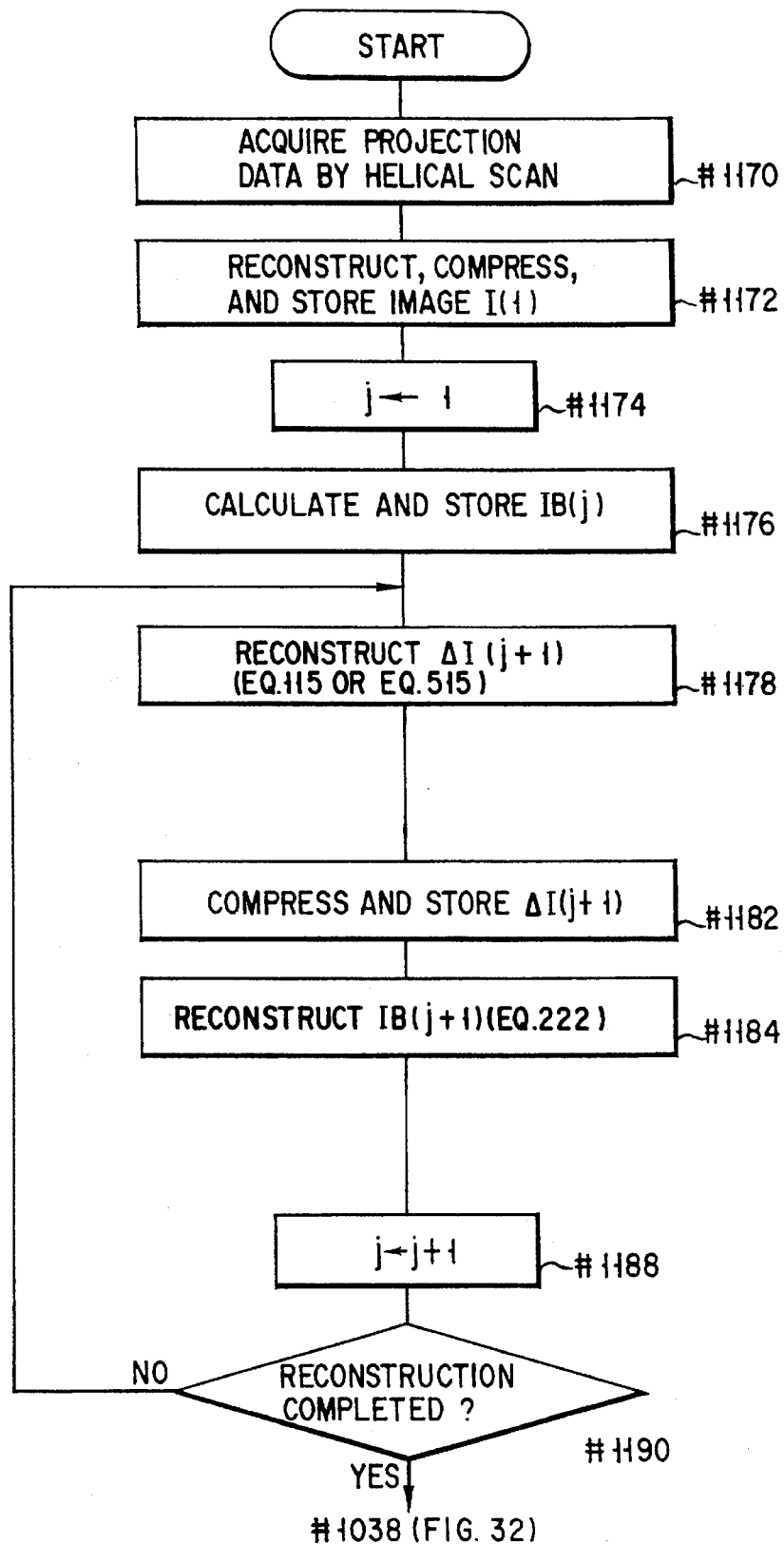
F I G. 37

| PROJECTION DATA | | VIRTUAL PROJECTION DATA | |
|---|---|---|---|
| VIEW ANGLE | VIEW NUMBER(m) | VIEW ANGLE | VIEW NUMBER(m) |
| 0.25 | 1 | | |
| 0.5 | 2 | | |
| 0.75 | 3 | | |
| . | . | | |
| . | . | | |
| . | . | | |
| 220 | 880 | | |
| 220.25 | 881 | 220.25 | 881 |
| . | . | . | . |
| . | . | . | . |
| 360 | 1440 | 360 | 1440 |
| 0.25 | 1441 | 0.25 | 1441 |
| 0.5 | 1442 | 0.5 | 1442 |
| . | . | . | . |
| . | . | . | . |
| 0.25 | 2881 | 0.25 | 2881 |
| . | . | . | . |
| . | . | . | . |
| 0.25 | 4321 | 0.25 | 4321 |
| . | . | . | . |
| . | . | . | . |
| 360 | 7200 | 360 | 7200 |
| | | 0.25 | 7201 |
| | | 0.5 | 7202 |
| | | . | . |
| | | . | . |
| | | 140 | 7760 |

F I G. 38

COMPUTED TOMOGRAPHY APPARATUS

BACKGROUND OF THE INVENTION

1. Field of the Invention

The present invention relates to a computed tomography apparatus for obtaining a tomographic image by acquiring projection data by rotating an X-ray beam around an object to be examined, and performing a reconstruction calculation of the projection data.

2. Description of the Related Art

As an example of an apparatus of this type, an X-ray computed tomography apparatus (to be referred to as an X-ray CT apparatus hereinafter) is known. The X-ray CT apparatus is widely used not only for a medical use but also for an industrial use as an apparatus for obtaining a tomographic image of an object to be examined. In particular, an X-ray CT apparatus in the medical use occupies an important position as image diagnosis equipment. A recent X-ray CT apparatus has a very high scan speed and a short total imaging time as compared to early ones. However, demand has arisen for an imaging operation in a still shorter imaging time, since a short imaging time is required to obtain an image representing movement of a contrast medium injected into a human body in, e.g., a so-called dynamic scan. Therefore, in recent years, an X-ray CT apparatus, which can attain continuous scan using a slip ring, has been developed.

Upon rotation of an X-ray beam around an object to be examined, a helical scan for performing continuous scan by moving the object to be examined in a slice direction (body axis direction) allows a volume scan. According to this helical scan, a large number of tomographic images can be obtained within a short period of time.

A method for imaging slices one by one while fixing an object to be examined in position during rotation of an X-ray beam is called a fixed position scan. For the sake of simplicity, the slice direction perpendicular to a tomographic image, i.e., the moving direction of an object to be examined is defined as a Z axis. A set of projection data belonging to a single fan angle will be referred to as a view hereinafter.

In the helical scan, since an object to be examined is continuously moved in the Z axis direction during rotation of an X-ray beam, the positions of data in 360° views are not constant. Therefore, in order to reconstruct a tomographic image at a certain position, 360° virtual views at that position must be calculated.

In a typical method for calculating virtual views, virtual views are calculated by interpolating 360° projection view data relating to slice positions before and after a slice position of a tomographic image to be obtained, i.e., a total of 720° projection view data. This method is popularly used in clinical examinations. However, since this method uses data for two revolutions of an X-ray beam, and an object to be examined is moved over a considerable distance during this interval, a tomographic image is considerably blurred in the Z axis direction. Therefore, the following method for calculating virtual views from projection view data in a range of 360°+a double fan opening angle is proposed.

The principle of this second method will be described below with reference to FIG. 1. FIG. 1 is a view called a cynogram, which illustrates projection data. In FIG. 1, a detector number (channel number) "n" is plotted along the abscissa, and a view number (projection number) "m" is plotted along the ordinate. Note that a set of projection data belonging to a single projection number, i.e., a horizontal line of the cynogram constitutes a view. In a fixed position scan, if the number of views is sufficiently large, there is a reflection beam with respect to a beam incident on a single detector which is in an opposite direction. Since the reflection beam has the same path in an object to be examined although they have opposite beam directions, projection data and reflection beam data can be regarded as the same data. In a helical scan method, since the bed is moved, no reflection beams are present in a strict sense. However, beams satisfying the relationship shown in FIG. 2 will be referred to as reflection beams hereinafter for the sake of convenience.

Two circles connected by an arrow in FIG. 1 respectively represent projection data and its reflection beam data or reflection view data. Thus, one projection data of virtual views at a slice position can be calculated by interpolation using one projection data and one reflection beam data acquired at the two sides of the slice position. In the second method, as shown in FIG. 1, 360° virtual views at the slice position are calculated from projection data in a region surrounded by a parallelogram of views within a range of 180°+a fan angle $2\alpha$ before the slice position, and views within a range of 180°+a fan angle $2\alpha$ after the slice position, i.e., views within a range of 360°+a double fan angle $4\alpha$. In this case, all projection data in the region surrounded by the parallelogram are used twice.

Therefore, in the second method, projection data in triangular regions P1 and P2 are used twice although they are farthest from the slice position. Projection data in triangular regions P3 and P4 are not used at all although they have the same projection angles as those of the projection data in the regions P2 and P1, and are closer to the slice position than the regions P1 and P2. As a result, the following drawbacks are posed.

(1) A blur in the Z axis direction cannot be satisfactorily eliminated although it is small as compared to the first method.

(2) A blur in the Z axis direction is non-uniform depending on the pixel positions, and the influence of the blur varies depending on objects to be examined.

According to the X-ray CT apparatus adopting the helical scan, when view groups to be used in reconstruction are sequentially shifted, a large number of tomographic images which are position-shifted little by little can be continuously reconstructed. When such large number of tomographic images are continuously displayed, a pseudo three-dimensional image can be displayed. However, it takes a long time to reconstruct a large number of images one by one. Therefore, demand has arisen for high-speed reconstruction of continuous images in the helical scan.

The applicant of the present invention has already proposed a method of continuously reconstructing a large number of tomographic images according to the first method using 720° views (U.S. Pat. No. 5,315,665).

However, a method of reconstructing continuous tomographic images according to the second method using views in a range of 360°+a double fan angle $4\alpha$ has not been proposed yet.

As described above, as a method of obtaining 360° views at a slice position in a conventional helical scan CT apparatus, the first method using 720° views before and after the slice position, and the second method using views in a range of 360°+a double fan angle $4\alpha$ before and after the slice position are available. In the second method as well, the influence of a blur cannot be eliminated to a satisfactory level upon calculation of virtual views. Furthermore, the first method includes a method of continuously reconstructing a large number of images, but the second method does not include such a method.

In order to perform continuous reconstruction, a large amount of projection data are required, and a large amount of tomographic image data are generated. Therefore, in order to store these data, the storage capacity is undesirably increased very much. Note that continuous reconstruction is not limited to a helical scan CT apparatus, but can be executed by continuous scan by a fixed position scan CT apparatus. Therefore, a drawback associated with an increase in storage capacity is similarly posed in the fixed position scan CT apparatus.

SUMMARY OF THE INVENTION

Accordingly, it is an object of the present invention to provide a helical scan computed tomography apparatus which can continuously reconstruct a large number of images, which are less blurred in a slice direction, and do not suffer from non-uniformity of the blur.

It is another object of the present invention to provide a computed tomography apparatus, which can eliminate a blur upon calculation of virtual view data from projection data obtained by a helical scan.

It is further object of the present invention to provide a computed tomography apparatus, which can efficiently store a large amount of projection data acquired by a continuous fixed position scan or a helical scan.

It is still another object of the present invention to provide a computed tomography apparatus, which can efficiently store a large number of tomographic images upon continuous reconstruction of tomographic images of a large number of neighboring slices.

According to the present invention, there is provided a computed tomography apparatus for performing a helical scan using a fan-shaped radiation beam, the apparatus comprising:

first means for calculating 360° virtual projection data at a first slice position by executing an estimation process of projection data in a range of 360°+a double fan angle acquired before and after the first slice position, and reconstructing a tomographic image at the first slice position from the virtual projection data;

second means for calculating a subtraction image between a tomographic image at a second slice position adjacent to the first slice position, and the tomographic image at the first slice position by reconstructing a difference between 360° virtual projection data necessary for reconstructing the tomographic image at the second slice position, and the 360° virtual projection data at the first slice position; and third means for calculating the tomographic image at the second slice position by synthesizing the subtraction image and the tomographic image at the first slice position.

According to the present invention, there is provided another computed tomography apparatus for performing a helical scan using a fan-shaped radiation beam, the apparatus comprising:

first means for calculating 360° virtual projection data at a first slice position by executing an estimation process of projection data in a range of 360°+a double fan angle acquired before and after the first slice position, and reconstructing a tomographic image at the first slice position from the virtual projection data; and second means for calculating a tomographic image at a second slice position adjacent to the first slice position by reconstructing the tomographic image at the first slice position and a difference between 360° virtual projection data necessary for reconstructing the tomographic image at the second slice position and the 360° virtual projection data at the first slice position.

According to the present invention, there is provided a further computed tomography apparatus for acquiring projection data by executing a helical scan using a fan-shaped radiation beam, and calculating 360° virtual projection data at an arbitrary slice position from projection data at a slice position near the slice by an estimation process, wherein when projection data used in the estimation process are present at positions sandwiching the slice therebetween, the virtual projection data are calculated by an interpolation, and when projection data used in the interpolation are present at positions which do not sandwich the slice therebetween, the virtual projection data are calculated by an extrapolation.

According to the present invention, there is provided a still another computed tomography apparatus for acquiring projection data by executing a helical scan using a fan-shaped radiation beam, and calculating 360° virtual projection data at an arbitrary slice position from a projection data group at a slice position near the slice by an estimation process, the apparatus comprising:

means for calculating a first reflection beam data group relating to positions before the slice position from the projection data group;

means for calculating a second reflection beam data group relating to positions after the slice position from the projection data group;

means for calculating a first virtual projection data group by interpolating or extrapolating a first projection data group relating to positions in a range of 180° before the slice position, and the first reflection beam data group;

means for calculating a second virtual projection data group by interpolating or extrapolating a second projection data group relating to positions in a range of 180° after the slice position, and the second reflection beam data group; and means for reconstructing an image at the slice position from the first and second virtual projection data groups.

According to the present invention, there is provided a still further computed tomography apparatus for performing a helical scan using a fan-shaped radiation beam, the apparatus comprising:

reconstruction means for reconstructing a first tomographic image at a first slice position;

calculating means for calculating a subtraction image between a second tomographic image at a second slice position adjacent to the first slice position and the first tomographic image using difference data between a first data group necessary for said reconstruction means to calculate the first tomographic image, and a second data group necessary for said reconstruction means to calculate the second tomographic image; and storage means for compressing and storing the subtraction image.

According to the present invention, there is provided a still another computed tomography apparatus for performing a helical scan using a fan-shaped radiation beam, the apparatus comprising:

storage means for compressing and storing projection data;

reconstruction means for reconstructing a first tomographic image at a first slice position using the data stored in said storage means; and means for calculating a subtraction image between a second tomographic image at a second slice position adjacent to the first slice position, and the first tomographic image by using difference data between a first data group necessary to reconstruct the first tomographic image, and a second data group necessary to reconstruct the second tomographic image in said storage means.

According to the computed tomography apparatus of the present invention, 360° virtual views at a slice position are calculated using view data in a range of 360°+a double fan angle acquired before and after the slice position. A tomographic image of the first slice is obtained by executing a normal reconstruction calculation of the obtained virtual views. A tomographic image of a slice adjacent to the first slice is obtained on the basis of the difference between data used upon reconstruction of the tomographic image of the first slice and data necessary for reconstructing a current tomographic image to be reconstructed, and the already reconstructed tomographic image. Therefore, a large number of tomographic images can be reconstructed within a short period of time, and a large number of tomographic images whose slice positions are shifted can be continuously reconstructed.

According to the computed tomography apparatus of the present invention, upon calculation of virtual view data from projection data in a range of 360°+a double fan angle before and after a slice position, which are acquired by a helical scan, not only an interpolation but also an extrapolation are performed. Therefore, virtual view data can always be obtained using data at the closest position, and a blur can be eliminated.

According to the computed tomography apparatus of the present invention, since a large amount of data required for reconstructing the tomographic image and acquired by a continuous fixed position scan or a helical scan are compressed and stored, the storage capacity can be reduced.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 3 is a cynogram of projection data acquired by a helical scan;

FIG. 4 is a view showing the relationship between projection data and reflection beam data;

FIG. 9 illustrates a conventional interpolation method;

FIG. 10 is a block diagram showing a computed tomography apparatus according to a first embodiment of the present invention;

FIG. 17 is a flow chart showing a first part of an operation according to a fourth embodiment of the present invention;

FIG. 24 is a flow chart showing the details of an initialization routine in FIG. 23;

FIG. 27 is a flow chart showing the details of an initialization routine in FIG. 26;

FIG. 30 is a block diagram showing the details of an image reconstructing circuit shown in FIG. 29;

FIG. 31 is a flow chart showing a first part of an operation according to the eleventh embodiment of the present invention;

FIG. 32 is a flow chart showing a second part of the operation of the eleventh embodiment;

FIG. 34 is a flow chart showing a first part of an operation according to a twelfth embodiment of the present invention;

FIG. 35 is a flow chart showing a second part of the operation of the twelfth embodiment;

FIG. 37 is a flow chart showing an operation according to a fourteenth embodiment of the present invention; and FIG. 38 is a view for explaining a fifteenth embodiment of the present invention.

DETAILED DESCRIPTION OF THE PREFERRED EMBODIMENTS

Figure 1:
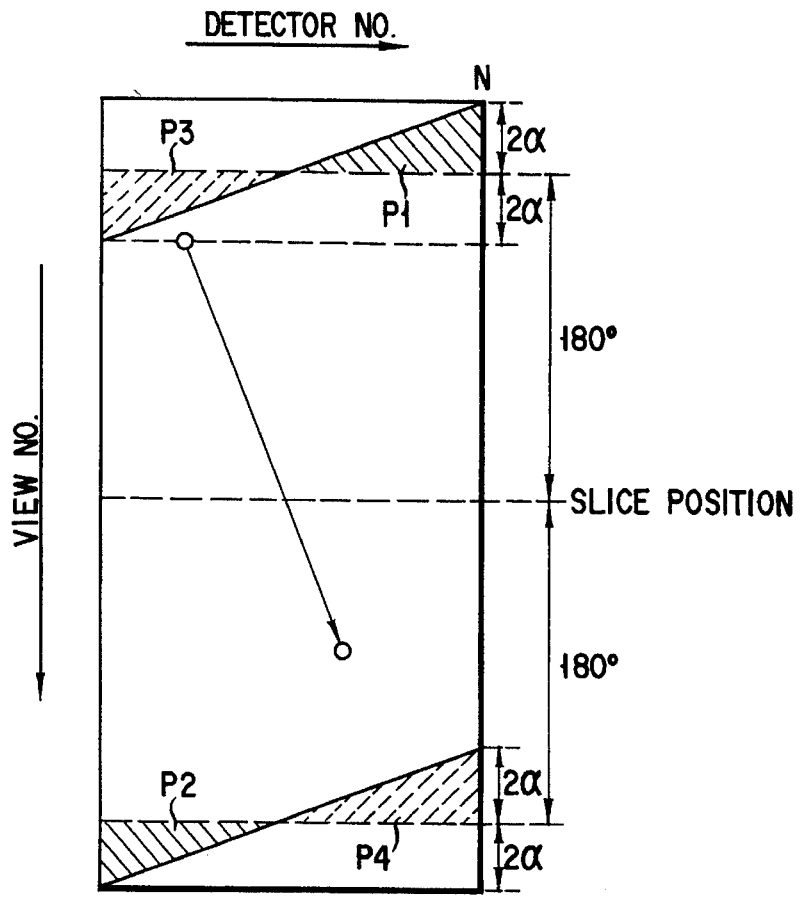
FIG. 1 is a cynogram showing the principle of reconstruction of a conventional helical scan computed tomography apparatus.
Figure 2:
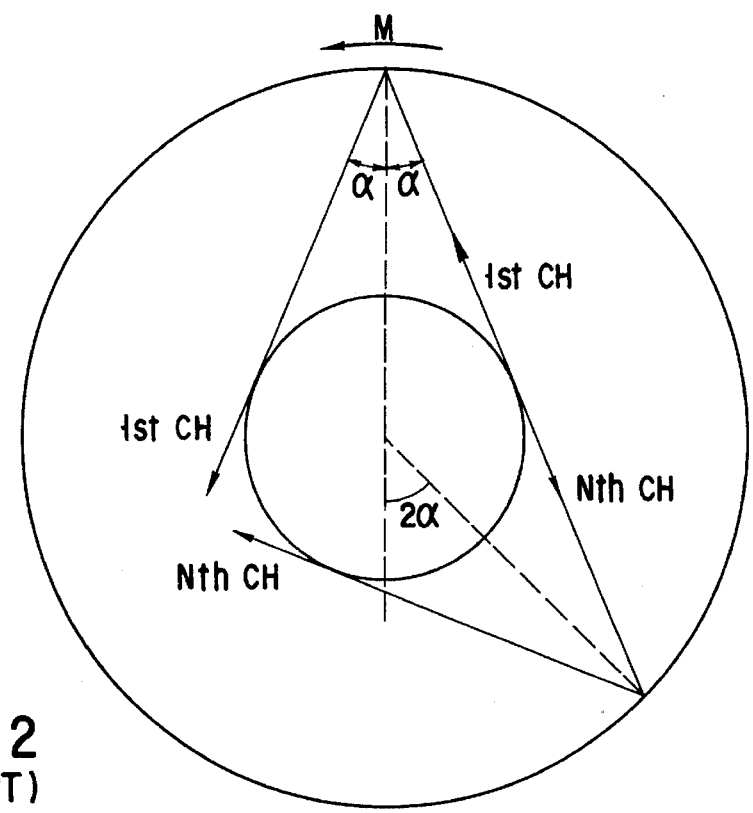
FIG. 2 is a view showing the relationship between projection data and reflection beam data.

Preferred embodiments of a computed tomography apparatus according to the present invention will now be described with reference to the accompanying drawings.

As a first embodiment, a so-called third generation X-ray CT apparatus adopting an R/R (Rotate/Rotate) system, in which an X-ray tube and a detector array are arranged to oppose each other to sandwich an object to be examined therebetween, and which allows continuous scan over 360°, will be described.

The principle of the first embodiment will be described below. Assume that projection data are acquired using a fan beam by a helical scan. Since the helical scan is popularly used in many third generation X-ray CT apparatuses, a detailed description thereof will be omitted.

Projection data is defined as follows. For the sake of convenience, an X-ray detector array for detecting a fan beam is arranged symmetrically about a line (to be referred to as a center line hereinafter) connecting the focal point of an X-ray tube and the center of rotation. However, the present invention can be almost similarly practiced even when the X-ray detector array is arranged asymmetrically.

An opening angle (fan angle) of the fan beam is represented by $2\alpha$, and the number of channels (the number of detectors) of the detector array is represented by N (even number). Therefore, the fan angle $\Delta\alpha$ per channel is given by $\Delta\alpha=2\alpha/N$.

The rotational angle of an X-ray beam between adjacent views is represented by $\Delta\theta$, and the number of views per 360° is represented by M (even number). Therefore, $M\times\Delta\theta=360°$.

The view number is represented by "m", the channel number is represented by "n", and the projection data is represented by D(m,n). The angle defined by the center line of an m-th view is referred to as a projection angle. The projection angle of the m-th view is $m\times\Delta\theta$. The moving distance of a gantry between adjacent views is represented by "d", and the position of the m-th view in the Z direction is represented by $m\times d$. The total number of scanned views is represented by MM.

First, a reflection beam in projection data of a fixed position scan will be described below. In the fixed position scan, if the number of views is sufficiently large, each projection data always has reflection beams. Reflection beams includes a beam in an ascending direction of view numbers (to be referred to as the plus side hereinafter) and a beam in a descending direction of view numbers (to be referred to as the minus side hereinafter). Projection data of a reflection beam at the plus side of projection data D(m,n) (to be also referred to as reflection beam data or reflection view data) is represented by RP(m,n), and projection data of a reflection beam at the minus side of the projection data D(m,n) is represented by RM(m,n). These projection data D, RP, and RM do not coincide with each other in a strict sense since a fan beam spreads. However, D(m,n), RP(m,n), and RM(m,n) can be regarded as identical beam data in a practical use.

Therefore, if RP(m,n) and RM(m,n) are defined as:

$$RP(m,n)=D(mp,nn) \quad (1)$$

$$RM(m,n)=D(mm,nn) \quad (2)$$

Since the channels are symmetrical about the center line, nn, mp, and mm are obtained as follows:

$$nn=N+1-n \quad (3)$$

$$mp=m+M/2-(N+1-2n)\times aa \quad (4)$$

$$mm=m-M/2-(N+1-2n)\times aa \quad (5)$$

where $$aa=\Delta\alpha/\Delta\theta \quad (6)$$

Furthermore, the following definitions are given:

ci: an integral part of $(N-1)\times aa$ cp: a decimal part of $(N-1)\times aa$

Reflection beams of projection data acquired in the helical scan will be described below. In the helical scan, since the gentry is moved, no reflection beams are present in a strict sense. However, beams satisfying the relations of Eqs. (1) to (5) will be referred to as reflection beams hereinafter for the sake of convenience.

As shown in FIG. 3, a certain view is present on a horizontal line of the cynogram, but its reflection view is present on an oblique line. In Eqs. (4) and (5), since mp and mm are not normally integers, they are obtained by interpolation using data of two adjacent views having the same channel number nn. Therefore, if the following definitions are given:

mpi: an integral part of mp mpp: a decimal part of mp mmi: an integral part of mm mmp: a decimal part of mm, reflection beam data RP(m,n) and RM(m,n) are obtained as follows according to the value of m.

When m falls within a range from 1 to (MM–M/2+ci):

$$RP(m,n)=D(mpi,nn)\times(1-mpp)+D(mpi+1,nn)\times mpp \quad (7)$$

When m falls within a range from M/2+ci+2 to MM:

$$RM(m,n)=D(mmi,nn)\times(1-mmp)+D(mmi+1,nn)\times mmp \quad (8)$$

Note that the following relations are satisfied:

$$RP(m,n)=RM(m+M,n) \quad (9)$$

$$RM(m,n)=RP(m-M,n) \quad (10)$$

Therefore, for the sake of simplicity, the following definitions are given:

$$R(mr,n) = RP\{mr-(M/2)+ci+1,n\} \quad (11)$$
$$= RM\{mr+(M/2)+ci+1,n\} \quad (12)$$

Therefore, reflection beam data can be defined as follows:

$$RP(m,n)=R\{m+(M/2)-ci-1,n\} \quad (13)$$

$$RM(m,n)=R\{m-(M/2)-ci-1,n\} \tag{14}$$

Therefore, if the following definitions are given:

$$mmr=mr+ci+1-(N+1-2n)\times aa \tag{15}$$

mmri: an integral part of mmr
mmrp: a decimal part of mmr,
R(mr,n) is given by:

$$R(mr,n)=D(mmri,nn)\times(1-mmrp)+D(mmri+1,nn)\times mmrp \tag{16}$$

where mr=1 to MM−2ci−2

Figure 5:
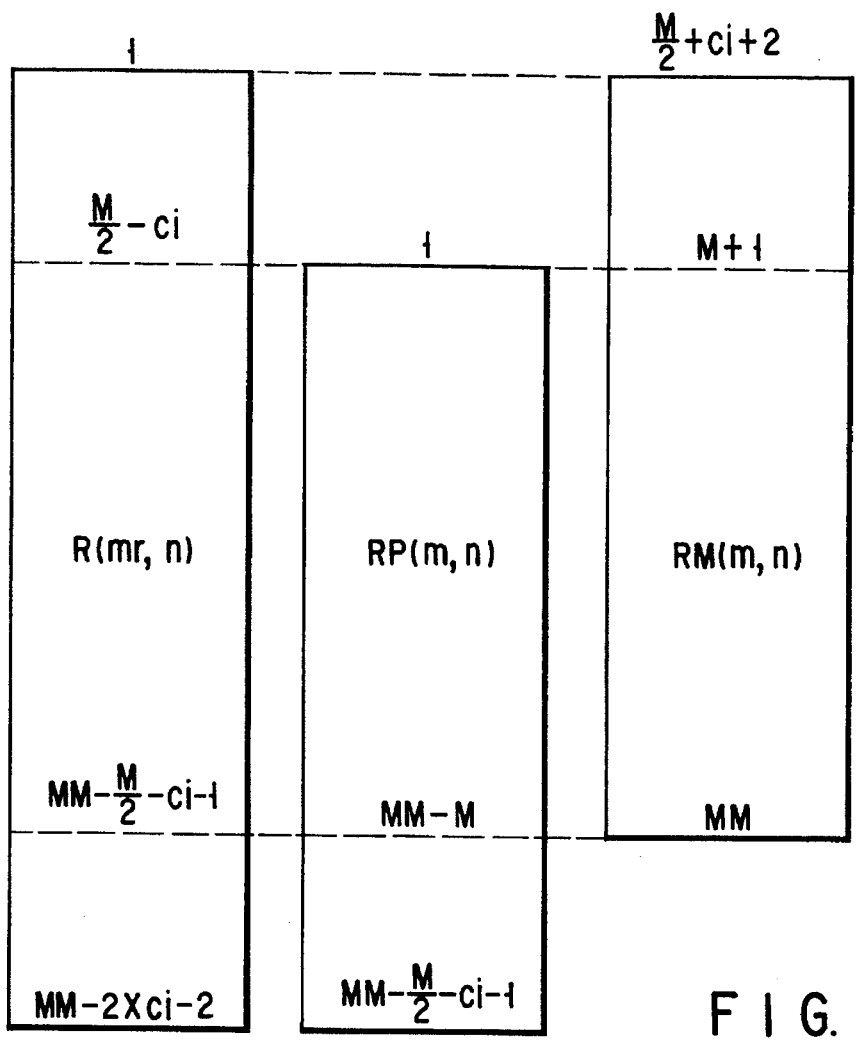
FIG. 5 is a view showing the relationship between plus reflection beam data and minus reflection beam data.

FIG. 4 shows the relationship between projection data D(m,n) and reflection beam data R(mr,n), and FIG. 5 shows the relationship among reflection beam data R(mr,n), plus-side reflection beam data RP(m,n), and minus-side reflection beam data RM(m,n). Note that the numerals in FIG. 5 indicate the view numbers.

Calculation of virtual projection data at a slice position in the helical scan will be described below.

Projection data of virtual views on a slice can be obtained by interpolation or extrapolation (in general, a linear interpolation or extrapolation) of projection data and reflection beam data thereof. The linear interpolation is performed according to the distance between two beams and the slice position, and as the two beams, those which are as close to the slice position as possible are used. Note that the interpolation or extrapolation is not limited to a linear interpolation or extrapolation, but a higher-order interpolation or extrapolation may be used.

Figure 6:
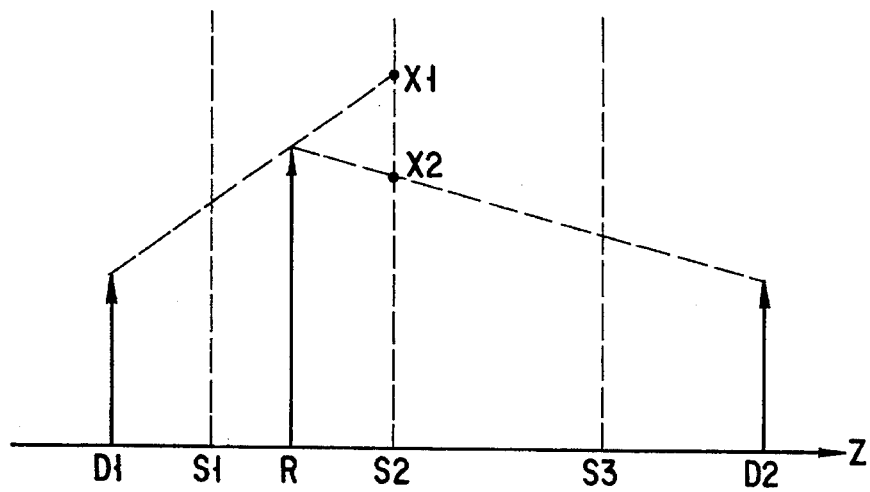
FIG. 6 is a view for explaining an interpolation or extrapolation between projection data and reflection beam data for estimating virtual view data.

FIG. 6 shows the positional relationship between projection data and reflection beam data. Projection data D1 and D2 are separated by one revolution (360°). Reflection beam data R (RP for D1; RM for D2) is located between the projection data D1 and D2. As the slice position, a slice position S1 located between the projection data D1 and the reflection beam data R, and slice positions S2 and S3 located between the reflection beam data R and the projection data D2 will be examined.

In general, a linear interpolation is performed using two beams which sandwich a slice position therebetween, and are closest to the slice position. Therefore, data at the slice position S1 is obtained by executing an interpolation using the projection data D1 and the reflection beam data R, and data at the slice positions S2 and S3 are obtained by executing an interpolation using the reflection beam data R and the projection data D2.

Thus, the data at the slice position S2 becomes X2 upon execution of an interpolation using the reflection beam data R and the projection data D2. However, the data at the slice position S2 can also be obtained by an extrapolation based on the projection data D1 and the reflection beam data R. When the extrapolation is executed, data X1 is obtained. The linear interpolation and linear extrapolation have the same precision. Since the interpolation and the extrapolation are a method of estimating non-existing data, it cannot be decided as to which method is suitable, but a method of estimating data from close data is often suitable. Therefore, the precision of virtual view data estimation can be improved using not only an interpolation but also an extrapolation. Therefore, according to the present invention, virtual view data are estimated using not only an interpolation but also an extrapolation. As will be described later, since more data close to a slice position are used upon estimation of virtual view data, a blur in the Z axis direction can be eliminated, and the degree of blur can become uniform independently of the pixel positions.

The position, in the Z direction, of the projection data D(m,n) is represented by DP(m,n). As described above, reflection beams used in calculation of virtual projection data include plus- and minus-side reflection beams. However, since it is unknown which of reflection beams is used, reflection beam data is represented by RR(m,n), and its position is represented by RRP(m,n). If the slice position is represented by SP, virtual projection data DD(m,n) at a slice is given by:

$$\begin{aligned}DD(m,n) = & [D(m,n)\times\{RRP(m,n)-SP\}+ \\ & RP(m,n)\times\{SP-DP(m,n)\}]/ \\ & \{RRP(m,n)-DP(m,n)\}\end{aligned} \tag{17}$$

The image (slice) number will be defined. An image reconstructed using 360° virtual views having virtual view No. j to No. (j+M−1) is defined as a j-th image.

Selection of a reflection beam used in calculation of virtual data will be described below.

Figure 7:
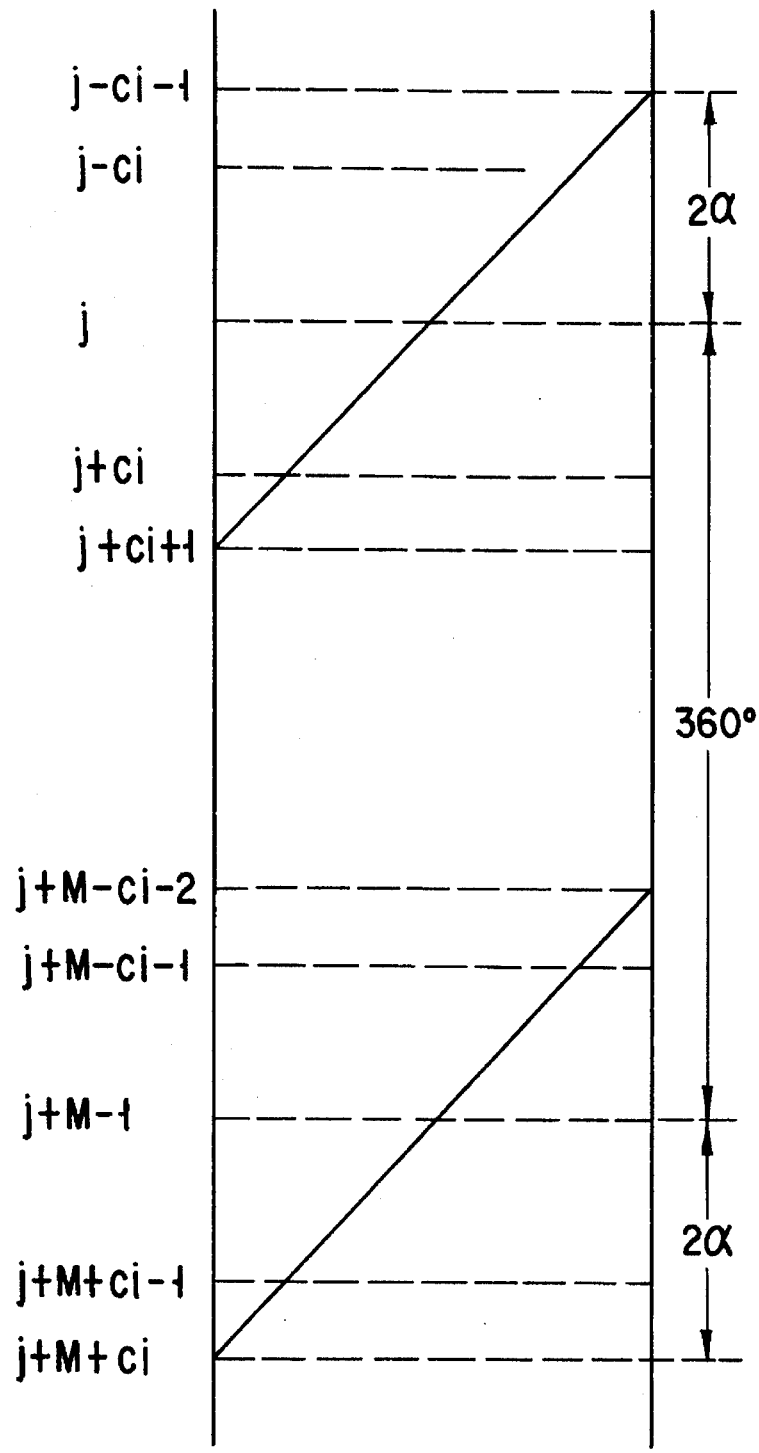
FIG. 7 shows a range of views used in calculation of virtual view data.

Assume that the j-th image is to be reconstructed. Views of No. j to No. (j+M−1) are used in reconstruction of the j-th image. In the present invention, views in a range of 360°+a double fan angle (4α) are used. Therefore, views used in calculation of this virtual views are of No. (j−ci−1) to No. (j+M+ci). FIG. 7 shows this relationship.

Figure 8:
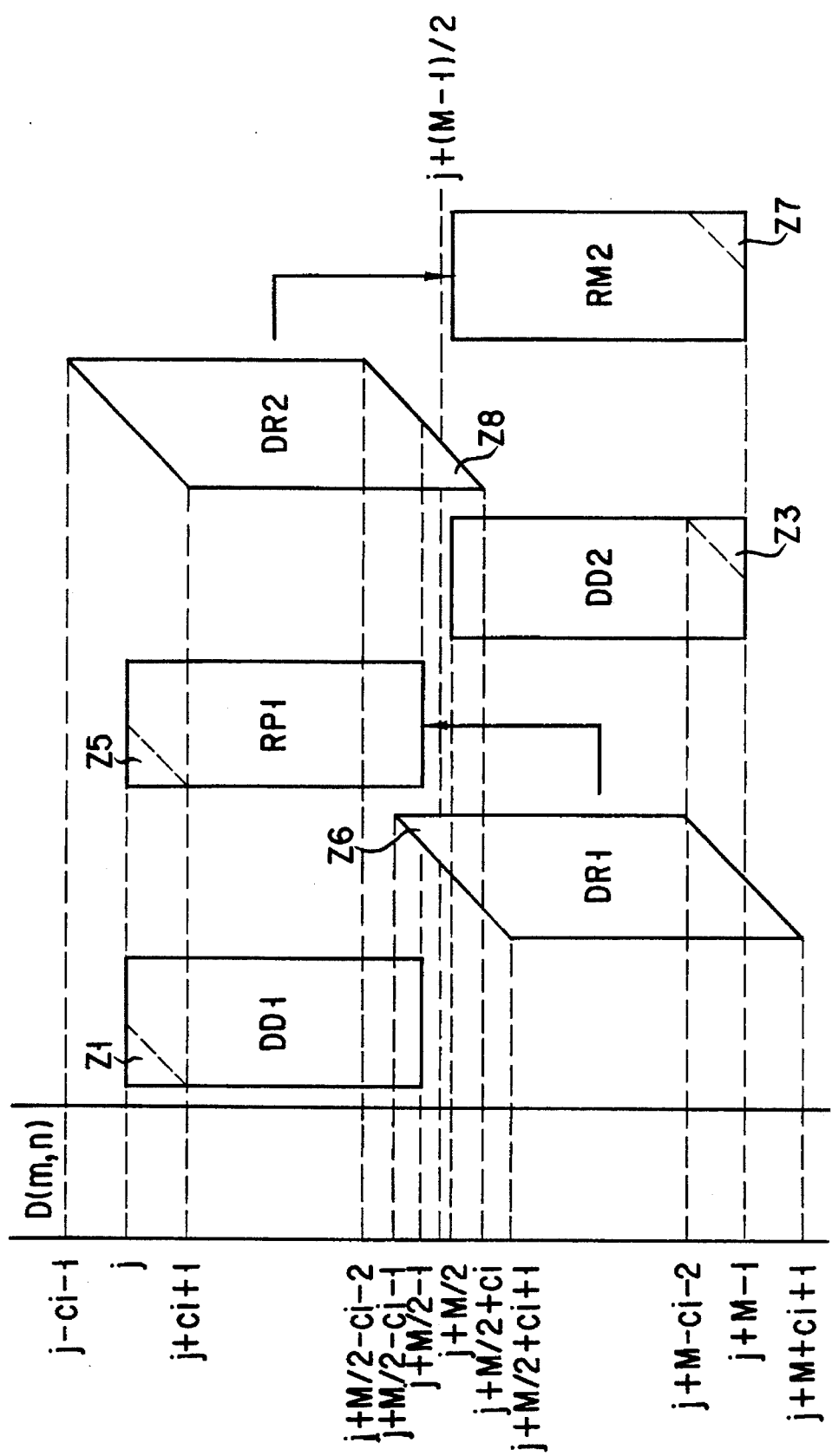
FIG. 8 illustrates an interpolation or extrapolation method according to the present invention.

Referring to FIG. 8, which shows the details of FIG. 7, DD1 and DR1 portions are extracted from projection views D(m,n). An RP1 portion is a plus-side reflection beam for the DD1 portion extracted from a plus-side reflection beam. Here, the RP1 portion is calculated based on the DR1 portion.

In the present invention, in order to calculate virtual views of No. j to No. (j+M/2−1), projection views of No. j to No. (j+M/2−1), i.e., the DD1 portion, and views of No. j to No. (j+M/2−1) of the plus-side reflection beam RP, i.e., the RP1 portion are used. Therefore, if the position of the reflection beam data RP(m,n) is represented by RPP(m,n), virtual view data DD(m,n) can be obtained as follows by replacing RR(m,n) and RRP(m,n) in Eq. (17) respectively by RP(m,n) and RPP(m,n).

$$\begin{aligned}DD(m,n) = & [D(m,n)\times\{RPP(m,n)-SP\}+ \\ & RP(m,n)\times\{SP-DP(m,n)\}]/ \\ & \{RPP(m,n)-DP(m,n)\}\end{aligned} \tag{18}$$

Referring to FIG. 8, DD2 and DR2 portions are extracted from projection views D(m,n). An RM2 portion is a minus-side reflection beam for the DD2 portion extracted from a minus-side reflection beam. Here, the RM2 portion is calculated based on the DR2 portion.

In the present invention, in order to calculate virtual views of No. (j+M/2) to No. (j+M−1), projection views of No. (j+M/2) to No. (j+M−1), i.e., the DD2 portion, and views of No. (j+M/2) to No. (j+M−1) of the minus-side reflection beam RM, i.e., the RM2 portion are used. Therefore, if the position of the reflection beam data RM(m,n) is represented by RMP(m,n), virtual view data DD(m,n) can be obtained as follows by replacing RR(m,n) and RRP(m,n) in Eq. (17) respectively by RM(m,n) and RMP(m,n).

$$\begin{aligned}DD(m,n) = & [D(m,n)\times\{RMP(m,n)-SP\}+ \\ & RM(m,n)\times\{SP-DP(m,n)\}]/ \\ & \{RMP(m,n)-DP(m,n)\}\end{aligned} \tag{19}$$

FIG. 9 shows a conventional interpolation method for the sake of comparison. According to the method of the present invention shown in FIG. 8, projection data DD1(m,n) in a region Z1 is positionally interpolated with data in a region Z5 of reflection beam data RP1(m,n) having the same projection angle. The data in the region Z5 is obtained based on data in a region Z6 of data DR1(m,n). Therefore, the projection position of the region Z5 corresponds to the region Z6. The regions Z1 and Z6 (or Z5) cannot be used for interpolation since they do not sandwich a slice position j+(M−1)/2 therebetween. Therefore, the conventional method shown in FIG. 9 uses the following Eq. in place of Eq. (18):

$$DD(m,n) = [D(m+M,n) \times \{SP - RPP(m,n)\} + \quad (18a)$$
$$RP(m,n) \times \{DP(m+M,n) - SP\}]/$$
$$\{DP(m+M,n) - RPP(m,n)\}$$

Similarly, according to the conventional method shown in FIG. 9, projection data D(m,n) in a region Z3 and reflection beam data RM(m,n) in a region Z8 (or Z7) cannot be used for interpolation since they do not sandwich the slice position j+(M−1)/2 therebetween. Therefore, the conventional method uses the following Eq. in place of Eq. (19):

$$DD(m,n) = [D(m-M,n) \times \{RMP(m,n) - SP\} + \quad (19a)$$
$$RM(m,n) \times \{SP - DP(m-M,n)\}]/$$
$$\{RMP(m,n) - DP(m-M,n)\}$$

Upon comparison between FIGS. 8 and 9, although the regions Z1 and Z2, and regions Z3 and Z4 are data respectively having the same projection angles, the regions Z1 and Z3 are closer to the slice position than the regions Z2 and Z4 are. Therefore, the method of the present invention can provide an image which is less blurred and is less non-uniform, as compared to the conventional method.

Since the slice position is normally present at the center of views to be used, it is calculated as follows:

$$SP = \{j+(M-1)/2\} \times d \quad (20)$$

Since the conventional method only uses an interpolation, the slice position is limited to the center of views to be used. However, since the method of the present invention also uses an extrapolation, the slice position is not limited to the center of views. This is another merit of the present invention.

Interpolation coefficients RP(m,n), RPP(m,n), RM(m,n), and RMP(m,n) required upon calculations of Eqs. (18) and (19) will be calculated in advance. For the sake of easy understanding, the following parameters are used.

$$k = m - j + 1 \quad (21)$$

where k=1 to M
Therefore, m is given by:

$$m = k + j - 1 \quad (22)$$

where m=j to j+M−1
Therefore, the following relations are obtained:

$$\begin{aligned} SP - DP(m,n) &= \{j+(M-1)/2\} \times d - m \times d & (23) \\ &= \{j+(M-1)/2 - k - j + 1\} \times d \\ &= \{(M+1)/2 - k\} \times d \end{aligned}$$

$$\begin{aligned} RPP(m,n) - SP &= mp \times d - \{j+(M-1)/2\} \times d & (24) \\ &= \{m + M/2 - (N+1-2n) \times aa\} \times \\ &\quad d - \{j+(M-1)/2\} \times d \\ &= \{k - 1/2 - (N+1-2n) \times aa\} \times d \end{aligned}$$

$$\begin{aligned} RPP(m,n) - DP(m,n) &= mp \times d - m \times d & (25) \\ &= \{m + (M/2) - (N+1-2n) \times \\ &\quad aa\} \times d - m \times d \\ &= \{(M/2) - (N+1-2n) \times aa\} \times d \end{aligned}$$

$$\begin{aligned} RMP(m,n) - SP &= mm \times d - \{j+(M-1)/2\} \times d & (26) \\ &= \{m - (M/2) - (N+1-2n) \times aa\} \times \\ &\quad d - \{j+(M-1)/2\} \times d \\ &= \{k - (1/2) - (N+1-2n) \times \\ &\quad aa - M\} \times d \end{aligned}$$

$$\begin{aligned} RMP(m,n) - DP(m,n) &= mm \times d - m \times d & (27) \\ &= \{m - (M/2) - (N+1-2n) \times \\ &\quad aa\} \times d - m \times d \\ &= \{-(M/2) - (N+1-2n) \times \\ &\quad aa\} \times d \end{aligned}$$

Therefore, Eq. (18) representing a virtual view can be modified as follows:

$$\begin{aligned} DD(k+j-1,n) &= \{D(k+j-1,n) \times H2(k,n) + & (28) \\ &\quad RP(k+j-1,n) \times H1(k)\}/H4(n) \end{aligned}$$

for k = 1 to M/2

Similarly, Eq. (19) representing a virtual view can be modified as follows:

$$\begin{aligned} DD(k+j-1,n) &= \{D(k+j-1,n) \times H3(k,n) - & (29) \\ &\quad RM(k+j-1,n) \times H1(k)\}/H5(n) \end{aligned}$$

for k = M/2 + 1 to M

In this case, H1(k) to H5(k) are defined as follows:

$$H1(k) = \{(M+1)/2\} - k \quad (30)$$

where k=1 to M $$H2(k,n) = k - \tfrac{1}{2} - (N+1-2n) \times aa \quad (31)$$

where k=1 to M/2

$$H3(k,n) = M - (k-1)/2 - (N+1-2n) \times aa \quad (32)$$

where k=M/2+1 to M $$H4(n) = M/2 - (N+1-2n) \times aa \quad (33)$$

$$H5(n) = M/2 + (N+1-2n) \times aa \quad (34)$$

The principle of continuous reconstruction will be described below. The following variables are defined:

$$DE(m,n) = D(m,n)/H4(n) \quad (35)$$

$$DF(m,n) = D(m,n)/H5(n) \quad (36)$$

$$RPE(m,n) = RP(m,n)/H4(n) \quad (37)$$

$$RMF(m,n) = RM(m,n)/H5(n) \quad (38)$$

$$H1M = (M+1)/2 \quad (39)$$

$$H2N(n) = -\tfrac{1}{2} - (N+1-2n) \times aa \quad (40a)$$

$$H3N(n) = M/2 + \tfrac{1}{2} + (N+1-2n) \times aa \quad (40b)$$

From these definitions, Eqs. (28) to (32) can be expressed as follows:

$$DD(k+j-1,n) = H2(k,n) \times DE(k+j-1,n) + H1(k) \times RPE(k+j-1,n) \quad (41)$$

for k=1 to M/2

$$DD(k+j-1,n)=H3(k,n)\times DF(k+j-1,n)+H1(k)\times RMF(k+j-1,n) \quad (42)$$

for k=M/2+1 to M $$H1(k)=H1M-k \quad (43)$$

$$H2(k,n)=H2N(n)+k \quad (44)$$

$$H3(k,n)=H3N(n)-\{k=(M/2)\} \quad (45)$$

here

DEU(j): a set of DE(k+j−1,n)
where k=1 to M/2
RPEU(j): a set of RPE(k+j−1,n)
where k=1 to M/2
DFU(j): a set of DF(k+j−1,n)
where k=M/2+1 to M
RMFU(j): a set of RMF(k+j−1,n)
where k=M/2+1 to M
DEHU(j): a set of H2N(n)×DE(k+j−1,n)
where k=1 to M/2
DFHU(j): a set of H3N(n)×DF(k+j−1,n)
where k=M/2+1 to M
DEKU(j): a set of k×DE(k+j−1,n)
where k=1 to M/2
RPKU(j): a set of k×RPE(k+j−1,n)
where k=1 to M/2
DFKU(j): a set of (k−M/2)×DF(k+j−1,n)
where k=M/2+1 to M
RMKU(j): a set of (k−M/2)×RMF(k+j−1,n)
where k=M/2+1 to M The following images are defined:

$$IEA(j)=BP[CONV\{DEU(j)\}] \quad (46)$$

$$IRPA(j)=BP[CONV\{RPEU(j)\}] \quad (47)$$

$$IFA(j)=BP[CONV\{DFU(j)\}] \quad (48)$$

$$IRMA(j)=BP[CONV\{RMFU(j)\}] \quad (49)$$

$$IEH(j)=BP[CONV\{DEHU(j)\}] \quad (50)$$

$$IFH(j)=BP[CONV\{DFHU(j)\}] \quad (51)$$

$$IEK(j)=BP[CONV\{DEKU(j)\}] \quad (52)$$

$$IRPK(j)=BP[CONV\{RPKU(j)\}] \quad (53)$$

$$IFK(j)=BP[CONV\{DFKU(j)\}] \quad (54)$$

$$IRMK(j)=BP[CONV\{RMKU(j)\}] \quad (55)$$

where
BP: back projection calculation
CONV: convolution calculation.
The BP and CONV calculations are performed in units of projection angles.
where
DDU(j): a set of DD(k+j−1,n)
where k=1 to M/2
DDV(j): a set of DD(k+j−1,n)
where k=M/2+1 to M If the j-th image is represented by I(j), I(j) is given by:

$$I(j)=BP[CONV\{DDU(j)\}]+BP[CONV\{DDV(j)\}] \quad (55a)$$

Therefore, $$\begin{aligned}I(j) = & IEH(j) + IEK(J) + H1M \times IRPA(j) - \\ & IRPK(j) + IFH(j) - IFK(j) - (1/2) \times \\ & IRMA(j) + IRMK(j)\end{aligned} \quad (56)$$

Similarly, a (j+1)-th image is given by:

$$\begin{aligned}I(j+1) = & IEH(j+1) + IEK(j+1) + \\ & H1M \times IRPA(j+1) - IRPK(j+1) + \\ & IFH(j+1) - IFK(j+1) - \\ & (1/2) \times IRMA(j+1) + IRMK(j+1)\end{aligned} \quad (57)$$

If a subtraction image between the (j+1)-th and j-th images is represented by ΔI(j+1), ΔI(j+1) is given by:

$$\begin{aligned}\Delta I(j+1) = & I(j+1) - I(j) \\ = & IEH(j+1) - IEH(j) + \\ & IEK(j+1) - IEK(j) + \\ & H1M \times (IRPA(j+1) - IRPA(j)) - \\ & (IRPK(j+1) - IRPK(j)) + \\ & IFH(j+1) - IFH(j) - \\ & (IFK(j+1) - IFK(j)) - \\ & (1/2) \times (IRMA(j+1) - IRMA(j)) + \\ & IRMK(j+1) - IRMK(j)\end{aligned} \quad (58)$$

The terms of the right-hand side of Eq. (58) are sequentially calculated as follows:
First, $$\begin{aligned}IEH(j+1) - IEH(j) = & BP[CONV\{-H2N(n) \times \\ & DE(j,n)\}] + \\ & BP[CONV\{H2N(n) \times \\ & DE(j+(M/2),n)\}]\end{aligned} \quad (59)$$

$$\begin{aligned}IFH(j+1) - IFH(j) = & BP[CONV\{-H3N(n) \times \\ & DF(j+(M/2),n)\}] + \\ & BP[CONV\{H3N(n) \times \\ & DF(j+M,n)\}]\end{aligned} \quad (60)$$

Since DE(j,n) and DF(j+M,n) have the same projection angle, Eqs. (59) and (60) are summarized as follows:

$$\begin{aligned}IEH(j+1) - IEH(j) + IFH(j+1) - IFH(j) = & \\ BP[CONV\{H3N(n) \times DF(j+M,n) - H2N(n) \times DE(j,n)\}] + & \\ BP[CONV\{H2N(n) \times DE(j+(M/2),n) - & \\ H3N(n) \times DF(j+(M/2),n)\}] & \end{aligned} \quad (61)$$

Next, $$IEK(j+1) - IEK(j) = -IEA(j) + BP[CONV\{(M/2) \times DE(j+(M/2),n)\}] \quad (62)$$

Note that IEA(j+1) is given by:

$$\begin{aligned}IEA(j+1) = & IEA(j) - BP[CONV\{DE(j,n)\}] + \\ & BP[CONV\{DE(j+(M/2),n)\}]\end{aligned} \quad (63)$$

Next, $$\begin{aligned}IFK(j+1) - IFK(j) = & -IFA(j) + \\ & BP[CONV\{(M/2) \times DF(j+M,n)\}]\end{aligned} \quad (64)$$

Note that IFA(j+1) is give by:

$$\begin{aligned}IFA(j+1) = & IFA(j) - BP[CONV\{DF(j+(M/2),n)\}] + \\ & BP[CONV\{DF(j+M,n)\}]\end{aligned} \quad (65)$$

Here, we define:

$$IEFA(j)=IEA(j)-IFA(j) \quad (66)$$

From Eq. (66), the following Eq. is obtained:

$$IEFA(j+1) = IEFA(j) - BP[CONV\{DE(j,n)\}] + \quad (67)$$
$$BP[CONV\{DE(j+(M/2),n)\}] +$$
$$BP[CONV\{DF(j+(M/2),n)\}] -$$
$$BP[CONV\{DF(j+M,n)\}]$$

Since $DE(j,n)$ and $DF(j+M,n)$ have the same projection angle, Eq. (67) is modified as:

$$IEFA(j+1) = \quad (68)$$
$$IEFA(j) - BP[CONV\{DE(j,n) + DF(j+M,n)\}] +$$
$$BP[CONV\{DE(j+(M/2),n) + DF(j+(M/2),n)\}]$$

Therefore, $$IEK(j+1) - IEK(j) - = \quad (69)$$
$$-IEFA(j) + \{IFK(j+1) - IFK(j)\}BP[CONV\{(M/2) \times$$
$$DE(j+(M/2),n)\}] - BP[CONV\{(M/2) \times DF(j+M,n)\}]$$

Next, $$H1M \times \{IRPA(j+1) - IRPA(j)\} = \quad (70)$$
$$BP[CONV\{H1M \times RPE(j+(M/2),n)\}] -$$
$$BP[CONV\{H1M \times RPE(j,n)\}]$$

Next, $$(1/2) \times \{IRMA(j+1) - IRMA(j)\} = \quad (71)$$
$$BP[CONV\{(1/2) \times RMF(j+M,n)\}] -$$
$$BP[CONV\{(1/2) \times RMF(j+(M/2),n)\}]$$

Since $RMF(j,n)$ and $RMF(j+M,n)$ have the same projection angle, the following Eq. is obtained:

$$H1M \times \{IRPA(j+1) - IRPA(j)\} + \quad (72)$$
$$(1/2) \times \{IRMA(j+1) - IRMA(j)\} =$$
$$BP[CONV\{H1M \times RPE(j+(M/2),n) -$$
$$(1/2) \times RMF(j+(M/2),n)\}] +$$
$$BP[CONV\{(1/2) \times RMF(j+M) - H1M \times RPE(j)\}]$$

Furthermore, $$IRPK(j+1) - IRPK(j) = \quad (72)$$
$$-IRPA(j) + BP[CONV\{(M/2) \times RPE(j+(M/2),n)\}]$$

Note that $IRPA(j+1)$ is given by:

$$IRPA(j+1) = IRPA(j) - BP[CONV\{RPE(j,n)\}] + \quad (74)$$
$$BP[CONV\{RPE(j+(M/2),n)\}]$$

Next, $$IRMK(j+1) - IRMK(j) = -IRMA(j) + BP[CONV\{(M/2) = \quad (75)$$
$$RMF(j+M,n)\}]$$

Note that $IRMA(j+1)$ is given by:

$$IRMA(j+1) = IRMA(j) - \quad (76)$$
$$BP[CONV\{RMF(j+(M/2),n)\}] +$$
$$BP[CONV\{RMF(j+M,n)\}]$$

Here, we define:

$$IPMA(j) = IRPA(j) - IRMA(j) \quad (77)$$

From this definition, the following Eq. is obtained:

$$IPMA(j+1) = IPMA(j) - BP[CONV\{RPE(j,n)\}] + \quad (78)$$
$$BP[CONV\{RPE(j+(M/2),n)\}] +$$
$$BP[CONV\{RMF(j+(M/2),n)\}] -$$
$$BP[CONV\{RMF(j+M,n)\}]$$

Since $RPE(j,n)$ and $RMF(j+M,n)$ have the same projection angle, Eq. (78) is modified as:

$$IPMA(j+1) = \quad (79)$$
$$IPMA(j) - BP[CONV\{RPE(j,n) + RMF(j+M,n)\}] +$$
$$BP[CONV\{RPE(j+(M/2),n) + RMF(j+(M/2),n)\}]$$

Therefore, $$-\{IRPK(j+1) - IRPK(j)\} + \quad (80)$$
$$\{IRMK(j+1) - IRMK(j)\} = IPMA(j) -$$
$$BP[CONV\{(M/2) \times RPE(j+(M/2),n)\}] +$$
$$BP[CONV\{(M/2) \times RMF(j+M,n)\}]$$

Therefore, when Eqs. (61), (69), (72), and (80) are substituted in Eq. (58), the subtraction image $\Delta(j+1)$ between the $(j+1)$-th and j-th images is obtained as follows:

$$\begin{aligned}
\Delta I(j+1) = \ & BP[CONV\{H3N(n) \times \\
& DF(j+M,n) - H2N(n) \times DE(j,n)\}] + \\
& BP[CONV\{H2N(n) \times \\
& DE(j+(M/2),n) - H3N(n) \times \\
& DF(j+(M/2),n)\}] - \\
& IEFA(j) + BP[CONV\{(M/2) \times \\
& DE(j+(M/2),n)\}] - BP[CONV\{(M/2) \times \\
& DF(j+M,n)\}] + \\
& BP[CONV\{H1M \times RMF(j+ \\
& (M/2),n)\}] - (1/2) \times RMF(j(M/2),n)\}] - \\
& BP[CONV\{(1/2) \times RMF(j+M,n) + \\
& H1M \times RPE(j,n)\}] + IPMA(j) - \\
& BP[CONV\{(M/2) \times RPE(j+(M/2),n)\}] + \\
& BP[CONV\{(M/2) \times RMF(j+M,n)\}]
\end{aligned} \quad (81)$$

Summing over the same projection angle, Eq. (81) is modified as:

$$\begin{aligned}
\Delta I(j+1) = \ & BP[CONV\{H3N(n) \times \\
& DF(j+M,n) - H2N(n) \times \\
& DE(j,n) - (M/2) \times \\
& DF(j+M,n) - ((1/2) - (M/2)) \times \\
& RMF(j+M,n) - H1M \times \\
& RPE(j,n)\}] + BP[CONV\{H2N(n) \times \\
& DE(j+(M/2),n) - \\
& H3N(n) \times DF(j+(M/2),n) + \\
& (M/2) \times DE(j+(M/2),n) + \\
& H1M \times RPE(j+(M/2),n) + \\
& (1/2) \times RMF(j+(M/2),n) - \\
& (M/2) \times RPE(j+(M/2),n)\}] + \\
& IPMA(j) - IEFA(j) \\
= \ & BP[CONV\{(H3N(n) - (1/2)) \times \\
& DF(j+M,n) - H2N(n) \times DE(j,n) + \\
& ((M-1)/2) \times RMF(j+M,n) - \\
& H1M \times RPE(j,n)\}] + BP[CONV\{(H2N(n) + \\
& (M/2)) \times DE(j+(M/2),n) - \\
& H3N(n) \times DF(j+(M/2),n) + \\
& (1/2) \times RPE(j+(M/2),n) + \\
& RMF(j+(M/2),n)\}] + IPMA(j) - IEFA(j)
\end{aligned} \quad (82)$$

If we define:

$$IB(j) = IPMA(j) - IEFA(j) \quad (83)$$

then the $\Delta(j+1)$ image is given by:

$$\begin{aligned}
\Delta I(j+1) = \ & BP[CONV\{-H2N(n) \times \\
& (DF(j+M,n) + DE(j,n)) + \\
& ((M-1)/2) \times RMF(j+M,n)\} - \\
& H1M \times RPE(j,n)\}] + \\
& BP[CONV\{H2N(n) + (M/2)) \times \\
& DE(j+(M/2),n) - \\
& H3N(n) \times DF(j+(M/2),n) + \\
& (1/2) \times (RPE(j+(M/2),n) + \\
& RMF(j+(M/2),n)\}] + IB(j)
\end{aligned} \quad (84)$$

From Eqs. (83), (79), and (68), IB(j+1) is given by:

$$\begin{aligned}
IB(j+1) = \ & IPMA(j+1) - IEFA(j+1) \\
= \ & IPMA(j) - \\
& BP[CONV\{RPE(j,n) + RMF(j+M,n)\}] + \\
& BP[CONV\{RPE(j+(M/2),n) + \\
& RMF(j+(M/2),n)\}] - \\
& IEFA(j) + \\
& BP[CONV\{DE(j,n) + DF(j+M,n)\}] - \\
& BP[CONV\{DE(j+(M/2),n) + \\
& DF(j+(M/2),n)\}] \\
= \ & IB(j) - \\
& BP[CONV\{-DE(j,n) + \\
& RPE(j,n) - DF(j+M,n) + RMF(j+M,n)\}] + \\
& BP[CONV\{-DE(j+(M/2),n) + \\
& RPE(j+(M/2),n) - \\
& DF(j+(M/2),n) + RMF(j+(M/2),n)\}]
\end{aligned} \quad (85)$$

Note that IB(j) is given by:

$$\begin{aligned}
IB(j) = \ & IPMA(j) - IEFA(j) \\
= \ & IRPA(j) - IRMA(j) - IEA(j) + IFA(j) \\
= \ & BP[CONV\{RPEU(j)\}] - BP[CONV\{RMFU(j)\}] - \\
& BP[CONV\{DEU(j)\}] + BP[CONV\{DFU(j)\}] \\
= \ & BP[CONV\{DERPU(j)\}] - BP[CONV\{DERMU(j)\}]
\end{aligned} \quad (86)$$

where

DERPU(j): a set of $RPE(k+j-1,n) - DE(k+j-1,n)$
where $k=1$ to $M/2$

DERMU(j): a set of $RMF(k+j-1,n) - DF(k+j-1,n)$
where $k=M/2+1$ to $M$ when j is replaced by $j-1$, Eq. (84) is modified as:

$$\begin{aligned}
\Delta I(j) = \ & I(j) - I(j-1) \\
= \ & BP[CONV\{-H2N(n) \times \\
& (DF(j+M-1,n) + DE(j-1,n)) + \\
& ((M-1)/2) \times \\
& RMF(j+M-1,n) - H1M \times RPE(j-1,n)\}] + \\
& BP[CONV\{(H2N(n) + (M/2)) \times \\
& DE(j+(M/2)-1,n) - \\
& H3N(n) \times DF(j+(M/2)-1,n) + \\
& (1/2) \times (RPE(j+(M/2)-1,n) + \\
& RMF(j+(M/2)-1,n))\}] + \\
& IB(j-1)
\end{aligned} \quad (88)$$

Equation (85) is further modified as follows:

$$\begin{aligned}
IB(j) = \ & IB(j+1) + \\
& BP[CONV\{-DE(j,n) + RPE(j,n) - \\
& DF(j+M,n) + RMF(j+M,n)\}] - \\
& BP[CONV\{-DE(j+(M/2),n) + \\
& RPE(j+(M/2),n) - \\
& DF(j+(M/2),n) + RMF(j+(M/2),n)\}]
\end{aligned} \quad (89)$$

When j is replace by j−1, Eq. (89) can be modified as:

$$\begin{aligned}IB(j-1) = \ &IB(j) + \\ &BP\ [CONV\ \{-DE(j-1,n) + RPE(j-1,n) - \\ &DF(j+M-1,n) + RMF(j+M-1,n)\}] - \\ &BP\ [CONV\ \{-DE(j+(M/2)-1,n) + \\ &RPE(j+(M/2)-1,n) - \\ &DF(j+(M/2)-1,n) + \\ &RMF(j+(M/2)-1,n)\}]\end{aligned} \quad (90)$$

As can be understood from the above description, an image adjacent to the already reconstructed image I(j) can be continuously reconstructed using Eqs. (84) and (88). Equation (55a) for obtaining the j-th image I(j) requires M number of CONV calculations and M number of BP calculations. Each of Eqs. (84) and (88) for obtaining the subtraction image ΔI requires two CONV calculations and two BP calculations. However, in order to continuously reconstruct images, IB(j+1) or IB(j−1) must be obtained. IB(j+1) is obtained by Eq. (85), or IB(j−1) is obtained by Eq. (90). Each of Eqs. (85) and (90) requires two CONV calculations and two BP calculations. Therefore, in order to continuously obtain I(j+1) or I(j−1), four CONV calculations and four BP calculations are required.

An amount of calculation other than CONV and BP calculations is very small as compared to that of CONV and BP calculations. Therefore, the total amount of calculation is almost determined by the number of CONV and BP calculations. In general, since the number "M" is considerably larger than 4, reconstruction using Eqs. (84) and (88) has a very small amount of calculation as compared to Eq. (55a).

The above description is complicated since all modifications of Eqs. are presented. Only Eqs. associated with the principle of continuous reconstruction according to the present invention will be summarized below. The numbers of the Eqs. used in the above description are presented below on the left-hand side of "/", and renumbered numbers are presented on the right-hand side of "/" for the purpose of arrangement.

fan angle: $2\alpha$
number of data per view: N (even number)
$\Delta\alpha = 2\alpha/N$
angle between two adjacent views: $\Delta\theta$
number of views per 360°: M (even number)
$M \times \Delta\theta = 360°$
view number: m
projection data: D(m,n)
projection angle of m-th view: $m \times \Delta\theta$
gantry moving distance (between adjacent views): d
position of m-th view: $m \times d$
total number of scanned views: MM $$aa = \Delta\alpha/\Delta\theta \quad (6)/(91)$$

$$nn = N+1-n \quad (3)/(92)$$

$$mp = m + M/2 - (N+1-2n) \times aa \quad (4)/(93)$$

$$mm = m - M/2 - (N+1-2n) \times aa \quad (5)/(94)$$

ci: an integral part of $(N-1) \times aa$
cp: a decimal part of $(N-1) \times aa$
mpi: an integral part of mp
mpp: a decimal part of mp
mmi: an integral part of mm
mmp: a decimal part of mm $$mmr = mr + ci + 1 - (N+1-2n) \times aa \quad (15)/(95)$$

mmri: an integral part of mmr
mmrp: a decimal part of mmr $$R(mr,n) = D(mmri,nn) \times (1-mmrp) + D(mmri+1,nn) \times mmrp \quad (16)/(96)$$

for mr=1 to MM−2ci−2

$$RP(m,n) = R\{m+(M/2)-ci-1,n\} \quad (13)/(97)$$

$$RM(m,n) = R\{m-(M/2)-ci-1,n\} \quad (14)/(98)$$

$$H1(k) = \{(M+1)/2\} - k \quad (30)/(99)$$

for k=1 to M $$H2(k,n) = k - \tfrac{1}{2} - (N+1-2n) \times aa \quad (31)/(100)$$

for k=1 to M/2

$$H3(k,n) = M - \{(k-1)/2\} - (N+1-2n) \times aa \quad (32)/(101)$$

for k= M/2+1 to M $$H4(n) = M/2 - (N+1-2n) \times aa \quad (33)/(102)$$

$$H5(n) = M/2 + (N+1-2n) \times aa \quad (34)/(103)$$

$$DE(m,n) = D(m,n)/H4(n) \quad (35)/(104)$$

$$DF(m,n) = D(m,n)/H5(n) \quad (36)/(105)$$

$$RPE(m,n) = RP(m,n)/H4(n) \quad (37)/(106)$$

$$RMF(m,n) = RM(m,n)/H5(n) \quad (38)/(107)$$

$$H1M = (M+1)/2 \quad (39)/(108)$$

$$H2N(n) = -\tfrac{1}{2} - (N+1-2n) \times aa \quad (40a)/(109)$$

$$H3N(n) = M/2 + \tfrac{1}{2} + (N+1-2n) \times aa \quad (40b)/(110)$$

$$\begin{aligned}I(j) = \ &BP\ [CONV\ \{H2(k,n) \times \\ &DE(k+j-1) + H1(k) \times RPE(k+j-1,n)\}] \\ = \ &BP\ [CONV\ \{H3(k+(M/2),n) \times \\ &DF(k+j-1+(M/2),n) - \\ &H1(k+(M/2)) \times RMF(k+j-1+(M/2),n)\}]\end{aligned} \quad (111)$$

for k=1 to M/2

$$\begin{aligned}IB(j) = \ &BP[CONV\{RPE(k+j-1,n) - DE(k+j-1,n)\}] + \\ &BP\ [CONV\ \{RMF(k+j+(M/2)-1,n) - \\ &DF(k+j+(M/2)-1,n)\}]\end{aligned} \quad (112)$$

for k=1 to M/2

$$\begin{aligned}IB(j+1) = \ &IB(j) - BP\ [CONV\ \{-DE(j,n) + RPE(j,n) - \\ &DF(j+M,n) + RMF(j+M,n)\}] + \\ &BP\ [CONV\ \{-DE(j+(M/2),n) + RPE(j+(M/2),n) - \\ &DF(j+(M/2),n) + RMF(j+(M/2),n)\}]\end{aligned} \quad (85)/(113)$$

$$\begin{aligned}IB(j-1) = \ &IB(j) + BP\ [CONV\ \{-DE(j-1,n) + RPE(j-1,n) - \\ &DF(j+M-1,n) + RMF(j+M-1,n)\}] +\end{aligned} \quad (90)/(114)$$

-continued
$$BP\ [CONV\ \{-DE(j+(M/2)-1,n)+\\ RPE(j+(M/2)-1,n)-\\ DF(j+(M/2)-1,n)+RMF(j+(M/2)-1,n)\}]$$

$$I(j+1)=I(j)+\Delta I(j+1) \quad (114a)$$

$$\Delta I(j+1)= \quad (84)/(115)$$

$$BP\ [CONV\ \{-H2N(n)\times(DF(j+M,n)+DE(j,n))+\\ ((M-1)/2)\times RMF(j+M,n)\}-H1M\times RPE(j,n)\}]+\\ BP\ [CONV\ \{H2N(n)+(M/2)\times DE(j+(M/2),n)-\\ H3N(n)\times DF(j(M/2),n)+(1/2)\times\\ (RPE(j+(M/2),n)+RMF(j+(M/2),n)\}]+IB(j)$$

$$I(j-1)=I(j)-\Delta I(j) \quad (115a)$$

$$\Delta I(j)= \quad (88)/(116)$$

$$BP\ [CONV\ \{-H2N(n)\times(DF(j+M-1,n)+DE(j-1,n))+\\ ((M-1)/2)\times RMF(j+M-1,n)-H1M\times RPE(j-1,n)\}]+\\ BP\ [CONV\ \{(H2N(n)+(M/2))\times DE(j+(M/2)-1,n)-\\ H3N(n)\times DF(j+(M/2)-1,n)+(1/2)\times\\ (RPE(j+(M/2)-1,n)+RMF(j+(M/2)-1n)\}]+IB(j-1)$$

The arrangement of a CT apparatus according to the first embodiment of the present invention based on the above-mentioned principle will be described hereinafter. FIG. 10 is a block diagram showing a schematic arrangement according to the first embodiment of the present invention. A fan beam radiated from an X-ray tube 10 and transmitted through an object 12 to be examined is detected by a detector array 14, and is input to a data acquisition system 16. Projection data acquired by the data acquisition system 16 are supplied to an image reconstruction unit 18 and is subjected to a reconstruction processing. A CT image reconstructed by the image reconstruction unit 18 is displayed on a display 20, and is stored in an image memory 22. The data acquisition system 16, the image reconstruction unit 18, the display 20, and the image memory 22 are connected to each other via a bus line 24. A console 26 from which various instructions are input by an operator is connected to the bus line 24. Note that the overall operation is controlled by a computer (not shown).

Figure 11:
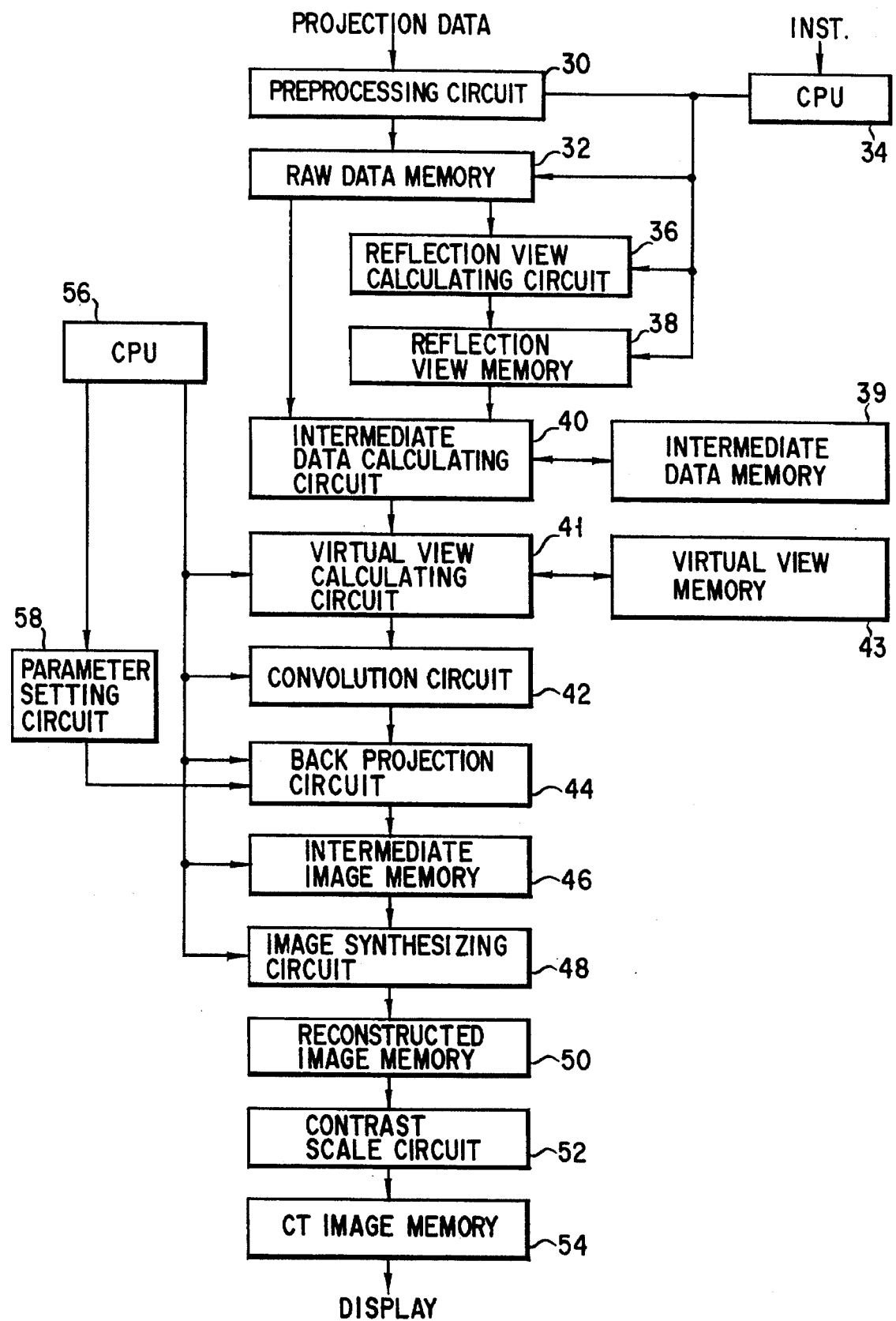
FIG. 11 is a block diagram showing the details of an image reconstruction unit shown in FIG. 10.

FIG. 11 is a block diagram showing a schematic arrangement of the image reconstruction unit 18 shown in FIG. 10. Projection data are supplied to a preprocessing circuit 30, and an output from the preprocessing circuit 30 is stored in a raw data memory 32. A reflection view calculating circuit 36 calculates a reflection view on the basis of the output from the raw data memory 32, and stores the reflection view in a reflection view memory 38. The raw data memory 32, the reflection view calculating circuit 36, and the reflection view memory 38 are controlled by a CPU 34. The CPU 34 receives instructions from the console 26.

The outputs from the raw data memory 32 and the reflection view memory 38 are supplied to an intermediate data calculating circuit 40, and intermediate data is calculated on the basis of the above-mentioned Eqs. (104) to (107). The intermediate data calculating circuit 40 is connected to an intermediate data memory 39.

The intermediate data is supplied to a virtual view calculating circuit 41, and a virtual view is calculated on the basis of the CONV calculations included in the above-mentioned Eqs. (111) to (116). The virtual view calculating circuit 41 is connected to a virtual view memory 43. The virtual view is supplied to a convolution (CONV) circuit 42. The output from the CONV circuit 42 is supplied to an intermediate image memory 46 via a back projection (BP) circuit 44. The output from the intermediate image memory 46 is supplied to an image synthesizing circuit 48, thus reconstructing an image.

The reconstructed image is supplied to a reconstructed image memory 50. The virtual view calculating circuit 41, the CONV circuit 42, the BP circuit 44, the intermediate image memory 46, and the image synthesizing circuit 48 are controlled by a CPU 56. A parameter setting circuit 58 is connected to the BP circuit 44. The output from the reconstructed image memory 50 is supplied to a CT image memory 54 via a contrast scale circuit 52.

Figure 12:
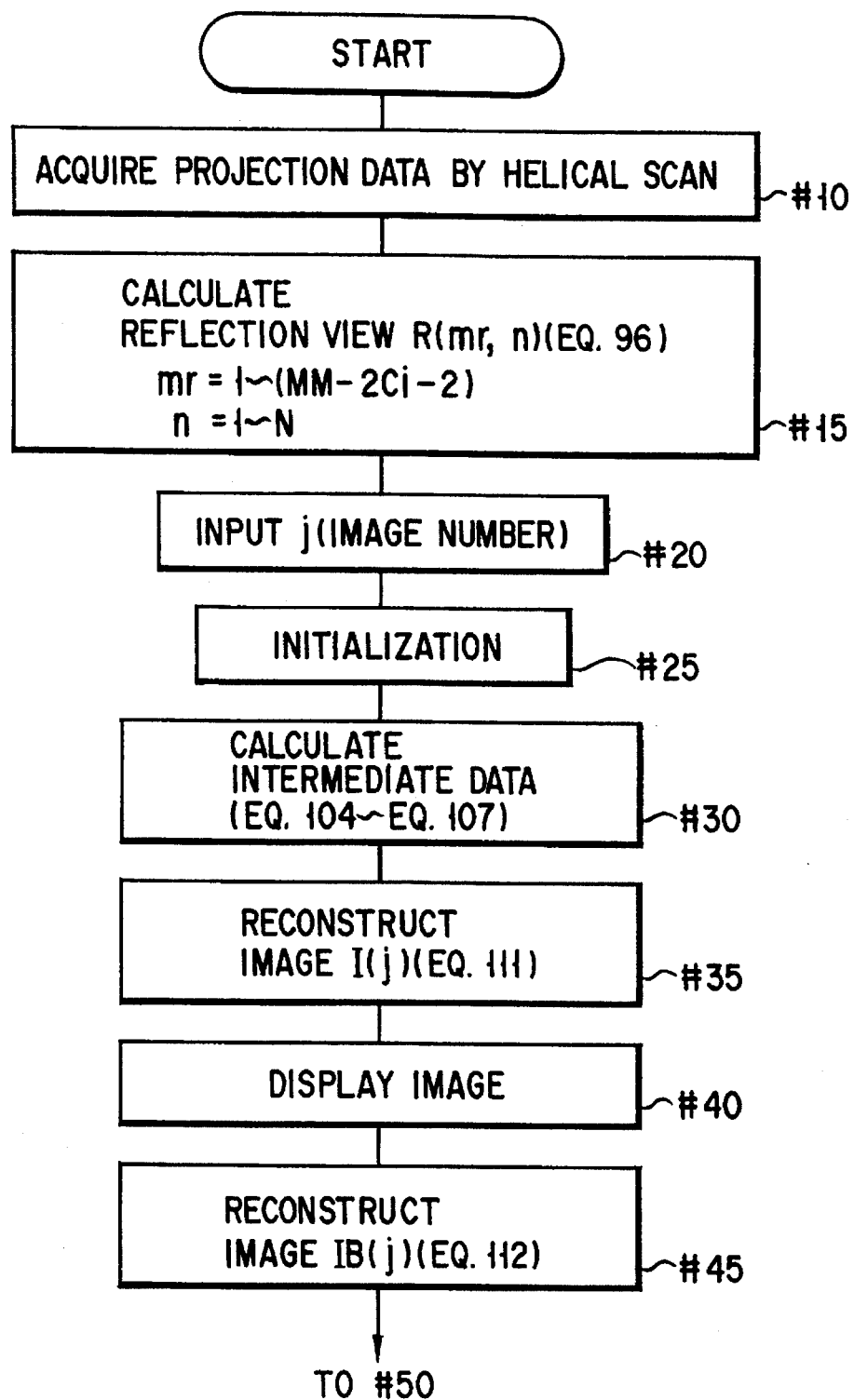
FIG. 12 is a flow chart showing a first part of an operation according to the first embodiment of the present invention.
Figure 13:
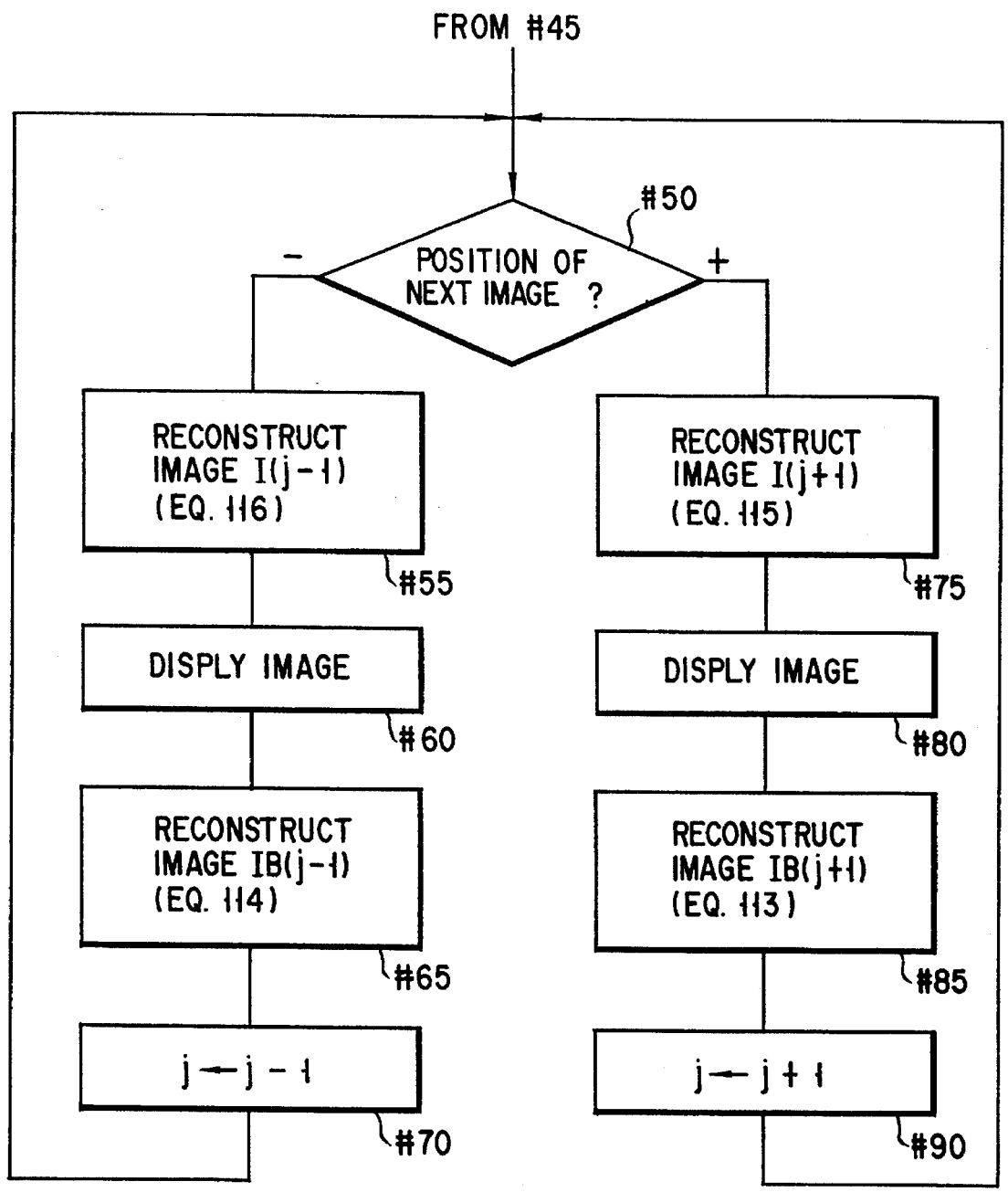
FIG. 13 is a flow chart showing a second part of the operation of the first embodiment of the present invention.

The operation of the first embodiment will be described below with reference to the flow charts shown in FIGS. 12 and 13.

In step #10, a helical scan is performed to acquire projection data. The projection data are preprocessed by the preprocessing circuit 30, and the preprocessed data are stored in the raw data memory 32. Upon completion of the scan or after a predetermined amount of raw data are acquired, reflection beam data (reflection view data) R(mr,n) are calculated based on Eq. (96), and are stored in the reflection view memory 38 in step #15.

In step #20, a number "j" of an image to be reconstructed is designated.

In step #25, necessary initialization is executed.

In step #30, DE(m,n), DF(m,n), RPE(m,n), and RMF(m,n) are calculated for m=1 to MM−2ci−2 and n=1 to N on the basis of Eqs. (104) to (107), and these data are stored in the intermediate data memory 39.

In step #35, a j-th image I(j) is reconstructed based on Eq. (111).

In step #40, the reconstructed image is displayed.

In step #45, an image IB(j) is reconstructed based on Eq. (112).

In step #50, the position of the next image to be reconstructed is discriminated. The position is selected by instructing the change direction of "j" (image number) using, e.g., a three-point switch. If the switch is set at the neutral position, the control waits until either direction is instructed. If it is instructed to change "j" in the minus direction, the flow advances to step #55; if it is instructed to change "j" in the plus direction, the flow advances to step #75.

If the minus direction is selected in step #50, the immediately preceding image I(j−1) is reconstructed using Eqs. (115a) and (116) in step #55.

In step #60, the image I(j−1) reconstructed in step #55 is displayed.

In step #65, an image IB(j−1) is reconstructed based on Eq. (114).

In step #70, "j" is decremented by 1, and the flow returns to step #50.

If the plus direction is selected in step #50, the next image I(j+1) is reconstructed using Eqs. (114a) and (115) in step #75.

In step #80, the image I(j+1) reconstructed in step #75 is displayed.

In step #85, an image IB(j+1) is reconstructed based on Eq. (113).

In step #90, "j" is incremented by 1, and the flow returns to step #50.

Upon repetition of the above-mentioned operation, adjacent images are continuously reconstructed using Eq. (116) or (115) while continuously changing "j". The change direction of "j" may be changed in step #50 or a change in "j" may be ended.

As described above, according to the first embodiment, the first tomographic image is normally reconstructed by executing convolution and back projection calculations of a virtual view obtained by interpolation and/or extrapolation using projection data and their reflection beam data in a range of 360°+a double fan angle 4α before and after the slice position. However, a tomographic image adjacent to the first image is reconstructed in such a manner that a subtraction image is calculated by executing convolution and back projection calculations of a difference between data used in reconstruction of the first tomographic image and data necessary for normally reconstructing a current tomographic image to be reconstructed, and the subtraction image is synthesized (added) to the already reconstructed tomographic image. Therefore, a large number of tomographic images can be reconstructed within a short period of time, and a large number of images whose slice positions are shifted from each other can be continuously reconstructed.

A modification of the first embodiment will be described below. In the first embodiment, as shown in Eqs. (115) and (116), a tomographic image adjacent to the already reconstructed tomographic image is reconstructed in such a manner that a subtraction image is calculated by executing convolution and back projection calculations of a difference between data used in reconstruction of the already reconstructed tomographic image and data necessary for normally reconstructing a current tomographic image to be reconstructed, and the subtraction image is synthesized with the already reconstructed tomographic image. However, the subtraction image need not always be calculated. More specifically, the difference between data used in reconstruction of the already reconstructed tomographic image and data necessary for normally reconstructing a current tomographic image to be reconstructed may be superposed on the already reconstructed tomographic image, and the superposed result may be subjected to convolution and back projection calculations to calculate the current tomographic image. In this case, (j−1)th and (j+1)th images are expressed as follows:

$$I(j+1) = I(j) + \qquad (117)$$
$$BP\ [CONV\ \{-H2N(n) \times (DF(j+M,n) + DE(j,n)) + ((M-1)/2) \times RMF(J+M,n) - H1M \times RPE(j,n))] +$$
$$BP\ [CONV\ \{(H2N(n) + (M/2) \times DE(j+(M/2),n) - H3N(n) \times DF(j+(M/2),n) + (1/2) \times (RPE\ (j+ (M/2),n) + RMF(j+(M/2),n)\}] + IB(j)$$

$$I(j-1) = I(j) + \qquad (118)$$
$$BP\ [CONV\ \{-H2N(n) \times (DF(j+M-1,n) + DE(j-1,n)) + ((M-1)/2) \times RMF(j+M-1,n) - H1M \times RPE(j-1,n))] +$$
$$BP\ [CONV\ \{(H2N(n) + (M/2) \times DE(j+(M/2)-1,n) - H3N(n) \times DF(j+(M/2)-1,n) + (1/2) \times (RPE\ (j+ (M/2)-1,n) + RMF(j+(M/2)-1,n)\}] + IB(j)$$

In the above embodiment, all reflection views are calculated prior to reconstruction. However, reflection views may be calculated as needed. Furthermore, when the channel positions are asymmetrical with the center line, substantially the same operation as in the first embodiment can be executed, except for an interpolation or extrapolation method (for example, reflection data more than two data, e.g., four data, are interpolated or extrapolation upon calculation of reflection views).

Other embodiments of the present invention will be described below. In other embodiments, if the apparatus arrangement is the same as that in the first embodiment, a detailed description thereof will be omitted, and its operation alone will be described. In the description of the operation, a description of the same portions as those in the first embodiment will be omitted.

In the first embodiment, adjacent images are sequentially reconstructed, and are sequentially displayed. Alternatively, a display operation may be performed in units of a plurality of "n" images. The second embodiment for executing this operation will be described below.

Figure 14:
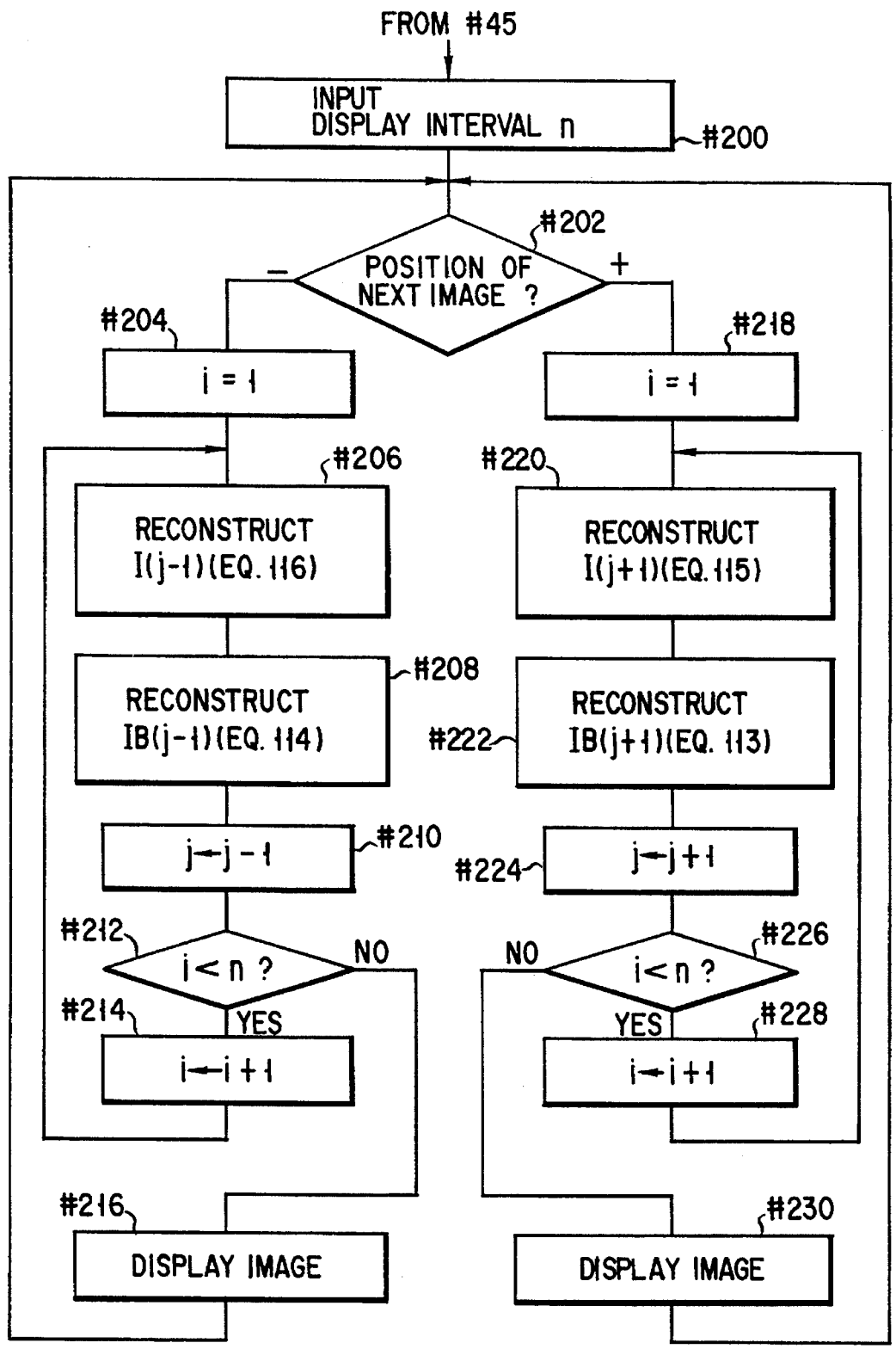
FIG. 14 is a flow chart showing an operation according to a second embodiment of the present invention.

FIG. 14 is a flow chart of the second embodiment. Since the operation up to step #45 (i.e., the j-th image I(j) is reconstructed and displayed, and an image IB(j) is reconstructed) is the same as that in the first embodiment, steps associated with the operation are not shown.

In step #200, a display image interval "n" (n≧1) is input.

If the minus direction is instructed in step #202, i=1 is set in step #204, a (j−1)th image is reconstructed using Eq. (116) in step #206, an image IB(j−1) is reconstructed using Eq. (114) in step #208, and "j" is decremented by 1 in step #210. In step #212, it is checked if i<n. If i<n, "i" is incremented by 1 in step #214, and the flow returns to step #206; otherwise, a finally reconstructed image is displayed in step #216, and the flow returns to step #202.

If the plus direction is instructed in step #202, i=1 is set in step #218, a (j+1)th image is reconstructed using Eq. (115) in step #220, an image IB(j+1) is reconstructed using Eq. (113) in step #222, and "j" is incremented by 1 in step #224. In step #226, it is checked if i<n. If i<n, "i" is incremented by 1 in step #228, and the flow returns to step #220; otherwise, a finally reconstructed image is displayed in step #230, and the flow returns to step #202.

The third embodiment will be described below. In the second embodiment, tomographic images are calculated in steps #206 and #208 or steps #220 and #222 independently of whether or not images are displayed. A (j+n)th image is expressed as follows from Eq. (114a):

$$I(j+n) = I(j) + \sum_{i=1}^{n} \Delta I(j+i) \qquad (120)$$

Similarly, a (j−n)th image is expressed as follows from Eq. (115a):

$$I(j-n) = I(j) - \sum_{i=1}^{n} \Delta I(j+1-i) \qquad (121)$$

Therefore, in step #206 in the second embodiment shown in FIG. 14, in place of calculating the (j−1)th image using Eq. (116), only the second term of the right-hand side of Eq. (121) may be calculated, and step of calculating the (j−n)th image by adding the second term of the right-hand side of Eq. (121) to the j-th image may be added before image displaying step #216. Similarly, in step #220, in place of calculating the (j+1)th image using Eq. (115), only the second term of the right-hand side of Eq. (120) may be calculated, and step of calculating the (j+n)th image by adding the second term of the right-hand side of Eq. (120) to the j-th image may be added before image displaying step #230.

Figure 15:
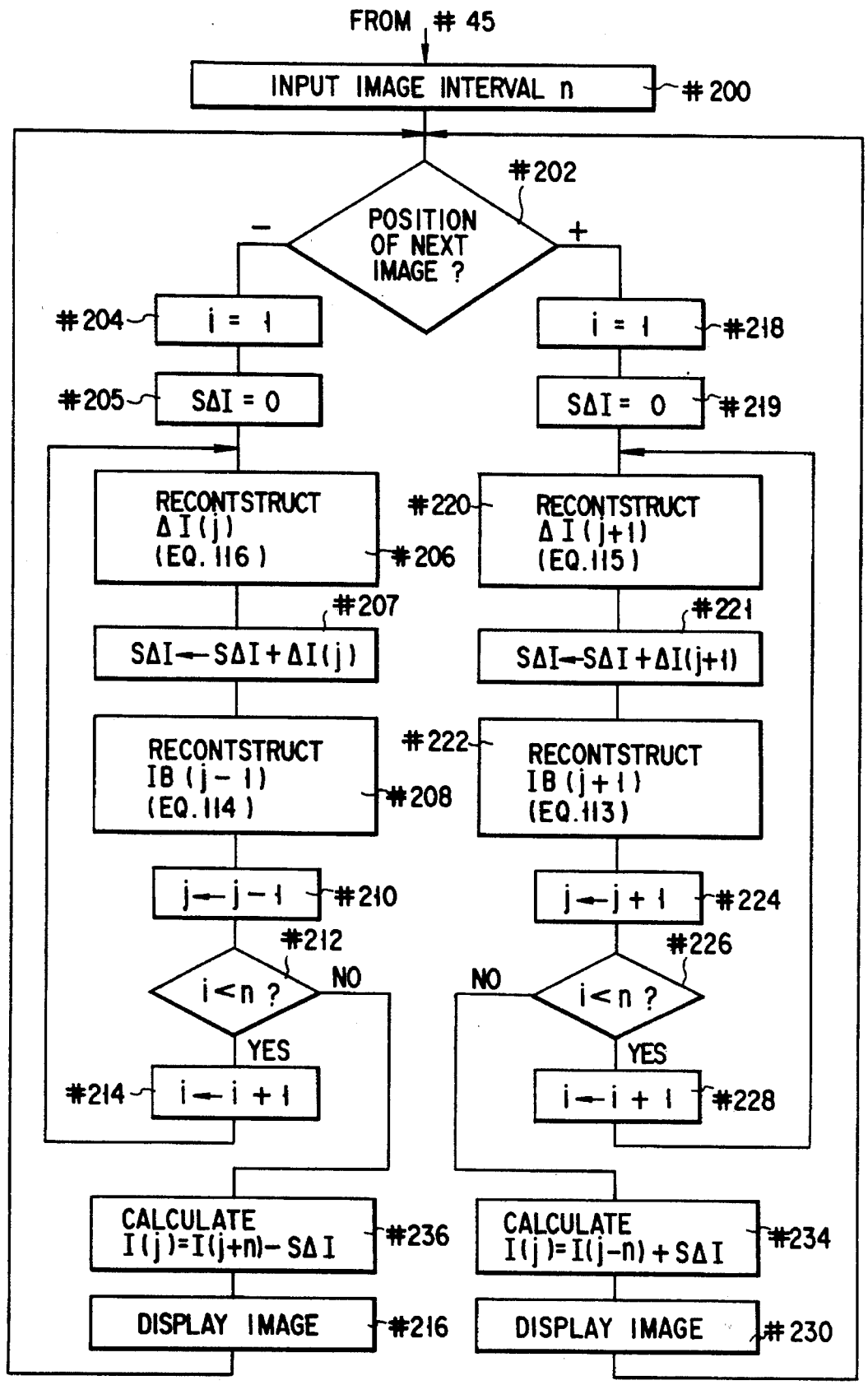
FIG. 15 is a flow chart showing an operation according to a third embodiment of the present invention.

FIG. 15 is a flow chart of the third embodiment including the above-mentioned calculations. More specifically, ΣΔI(j+i) is calculated in step #221, ΣΔI(j+1−i) is calculated in step #207, after initialing at steps #219 and #205 respectively, step #234 of calculating I(j+n) using Eq. (120) is added before step #230, and step #236 of calculating I(j−n) using Eq. (121) is added before step #216.

In each of the above embodiments, the image number is sequentially changed by selecting the direction of change using a three-position switch. Alternatively, a desired image number may be input by means of a pointer such as a mouse, a track ball, or the like. In this case, in place of step #50 of the first embodiment or step #202 of the second or third embodiment, a signal from a pointer such as a mouse is read, and if the signal does not change, the control waits in step #50 or #202. If the signal changes, the number "n" of images to be displayed is calculated by multiplying an amount of change with a predetermined coefficient. If n>0, the process in the plus direction is executed; if n<0, the process in the minus direction is executed.

In each of the above embodiments, the reconstructed image is displayed but is not stored in the image memory 22 since a huge memory capacity is required to store all images. Alternatively, all images may be reconstructed, and only designated images may be stored in the image memory 22.

Furthermore, in place of storing a reconstructed image itself, a time curve may be calculated and stored. The time curve represents a change in a CT value (average value) of a certain portion (region of interest) over time.

In each of the above embodiments, the method of performing continuous reconstruction using views in a range of 360°+a double fan angle 4α obtained by a helical scan in the third generation X-ray CT apparatus of the R/R (Rotate/Rotate) system has been described. A fourth embodiment related to a helical scan reconstruction method in a so-called fourth generation X-ray CT apparatus of an S/R (Stationary/Rotate) system (a stationary detector array is used, and an X-ray tube alone is rotated) will be described below.

Figure 16:
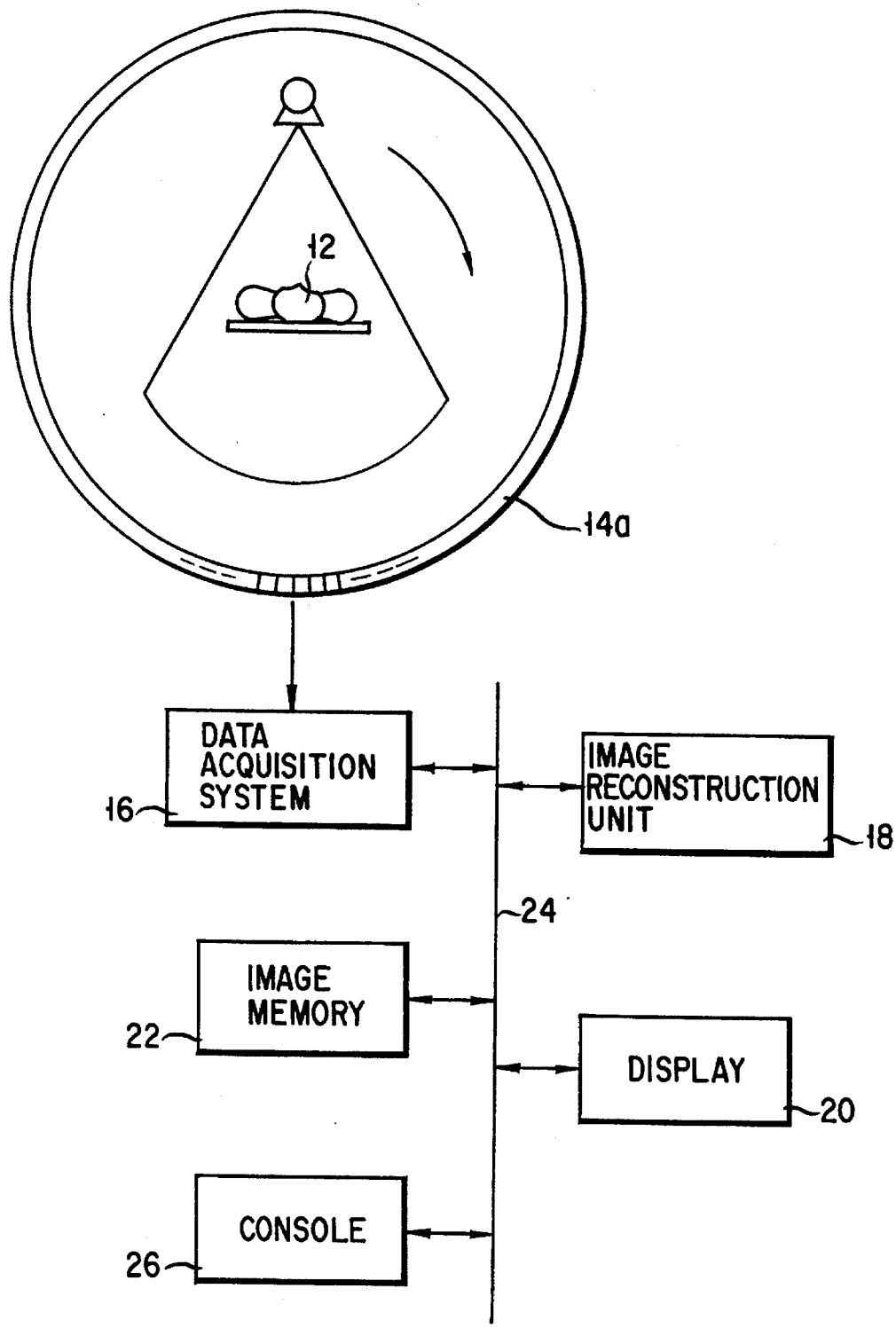
FIG. 16 is a block diagram showing a computed tomography apparatus according to a fourth embodiment of the present invention.

FIG. 16 shows the apparatus arrangement of the fourth embodiment. The arrangement of the fourth embodiment is substantially the same as that of the first embodiment shown in FIG. 10, except that a detector array 14a is arranged throughout 360° and is fixed in position, and an X-ray tube 10, which rotates inside or outside the detector array 14a, is arranged. Thus, a detailed description thereof will be omitted. More specifically, the details of the image reconstruction unit 18 are the same as those shown in FIG. 11.

In the R/R system, reconstruction is performed using a source fan as it is. However, in the S/R system, reconstruction is normally performed using a detector fan in order to improve spatial resolution. The source fan is fan data having the X-ray tube as the center of a fan. The detector fan is fan data having the detectors (channels) as the center of a fan. Therefore, raw data in the S/R system is the detector fan. Therefore, the source fan must be converted into the detector fan. This conversion is executed by the preprocessing circuit 30 shown in FIG. 11. In the fixed position scan, either the R/R system or the S/R system performs the same reconstruction processes after raw data. However, in the helical scan, the S/R system requires a complicated interpolation or extrapolation as compared to the R/R system described in the first embodiment. In the following description, assume that projection data is the detector fan unless otherwise specified.

As in the first embodiment, projection data is defined as follows. Assume that projection data is symmetrical about the center line connecting a detector as the center of the detector fan and the center of rotation. However, the present invention can be almost similarly practiced even when projection data is asymmetrical with the center line.

If the fan angle of a fan beam is represented by 2α, and the number of channels (the number of detectors) of the detector array for detecting the fan beam is represented by N (even number), the fan angle Δα per channel is given by Δα=2α/N. If the rotational angle of an X-ray beam between adjacent views is represented by Δθ, and the number of views per 360° is represented by M (even number), M×Δθ= 360°. The view number is represented by "m", the channel number is represented by "n", and the projection data is represented by D(m,n). The angle defined by the center line of an m-th view is referred to as a projection angle. The projection angle of the m-th view is m×Δθ.

If we let "e" be the moving distance between adjacent projections of the source fan, and "g" be the number of views per 360° of the source fan/M (the number of views per 360° of the detector fan), the position of n-th data of an m-th view of the detector fan is given by m×g×e+n×e, and the total number of scanned views is represented by MM.

Since reflection beams are the same as those in the first embodiment, virtual projection data is expressed by the following Eq. used in the description of the first embodiment. The same Eq. numbers are assigned to the same Eqs. as in the first embodiment, and a description thereof will be omitted.

$$DD(m,n) = \quad (18)$$

$$[D(m,n) \times \{RPP(m,n) - SP\} + RP(m,n) \times$$

$$\{SP - DP(m,n)\}]/\{RPP(m,n) - DP(m,n)\}$$

A slice position SP of the detector fan is given by:

$$SP=\{j+(M-1)/2\}\times g\times e+\{(N+1)/2\}\times e \quad (420)$$

For the sake of easy understanding, the following parameter "k" is introduced as in the first embodiment:

$$k=m-j+1 \quad (21)$$

for k=1 to M

Therefore, the view number "m" is given by:

$$m=k+j-1 \quad (22)$$

for m=j to j+M−1

Therefore, the position of projection data (the position of the n-th data of the m-th view of the detector fan) is calculated as follows according to the value of "k":

$$DP(m,n) \quad = \quad m \times g \times e + n \times e \quad (422A)$$
$$= \quad (k+j-1) \times g \times e + n \times e$$

The position of a plus-side reflection beam RP is calculated as follows according to the value of "k":

$$RPP(m,n) \quad = \quad mp \times g \times e + (N+1-n) \times e \quad (422B)$$
$$= \quad \{m + (M/2) - (N+1-2n) \times aa\} \times g \times e +$$
$$(N+1-n) \times e$$

If we define:

$$Nn=N+1-2n \quad (422C)$$

$$Nna=Nn \times aa \quad (422D)$$

then, $$RPP(m,n)=\{K+j-1+(M/2)-Nna\}\times g\times e+(Nn+n)\times e \quad (422E)$$

The position of a minus-side reflection beam RM is calculated as follows according to the value of "k":

$$RMP(m,n) \quad = \quad mm \times g \times e + (N+1-n) \times e \quad (422F)$$
$$= \quad \{m - (M/2) - Nna\} \times g \times e + (Nn+n) \times e$$
$$= \quad \{k+j-1-(M/2) - Nna\} \times g \times e +$$
$$(Nn+n) \times e$$

Therefore,

-continued
$$SP - DP(m,n) = \{j + (M - 1)/2\} \times g \times e + \qquad (423)$$
$$\{(N + 1)/2\} \times e$$
$$(k + j - 1) \times g \times e - n \times e$$
$$= \{(M + 1)/2 - k\} \times g \times e +$$
$$(Nn/2) \times e$$

$$RPP(m,n) - SP = \{k + j - 1 + (M/2) - Nna\} \times \qquad (424)$$
$$g \times e + (Nn + n) \times e -$$
$$\{j + (M - 1)/2\} \times g \times e -$$
$$\{(N + 1)/2\} \times e =$$
$$\{k - (1/2) - Nna\} \times g \times$$
$$e + (Nn/2) \times e$$

$$RPP(m,n) - DP(m,n) = \{k + j - 1 + (M/2) - Nna\} \times \qquad (425)$$
$$g \times e + (Nn + n) \times e -$$
$$(k + j - 1) \times g \times e - n \times e$$
$$= \{(M/2) - Nna\} \times g \times e + Nne$$

$$RMP(m,n) - DP(m,n) = \{k + j - 1 - (M/2) - Nna\}) \times \qquad (426)$$
$$g \times e + (Nn + n) \times e$$
$$= -(k + j - 1) \times g \times e - n \times e$$
$$= -\{(M/2) + Nna\} \times g \times e + Nne$$

Therefore, the virtual view is calculated as follows according to the value of "k":

$$DD(k + j - 1, n) = \qquad (428)$$
$$\{D(k + j - 1, n) \times H42(k,n) + RP(k + j - 1, n) \times$$
$$H41(k,n)\}/H44(n)$$

where k=1 to M/2

$$DD(k + j - 1, n) = \qquad (429)$$
$$\{D(k + j - 1, n) \times H43(k,n) - RM(k + j - 1, n) \times$$
$$H41(k,n)\}/H45(n)$$

where k=M/2+1 to M
Note that H41 to H45 are defined as follows:

$$H41(k,n) = [\{(M+1)/2\} - k] \times g + Nn/2 \qquad (430)$$

$$H42(k,n) = \{k - (\tfrac{1}{2}) - Nna\} \times g + Nn/2 \qquad (431)$$

$$H43(k,n) = \{M - k + (\tfrac{1}{2}) + Nna\} \times g - Nn/2 \qquad (432)$$

$$H44(n) = \{(M/2) - Nna\} \times g + Nn \qquad (433)$$

$$H45(n) = \{(M/2) + Nna\} \times g - Nn \qquad (434)$$

The principle of continous reconstruction will be described below. The following variables are defined in advance:

$$DE(m,n) = D(m,n)/H44(n) \qquad (435)$$

$$DF(m,n) = D(m,n)/H45(n) \qquad (436)$$

$$RPE(m,n) = RP(m,n)/H44(n) \qquad (437)$$

$$RMF(m,n) = RM(m,n)/H45(n) \qquad (438)$$

$$H41N(n) = \{(M+1) \times g + Nn\}/2 \qquad (439)$$

$$H42N(n) = (Nn/2) - \{(\tfrac{1}{2}) + Nna\} \times g \qquad (440a)$$

$$H43N(n) = \{(M/2) + (\tfrac{1}{2}) + Nna\} \times g - (Nn/2) \qquad (440b)$$

From these definitions, Eqs. (428) and (429) can be rewritten as:

$$DD(k + j - 1, n) = \{H42N(n) + (g \times k)\} \times \qquad (441/428)$$
$$DE(k + j - 1, n) +$$
$$\{H41N(n) - (g \times k)\} \times$$
$$RPE(k + j - 1, n)$$

where k=1 to M/2

$$DD(k + j - 1, n) = \{H43N(n) + g \times \qquad (442/429)$$
$$((M/2) - k)\} \times DF(k + j - 1, n) +$$
$$\{H41N(n) - (g \times M)/2 - g \times$$
$$(k - (M/2))\} \times RMF(k + j - 1, n)$$

where k=M/2+1 to M
Here
 DEU(j): set of DE(k+j−1,n)
where k=1 to M/2
 RPEU(j): a set of RPE(k+j−1,n)
where k=1 to M/2
 DFU(j): a set of DF(k+j−1,n)
where k=M/2+1 to M
 RMFU(j): a set of RMF(k+j−1,n)
where k=M/2+1 to M
 DEHU(j): a set of H42N(n)×DE(k+j−1,n)
where k=1 to M/2
 RPHU(j): a set of H41N(n)×RPE(k+j−1,n)
where k=1 to M/2
 DFHU(j): a set of H43N(n)×DF(k+j−1,n)
where k=M/2+1 to M
 RMHU(j): a set of H41N(n)×RME(k+j−1,n)
where k=M/2+1 to M
 DEKU(j): a set of k×DE(k+j−1,n)
where k=1 to M/2
 RPKU(j): a set of k×RPE(k+j−1,n)
where k=1 to M/2
 DFKU(j): a set of (k−M/2)×DF(k+j−1,n)
where k=M/2+1 to M
 RMKU(j): a set of (k−M/2)×RMF(k+j−1,n)
where k=M/2+1 to M
The following images are defined:

$$IEA(j) = BP[CONV\{DEU(j)\}] \qquad (446)$$

$$IRPA(j) = BP[CONV\{RPEU(j)\}] \qquad (447)$$

$$IFA(j) = BP[CONV\{DFU(j)\}] \qquad (448)$$

$$IRMA(j) = BP[CONV\{RMFU(j)\}] \qquad (449)$$

$$IEH(j) = BP[CONV\{DEHU(j)\}] \qquad (450)$$

$$IRPH(j) = BP[CONV\{RPHU(j)\}] \qquad (450A)$$

$$IFH(j)BP[CONV\{DFHU(j)\} \qquad (451)$$

$$IRMH(j) = BP[CONV\{RMHU(j)\}] \qquad (451A)$$

$$IEK(j) = BP[CONV\{DEKU(j)\}] \qquad (452)$$

$$IRPK(j) = BP[CONV\{RPKU(j)\}] \qquad (453)$$

$$IFK(j) = BP[CONV\{DFKU(j)\}] \qquad (454)$$

$$IRMK(j) = BP[CONV\{RMKU(j)\}] \qquad (455)$$

where
 BP: back projection calculation

CONV: convolution calculation.
The BP and CONV calculations are performed in units of projection angles.
where DDU(j): a set of DD(k+j−1,n)
where k=1 to M/2

DDV(j): a set of DD(k+j−1,n)
where k=M/2+1 to M

If the j-th image is represented by I(j), I(j) is given by:

$$I(j)=BP[CONV\{DDU(j)\}]+BP[CONV\{DDV(j)\}] \quad (55a)$$

Therefore, $$\begin{aligned}I(j) = \ & IEH(j) + g \times IEK(j) + IRPH(j) - \\ & g \times IRPK(j) + IFH(j) - g \times IFK(j) - \\ & IRMH(j) + \{(g \times M)/2\} \times \\ & IRMA(j) + g \times IRMK(j)\end{aligned} \quad (456)$$

Similarly, a (j+1)th image I(j+1) is given by:

$$\begin{aligned}I(j+1) = \ & IEH(j+1) + g \times IEK(j+1) + \\ & IRPH(j+1) - g \times IRPK(j+1) + \\ & IFH(j+1) - g \times IFK(j+1) - \\ & IRMH(j+1) + \{(g \times M)/2\} \times \\ & IRMA(j+1) + g \times IRMK(j+1)\end{aligned} \quad (457)$$

If a subtraction image between the (j+1)th image and the j-th image is represented by $\Delta(j+1)$, $\Delta(j+1)$ is given by:

$$\Delta I(j+1)=I(j+1)-I(j) \quad (457A)$$

Also, $$I(j+1)=I(j)+\Delta I(j+1) \quad (457B)$$

Therefore, $$\begin{aligned}\Delta I(j+1) = \ & IEH(j+1) - IEH(j) + g \times \\ & \{IEH(j+1) - IEK(j)\} + \\ & IRPH(j+1) - IRPH(j) - g \times \\ & \{IRPK(j+1) - IRPK(j)\} + \\ & IFH(j+1) - IFH(j) - g \times \\ & \{IFK(j+1) - IFK(j)\} - \\ & \{IRMH(j+1) - IRMH(j)\} + \\ & \{g \times (M/2)\}\{IRMA(j+1) - IRMA(j)\} + \\ & g \times \{IRMK(j+1) - IRMK(j)\}\end{aligned} \quad (458)$$

The terms of the right-hand side of Eq. (458) are sequentially calculated as follows:
First, $$\begin{aligned}IEH(j+1) - IEH(j) = \ & BP[CONV\{-H42N(n) \times \\ & DE(j,n)\}] + \\ & BP[CONV\{H42N(n) \times \\ & DE(j+(M/2),n)\}]\end{aligned} \quad (459)$$

$$\begin{aligned}IFH(j+1) - IFH(j) = \ & BP[CONV\{-H43N(n) \times \\ & DF(j+(M/2),n)\}] + \\ & BP[CONV\{H43N(n) \times \\ & DF(j+M,n)\}]\end{aligned} \quad (460)$$

Since DE(j,n) and DF(j+M,n) have the same projection angle, Eqs. (459) and (460) are synthesized as follows:

$$\begin{aligned}IEH(j+1) - IEH(j) + IFH(j+1) - IFH(j) = & \\ BP[CONV\{-H42N(n) \times DE(j,n) + H43N(n) \times & \\ DF(j+M,n)\}] + BP[CONV\{H42N(n) \times & \\ DE(j+(M/2),n) - H43N(n) \times DF(j+(M/2),n)\}]\end{aligned} \quad (461)$$

Next, $$IEK(j+1) - IEK(j) = \quad (462)$$

$$-IEA(j) + BP[CONV\{(M/2) \times DE(j+(M/2),n)\}]$$

Note that IEA(j+1) is given by:

$$\begin{aligned}IEA(j+1) = \ & IEA(j) - BP[CONV\{DE(j,n)\}] + \\ & BP[CONV\{DE(j+(M/2),n)\}]\end{aligned} \quad (463)$$

Next, $$IFK(j+1)-IFK(j)=-IFA(j)+BP[CONV\{(M/2)\times DF(j+M,n)\}] \quad (464)$$

Note that IFA(j+1) is given by:

$$\begin{aligned}IFA(j+1) = \ & IFA(j) - \\ & BP[CONV\{DF(j+(M/2),n)\}] + \\ & BP[CONV\{DF(j+M,n)\}]\end{aligned} \quad (465)$$

Here, we define:

$$IEFA(j)=IEA(j)-IFA(j) \quad (466)$$

from Eq. (466), the following Eq. is obtained:

$$\begin{aligned}IEFA(j+1) = \ & IEA(j+1) - IFA(j+1) \\ = \ & IEA(j) - IFA(j) - \\ & BP[CONV\{DE(j,n)\}] + \\ & BP[CONV\{DE(j+(M/2),n)\}] + \\ & BP[CONV\{DF(j+(M/2),n)\}] - \\ & BP[CONV\{DF(j+M,n)\}]\end{aligned} \quad (467)$$

Since DE(j,n) and DF(j+M,n) have the same projection angle, Eq. (467) is modified as:

$$\begin{aligned}IEFA(j+1) = IEFA(j) - & \\ BP[CONV\{DE(j,n) + DF(j+M,n)\}] + & \\ BP[CONV\{DE(j+(M/2),n) + DF(j+(M/2),n)\}] & \end{aligned} \quad (468)$$

Therefore, $$\begin{aligned}\{IEK(j+1) - IEK(j)\} - \{IFK(j+1) - IFK(j)\} = & \\ -IEFA(j) + BP[CONV\{(M/2) \times DE(j+(M/2),n)\}] - & \\ BP[CONV\{(M/2) \times DF(j+M,n)\}] & \end{aligned} \quad (469)$$

Next, $$\begin{aligned}IRPH(j+1) - IRPH(j) = & \\ BP[CONV\{-H41N(n) \times RPE(j,n)\}] + & \\ BP[CONV\{H41N(n) \times RPE(j+(M/2),n)\}] & \end{aligned} \quad (470)$$

Next, $$\begin{aligned}IRMH(j+1) - IRMH(j) = & \\ BP[CONV\{-H41N(n) \times RMF(j+(M/2),n)\}] + & \\ BP[CONV\{H41N(n) \times RMF(j+M,n)\}] & \end{aligned} \quad (470A)$$

Since RPE(j,n) and RMF(j+M,n) have the same projection angle, Eqs. (470) and (470A) are synthesized as follows:

$$\{IRPH(j+1) - IRPH(j)\} - \quad (470B)$$

-continued $$\{IRMH(j+1) - IRMH(j)\} = -BP[CONV\{H41N(n) \times RPE(j,n) + H41N(n) \times RMF(j+M,n)\}] + BP[CONV\{H41N(n) \times RPE(j+(M/2),n) + H41N(n) \times RMF(j+(M/2),n)\}]$$

Next, $$IRMA(j+1) - IRMA(j) = BP[CONV\{RMF(j+M,n)\}] - BP[CONV\{RMF(j+(M/2),n)\}] \quad (471)$$

Therefore, $$\{IRPH(j+1) - IRPH(j)\} = \quad (472)$$
$$\{IRMH(j+1) - IRMH(j)\} + \{(g \times M)/2\} \times \{IRMA(j+1) - IRMA(j)\} =$$
$$-BP[CONV\{H41N(n) \times RPE(j,n) + H41N(n) \times RMF(j+M,n)\}] +$$
$$BP[CONV\{H41N(n) \times RPE(j+(M/2),n) + H41N(n) \times RMF(j+(M/2),n)\}] +$$
$$BP[CONV\{((g \times M)/2) \times RMF(j+M,n)\}] - BP[CONV\{((g \times M)/2) \times RMF(j+(M/2),n)\}] =$$
$$-BP[CONV\{H41N(n) \times RPE(j,n) + \{H41N(n) - (g \times M)/2\} \times RMF(j+M,n)\}] +$$
$$BP[CONV\{H41N(n) \times RPE(j+(M/2),n) + \{H41N(n) - (g \times M)/2\} \times RMF(j+(M/2),n)\}] =$$
$$-BP[CONV\{H41N(n) \times RPE(j,n) + \{(g+Nn)/2\} \times RMF(j+M,n)\} + BP[CONV\{H41N(n) \times RPE(j+(M/2),n) + \{(g+Nn)/2\} \times RMF(j+(M/2),n)\}]$$

Furthermore, $$IRPK(j+1) - IRPK(j) = \quad (473)$$
$$-IRPA(j) + BP[CONV\{(M/2) \times RPE(j+(M/2),n)\}]$$

Note that IRPA(j+1) is given by:

$$\begin{aligned} IRPA(j+1) &= IRPA(j) - \quad (474)\\ & BP[CONV\{RPE(j,n)\}] + \\ & BP[CONV\{RPE(j+(M/2),n)\}] \end{aligned}$$

Next, $$IRMK(j+1) - IRMK(j) = -IRMA(j) + BP[CONV\{(M/2) \times RMF(j+M,n)\}] \quad (475)$$

Note that IRMA(j+1) is given by:

$$\begin{aligned} IRMA(j+1) &= IRMA(j) - \quad (476)\\ & BP[CONV\{RMF(j+(M/2),n)\}] + \\ & BP[CONV\{RMF(j+M),n)\}] \end{aligned}$$

The following definition is given:

$$IPMA(j) = IRPA(j) - IRMA(j) \quad (477)$$

From this definition, the following Eq. can be obtained:

$$\begin{aligned} IRMA(j+1) &= IRPA(j+1) - IRMA(j+1) \quad (478)\\ &= IRPA(j) - IRMA(j) - \\ & BP[CONV\{RPE(j,n)\}] + \\ & BP[CONV\{RPE(j+(M/2),n)\}] + \\ & BP[CONV\{RMF(j+(M/2),n)\}] - \\ & BP[CONV\{RMF(j+M),n)\}] \end{aligned}$$

Since RPE(j,n) and RMF(j+M,n) have the same projection angle, Eq. (478) is modified as follows:

$$IPMA(j+1) = IPMA(j) - \quad (479)$$
$$BP[CONV\{RPE(j,n) + RMF(j+M,n)\}] +$$
$$BP[CONV\{RPE(j+(M/2),n) + RMF(j+(M/2),n)\}]$$

Therefore, $$-\{IRPK(j+1) - IRPK(j)\} + \quad (480)$$
$$\{IRMK(j+1) - IRMK(j)\} = IPMA(j) -$$
$$BP[CONV\{(M/2) \times RPE(j+(M/2),n)\}] +$$
$$BP[CONV\{(M/2) \times RMF(j+M),n)\}]$$

Therefore, when Eqs. (461), (469), (472), and (480) are substituted in Eq. (458), the subtraction image $\Delta(j+1)$ between the (j+1)th image and the j-th image is given by:

$$\begin{aligned} \Delta I(j+1) = & BP[CONV\{-H42N(n) \times \quad (481)\\ & DE(j,n) + H43N(n) \times DF(j+M,n)\}] + \\ & BP[CONV\{H42N(n) \times DE(j+(M/2),n) - \\ & H43(n) \times DF(j+(M/2),n)\}] - \\ & g \times IEFA(j) + BP[CONV\{((g \times M)/2) \times \\ & DE(j+(M/2),n)\}] - BP[CONV\{((g \times M)/2) \times DF(j+M,n)\}] - \\ & BP[CONV\{H41N(n) \times RPE(j,n) - \\ & ((g+Nn)/2) \times RMF(j+M,n)\}] + \\ & BP[CONV\{H41N(n) \times \\ & RPE(j+(M/2),n) - ((g+Nn)/2) \times \\ & RMF(j+(M/2),n)\}] + g \times IPMA(j) - \\ & BP[CONV\{((g \times M)/2 \times \\ & RPE(j+(M/2),n)\}] + \\ & BP[CONV((g \times M)/2) \times \\ & RMF(j+M),n)\}] \end{aligned}$$

Summing over the same projection angle, Eq. (481) becomes:

$$\begin{aligned} \Delta I(j+1) = & BP[CONV\{-H42N(N) \times \quad (482)\\ & DE(j,n) + (H43N(n) - \\ & (g \times M)/2) \times DF(j+M,n) - \\ & H41N(n) \times RPE(j,n) + (-(g+Nn)/2 + \\ & (g \times M)/2) \times RMF(j+M,n)\}] + \\ & BP[CONV\{(H42N(n) + (g \times M)/2) \times \\ & DE(j+(M/2),n) - H43N(n) \times \\ & DF(j+(M/2),n) + (H41N(n) - \\ & (g \times M)/2 \times RPE(j+(M/2),n) + \\ & ((g+Nn)/2) \times RMF(j+(M/2),n)\}] + \\ & g \times \{IPMA(j) - IEFA(j)\} \end{aligned}$$

Here, we define:

$$IB(j) = IPMA(j) - IEFA(j) \quad (483)$$

Since $$H43N(n) - ((g \times m)/2) = -H42N(n) \quad (483A)$$

then, the (j+1)th subtraction image ΔI(j+1) is given by:

$$\begin{aligned}
\Delta I(j+1) = \ & BP[CONV\{-H24N(N) \times \\
& DE(j,n) + DF(j+M,n) - H41N(n) \times \\
& RPE(j,n) + ((M \times g) - g - Nn))/2) \times \\
& RMF(j+M,n)\}] + \\
& BP[CONV\{H42N(n) + (g \times M)/2) \times \\
& DE(j+(M/2),n) - H43N(n) \times \\
& DF(j+(M/2),n) + ((g+Nn)/2) \times \\
& (RPE(j+(M/2),n) + \\
& RMF(j+(M/2),n))\}] + g \times IB(j)
\end{aligned} \quad (484)$$

From Eqs. (483), (479), and (468), IB(j+1) is given by:

$$\begin{aligned}
IB(j+1) \ =\ & IPMA(j+1) - IEFA(j+1) \\
=\ & IPMA(j) - BP[CONV\{RPE(j,n) + \\
& RMF(j+M,n)\}] + \\
& BP[CONV\{RPE(j+(M/2),n) + \\
& RMF(j+(M/2),n)\}] - IEFA(j) + \\
& BP[CONV\{DE(j,n) + DF(j+M,n)\}] - \\
& BP[CONV\{DE(j+(M/2),n) + \\
& DF(j+(M/2),n)\}] \\
=\ & IB(j) - BP[CONV\{-DE(j,n) + \\
& RPE(j,n) - DF(j+M,n) + \\
& RMF(j+M,n)\}] + \\
& BP[CONV\{-DE(j+(M/2),n) + \\
& RPE(j+(M/2),n) - \\
& DF(j+(M/2),n) + RMF(j+(M/2),n)\}]
\end{aligned} \quad (485)$$

$$\begin{aligned}
IB(j) \ =\ & IPMA(j) - IEFA(j) \\
=\ & IRPA(j) - IRMA(j) - IEA(j) + IFA(j) \\
=\ & BP[CONV\{RPEU(j)\}] - \\
& BP[CONV\{RMFU(j)\}] - \\
& BP[CONV\{DEU(j)\}] + \\
& BP[CONV\{DFU(j)\}] \\
=\ & BP[CONV\{DERPU(j)\}] - \\
& BP[CONV\{DERMU(j)\}]
\end{aligned} \quad (486)$$

where

DERPU(j): a set of RPE(k+j−1,n)−DE(k+j−1,n) where k=1 to M/2

DERMU(j): a set of RMF(k+j−1,n)−DF(k+j−1,n) where k=M/2+1 to M

Equation (457B) is modified as:

$$I(j) = I(j+1) - \Delta I(j+1) \quad (486A)$$

When j is replaced by j−1 in Eq. (486A), the following Eq. is obtained:

$$I(j-1) = I(j) - \Delta I(j) \quad (486B)$$

When j is replaced by j−1 in Eq. (484), ΔI(j) is given by:

$$\begin{aligned}
\Delta I(j) = \ & BP[CONV\{-H42N(n) \times \\
& (DE(j-1,n) + DF(j-1+M,n) - \\
& H41N(n) \times RPE(j-1,n) + \\
& ((M \times g) - g - Nn)/2) \times \\
& RMF(j-1+M,n)\}] + \\
& BP[CONV\{H42N(n) + ((g \times M)/2) \times \\
& DE(j-1+(M/2),n) - H43N(n) \times \\
& DF(j-1+(M/2),n) + \\
& ((g+Nn)/2) \times (RPE(j-1+(M/2),n) + \\
& RMF(j-1+(M/2),n)\}] + g \times IB(j-1)
\end{aligned} \quad (487)$$

Equation (485) is rewritten as:

$$\begin{aligned}
IB(j) =\ & IB(j+1) + \\
& BP[CONV\{-DE(j,n) + RPE(j,n) - \\
& DF(j+M,n) + RMF(j+M,n)\}] - \\
& BP[CONV\{-DE(j+(M/2),n) + \\
& RPE(j+(M/2),n) - \\
& DF(j+(M/2),n) + RMF(j+(M/2),n)\}]
\end{aligned} \quad (489)$$

When j is replaced by j−1, IB(j−1) is calculated from Eq. (489):

$$\begin{aligned}
IB(j-1) =\ & IB(j) + \\
& BP[CONV\{-DE(j-1,n) + \\
& RPE(j-1,n) - \\
& DF(j-1+M,n) + \\
& RMF(j-1+M,n)\}] - \\
& BP[CONV\{-DE(j-1+(M/2),n) + \\
& RPE(j-1+(M/2),n) - \\
& DF(j-1+(M/2),n) + \\
& RMF(j-1+(M/2),n)\}]
\end{aligned} \quad (490)$$

As described above, an image I(j+1) or I(j−1) adjacent to the already reconstructed image I(j) can be continuously reconstructed using Eqs. (457B) and (484) or Eqs. (486B) and (487).

Equation (55a) requires M number of CONV and BP calculations. Each of Eqs. (484) and (487) requires two CONV and BP calculations. However, in order to continuously reconstruct images, IB(j+1) or IB(j−1) must be obtained. IB(j+1) is obtained by Eq. (85), and IB(j−1) is obtained by Eq. (90). Each of Eqs. (85) and (90) requires two CONV and BP calculations. Therefore, in order to continuously obtain I(j+1) or I(j−1), four CONV and BP calculations are required.

An amount of calculation other than the CONV and BP calculations is very small as compared to the amount of the CONV and BP calculations. Therefore, the total amount of calculation is almost determined by the number of CONV and BP calculations. In general, since M (the number of views) is considerably larger than 4, reconstruction using Eqs. (457B) and (484) or Eqs. (486B) and (487) has a very small amount of calculation as compared to Eq. (55a).

The above description is complicated since all modifications of Eqs. are presented. Only Eqs. associated with the principle of continuous reconstruction according to the present invention will be summarized below. As the numbers of Eqs., numbers used in the above description are presented on the left-hand side of "/", and renumbered numbers are presented on the right-hand side of "/" where the purpose of arrangement.

fan angle: 2α number of data per view: N (even number)
$\Delta\alpha = 2\alpha/N$
angle between two adjacent views: $\Delta\theta$
number of views per 360°: M (even number)
$M \times \Delta\theta = 360°$
view number: m
projection data: D(m,n)
projection angle of m-th view: $m \times \Delta\theta$
gantry moving distance between projections of source fan: e
(the number of views per 360° of source fan)/M: g
position of n-th data of m-th view of detector fan: $m \times g \times e + n \times e$
total number of scanned views: MM $$aa = \Delta\alpha/\Delta\theta \qquad (6)/(491)$$

$$nn = N+1-n \qquad (3)/(492)$$

$$mp = m + M/2 - (N+1-2n) \times aa \qquad (4)/(493)$$

$$mm = m - M/2 - (N+1-2n) \times aa \qquad (5)/(494)$$

ci: an integral part of $(N-1) \times aa$
cp: a decimal part of $(N-1) \times aa$
mpi: an integral part of mp
mpp: a decimal part of mp
mmi: an integral part of mm
mmp: a decimal part of mm $$mmr = mr + ci + 1 - (N+1-2n) \times aa \qquad (15)/(495)$$

mmri: an integral part of mmr
mmrp: a decimal part of mmr $$R(mr,n) = D(mmri,nn) \times (1-mmrp) + D(mmri+1,nn) \times mmrp \qquad (16)/(496)$$

where $mr = 1$ to $MM - 2 \times ci - 2$ $$RP(m,n) = R(m + (M/2) - ci - 1, n) \qquad (13)/(497)$$

$$RM(m,n) = R(m - (M/2) - ci - 1, n) \qquad (14)/(498)$$

$$H41(k,n) = \{(M+1)/2 - k\} \times g + (Nn/2) \qquad (430)/(499)$$

$$H42(k,n) = \{k - (\tfrac{1}{2}) - Nna\} \times g + (Nn/2) \qquad (431)/(500)$$

$$H43(k,n) = \{M - k + (\tfrac{1}{2}) + Nna\} \times g - (Nn/2) \qquad (432)/(501)$$

$$H44(n) = \{(M/2) - Nna\} \times g + Nn \qquad (433)/(502)$$

$$H45(n) = \{(M/2) + Nna\} \times g - Nn \qquad (434)/(503)$$

$$DE(m,n) = D(m,n)/H44(n) \qquad (435)/(504)$$

$$DF(m,n) = D(m,n)/H45(n) \qquad (436)/(505)$$

$$RPE(m,n) = RP(m,n)/H44(n) \qquad (437)/(506)$$

$$RMF(m,n) = RM(m,n)/H45(n) \qquad (438)/(507)$$

$$H41N(n) = \{(M+1) \times g + Nn\}/2 \qquad (439)/(508)$$

$$H42N(n) = (Nn/2) - \{(\tfrac{1}{2}) + Nna\} \times g \qquad (440a)/(509)$$

$$H43N(n) = \{(M/2) + (\tfrac{1}{2}) + Nna\} \times g - (Nn/2) \qquad (440b)/(510)$$

$$\begin{aligned} I(j) = &\ BP[CONV\{H42(k,n) \times DE(k+j-1) + H41(k,n) \times RPE(k+j-1,n)\}] + \\ & BP[CONV\{H43(k+(M/2),n) \times DF(k+j-1+(M/2),n) - \\ & H41(k+(M/2)) \times RMF(k+j-1+(M/2),n)\}] \end{aligned} \qquad (511)$$

where $k = 1$ to $M/2$ $$\begin{aligned} IB(j) = &\ BP[CONV\{RPE(k+j-1+(M/2),n) - DE(k+j-1+(M/2),n)\}] + \\ & BP[CONV\{RMF(k+j-1+(M/2),n) - DF(k+j-1+(M/2),n)\}] \end{aligned} \qquad (512)$$

where $k = 1$ to $M/2$ $$\begin{aligned} IB(j+1) = &\ IB(j) - \\ & BP[CONV\{-DE(j,n) + RPE(j,n) - DF(j+M,n) + RMF(j+M,n)\}] + \\ & BP[CONV\{-DE(j+(M/2),n) + RPE(j+(M/2),n) - DF(j+(M/2),n) + RMF(j+(M/2),n)\}] \end{aligned} \qquad (485)/(513)$$

$$\begin{aligned} IB(j-1) = &\ IB(j) + \\ & BP[CONV\{-DE(j-1,n) + RPE(j-1,n) - DF(j-1+M,n) + RMF(j-1+M,n)\}] - \\ & BP[CONV\{-DE(j-1+(M/2),n) + RPE(j-1+(M/2),n) - DF(j-1+(M/2),n) + RMF(j-1+(M/2),n)\}] \end{aligned} \qquad (490)/(514)$$

$$I(j+1) = I(j) + \Delta I(j+1) \qquad (457B)/(514A)$$

$$\begin{aligned} \Delta I(j+1) = &\ BP[CONV\{-H42N(N) \times DE(j,n) + DF(j+M,n)) - \\ & H41N(n) \times RPE(j,n) + \\ & ((M \times g) - g - Nn)/2) \times RMF(j+M,n)\}] + \\ & BP[CONV\{H42N(n) + (g \times M)/2) \times DE(j+(M/2),n) - H43N(n) \times DF(j+(M/2),n) + ((g+Nn)/2) \times (RPE(j+(M/2),n) + RMF(j+(M/2),n)\}] + g \times IB(j) \end{aligned} \qquad (484)/(515)$$

$$I(j-1) = I(j) - \Delta I(j) \qquad (486B)/(515A)$$

$$\begin{aligned}
\Delta I(j) = \quad & BP[CONV\{-H42N(n) \times \\
& (DE(j-1,n) + DF(j-1+M,n) - \\
& H41N(n) \times RPE(j-1,n) + \\
& ((M \times g) - g - Nn)/2) \times \\
& RMF(j-1+M,n)\}] + \\
& BP[CONV\{H42N(n) + \\
& ((g \times M)/2) \times DE(j-1+(M/2),n) - \\
& H43N(n) \times DF(j-1+(M/2),n) + \\
& ((g+Nn)/2) \times (RPE(j-1+(M/2),n) + \\
& RMF(j-1+(M/2),n))\}] + g \times IB(j-1)
\end{aligned} \quad (487)/(516)$$

Figure 18:
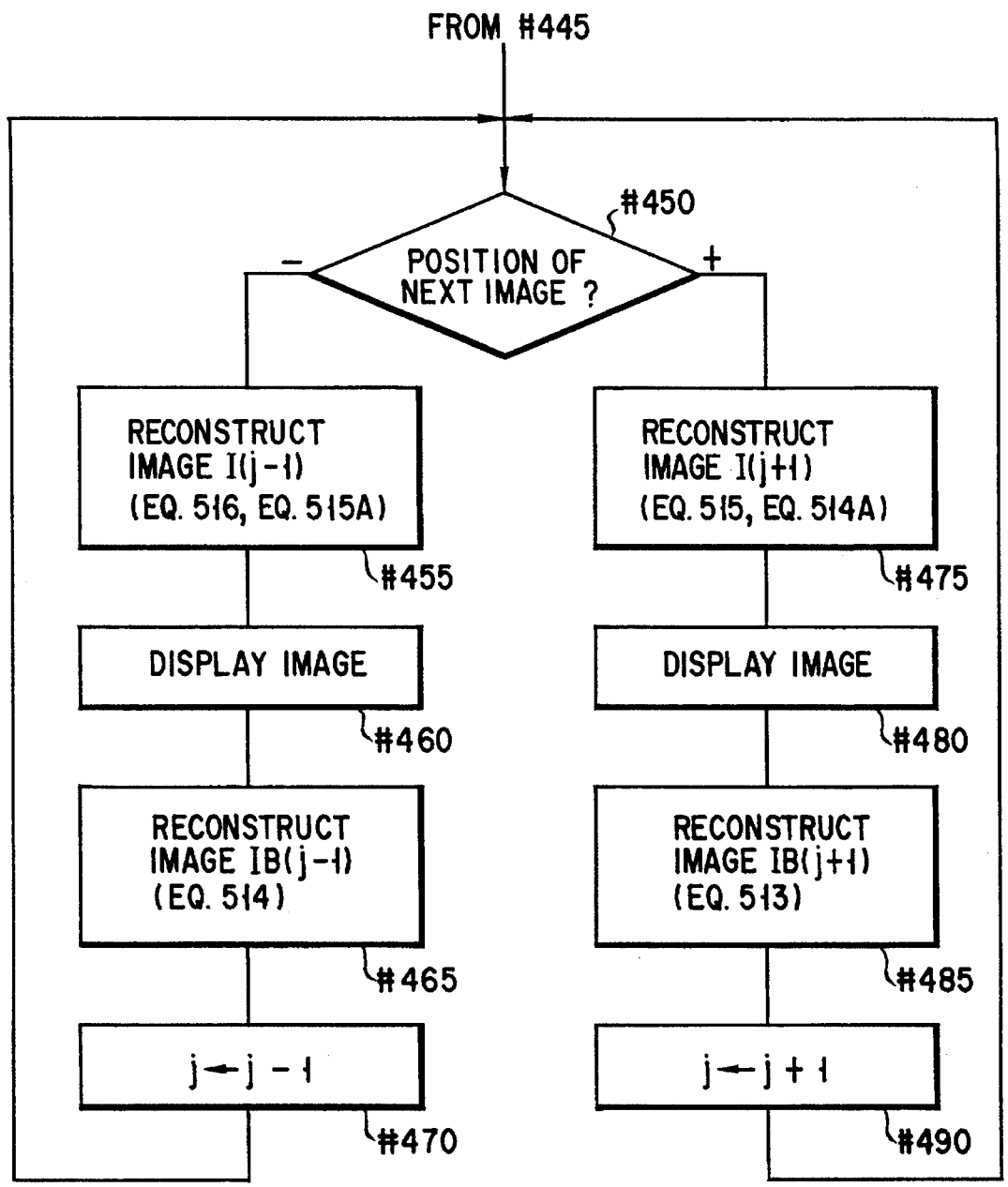
FIG. 18 is a flow chart showing a second part of the operation of the fourth embodiment.

The method according to the fourth embodiment of the present invention will be described in detail below. This embodiment can be practiced in substantially the same manner as in the first embodiment, except for Eqs. used in calculations. The arrangement and the overall control flow of this embodiment are the same as those in the first embodiment. The operation of the fourth embodiment will be described below with reference to FIGS. 17 and 18.

In step #410, a helical scan is performed to acquire projection data. The projection data are preprocessed by the preprocessing circuit 30, and are converted into detector fan data. Thereafter, the detector fan data are stored in the raw data memory 32.

Upon completion of the scan or after a predetermined amount of raw data are acquired, reflection beam data (reflection view data) R(mr,n) are calculated based on Eq. (496), and are stored in the reflection view memory 38 in step #415.

In step #420, a number "j" of an image to be reconstructed is input.

In step #425, necessary initialization is executed.

In step #430, DE(m,n), DF(m,n), RPE(m,n), and RMF(m,n) are calculated for m=1 to MM−2ci−2 and n=1 to N on the basis of Eqs. (435) to (438), and these data are stored in the intermediate data memory 39.

In step #435, a j-th image I(j) is reconstructed based on Eq. (511).

In step #440, the reconstructed image is displayed.

In step #445, an image IB(j) is reconstructed based on Eq. (512).

In step #450, the position of the next image to be reconstructed is discriminated. The position is selected by instructing the change direction of image number "j" using, e.g., a three-point switch. If the switch is set at the neutral position, the control waits until either direction is instructed. If it is instructed to change "j" in the minus direction, the flow advances to step #455; if it is instructed to change "j" in the plus direction, the flow advances to step #475.

If the minus direction is selected in step #450, the immediately preceding image I(j−1) is reconstructed using Eqs. (516) and (515A) in step #455.

In step #460, the image I(j−1) reconstructed in step #455 is displayed.

In step #465, an image IB(j−1) is reconstructed based on Eq. (514).

In step #470, "j" is decremented by 1, and the flow returns to step #450.

If the plus direction is selected in step #450, the next image I(j+1) is reconstructed using Eqs. (515) and (514A) in step #475.

In step #480, the image I(j+1) reconstructed in step #475 is displayed.

In step #485, an image IB(j+1) is reconstructed based on Eq. (513).

In step #490, "j" is incremented by 1, and the flow returns to step #450.

Upon repetition of the above-mentioned operation, adjacent images are continuously reconstructed using Eqs. (516) and (515A) or Eqs. (515) and (514A) while continuously changing "j". The change direction of "j" may be changed in step #450 or a change in "j" may be ended.

As described above, according to the fourth embodiment, in the fourth generation helical scan X-ray CT apparatus as well, the first tomographic image is normally reconstructed by executing convolution and back projection calculations of a virtual view obtained by interpolation or extrapolation using projection data and their reflection beam data in a range of 360°+a double fan angle 4α before and after the slice position. However, a tomographic image adjacent to the first tomographic image is reconstructed in such a manner that a difference between data used in reconstruction of the first tomographic image and data necessary for normally reconstructing a current tomographic image to be reconstructed is subjected to convolution and back projection calculations, and the calculation result (subtraction image) is added to the already reconstructed tomographic image. Therefore, a large number of tomographic images can be reconstructed within a short period of time, and a large number of images whose slice positions are shifted from each other can be continuously reconstructed.

A modification of the fourth embodiment will be described below. In the fourth embodiment, as shown in Eqs. (516) and (515A) or Eqs. (515) and (514A), a tomographic image adjacent to the already reconstructed tomographic image is reconstructed in such a manner that a subtraction image is calculated by executing convolution and back projection calculations of a difference between data used in reconstruction of the already reconstructed tomographic image and data necessary for normally reconstructing a current tomographic image to be reconstructed, and the subtraction image is synthesized with the already reconstructed tomographic image. However, the subtraction image need not always be calculated. More specifically, the difference between data used in reconstruction of the already reconstructed tomographic image and data necessary for normally reconstructing a current tomographic image to be reconstructed may be superposed on the already reconstructed tomographic image, and the superposed result may be subjected to convolution and back projection calculations to calculate the current tomographic image. In this case, (j−1)th and (j+1)th images are expressed as follows:

$$\begin{aligned}
I(j+1) = \quad & I(j) + BP[CONV\{-H42N(n) \times \\
& (DE(j,n) + DF(j+M,n)) - \\
& H41N(n) \times RPE(j,n) + \\
& ((M \times g) - g - Nn)/2) \times \\
& RMF(j+M,n)\}] + \\
& BP[CONV\{H42N(n) + \\
& ((g \times M)/2 \times DE(j+(M/2),n) - \\
& H43N(n) \times DF(j+(M/2),n) + \\
& ((g+Nn)/2) \times (RPE(j+(M/2),n) + \\
& RMF(j+(M/2),n)\}] + g \times IB(j)
\end{aligned} \quad (517)$$

$$\begin{aligned}
I(j-1) = \ & I(j) - BP[CONV\{-H42N(n) \times \\
& (DE(j-1,n) + DF(j-1+M,n) - \\
& H41N(n) \times RPE(j-1,n) + \\
& ((M \times g - g - Nn)/2) \times \\
& RMF(j-1+M,n)\}] - \\
& BP[CONV\{H42N(n) + \\
& ((g \times M)/2) \times DE(j-1+(M/2),n) - \\
& H43N(n) \times DF(j-1+(M/2),n) + \\
& ((g+Nn)/2) \times RPE(j-1+(M/2),n) + \\
& RMF(j-1+(M/2),n)\}] + g \times IB(j-1)
\end{aligned} \quad (518)$$

In the above embodiment, all reflection views are calculated prior to reconstruction. However, reflection views may be calculated as needed. Furthermore, when the detector fan is asymmetrical with the center line, substantially the same operation as in the fourth embodiment can be executed, except for an interpolation or extrapolation method (for example, reflection data more than two data, e.g., four data, are interpolated or extrapolated upon calculation of reflection views).

In the fourth embodiment, adjacent images are sequentially reconstructed, and are sequentially displayed. Alternatively, a display operation may be performed in units of a plurality of "n" images. A fifth embodiment for executing this operation will be described below.

Figure 19:
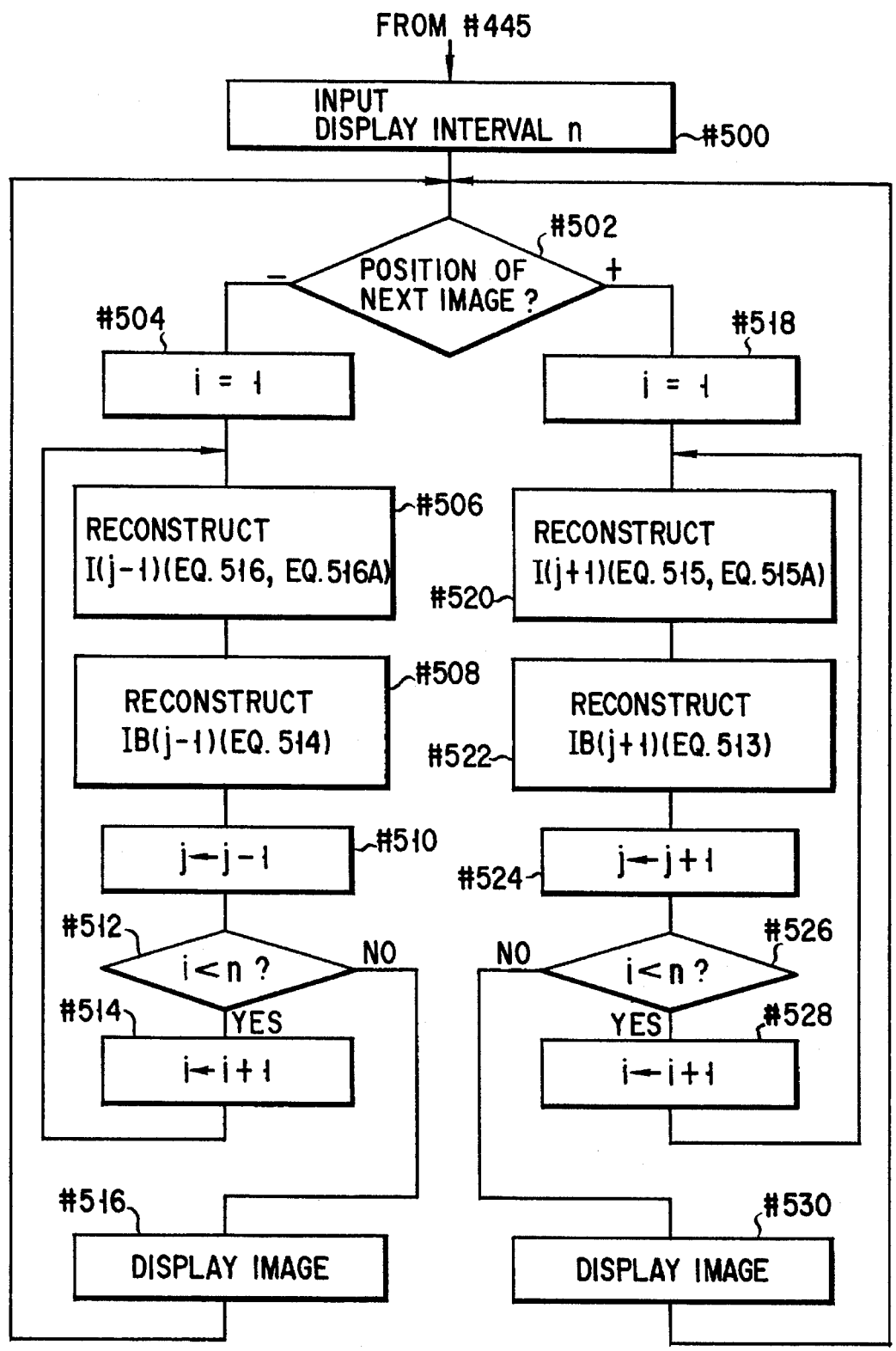
FIG. 19 is a flow chart showing an operation according to a fifth embodiment of the present invention.

FIG. 19 is a flow chart of the fifth embodiment. Since the operation up to step #445 (i.e., the j-th image I(j) is reconstructed and displayed, and an image IB(j) is reconstructed) is the same as that in the fourth embodiment, steps associated with the operation are not shown.

In step #500, a display image interval "n" (n≥1) is input.

If the minus direction is instructed in step #502, i=1 is set in step #504, a (j−1)th image is reconstructed using Eqs. (516) and (516A) in step #506, an image IB(j−1) is reconstructed using Eq. (514) in step #508, and "j" is decremented by 1 in step #510. In step #512, it is checked if i<n. If i<n, "i" is incremented by 1 in step #514, and the flow returns to step #506; otherwise, a finally reconstructed image is displayed in step #516, and the flow returns to step #502.

If the plus direction is instructed in step #502, i=1 is set in step #518, a (j+1)th image is reconstructed using Eqs. (515) and (515A) in step #520, an image IB(j+1) is reconstructed using Eq. (513) in step #522, and "j" is incremented by 1 in step #524. In step #526, it is checked if i<n. If i<n, "i" is incremented by 1 in step #528, and the flow returns to step #520; otherwise, a finally reconstructed image is displayed in step #530, and the flow returns to step #502.

A sixth embodiment will be described below. In the fifth embodiment, tomographic images are calculated in steps #506 and #508 or steps #520 and #522 independently of whether or not images are displayed. A (j+n)th image is expressed as follows from Eq. (514A):

$$I(j+n) = I(j) + \sum_{i=1}^{n} \Delta I(j+i) \quad (120)$$

Similarly, a (j−n)th image is expressed as follows from Eq. (515A):

$$I(j-n) = I(j) - \sum_{i=1}^{n} \Delta I(j+1-i) \quad (121)$$

Therefore, in step #506 in the fifth embodiment shown in FIG. 19, in place of calculating the (j−1)th image using Eqs. (516) and (516A), only the second term of the right-hand side of Eq. (121) may be calculated, and step of calculating the (j−n)th image by adding the second term of the right-hand side of Eq. (121) to the j-th image may be added before the image displaying step #516. Similarly, in step #520, in place of calculating the (j+1)th image using Eqs. (515) and (515A), only the second term of the right-hand side of Eq. (120) may be calculated, and step of calculating the (j+n)th image by adding the second term of the right-hand side of Eq. (120) to the j-th image may be added before the image displaying step #530.

Figure 20:
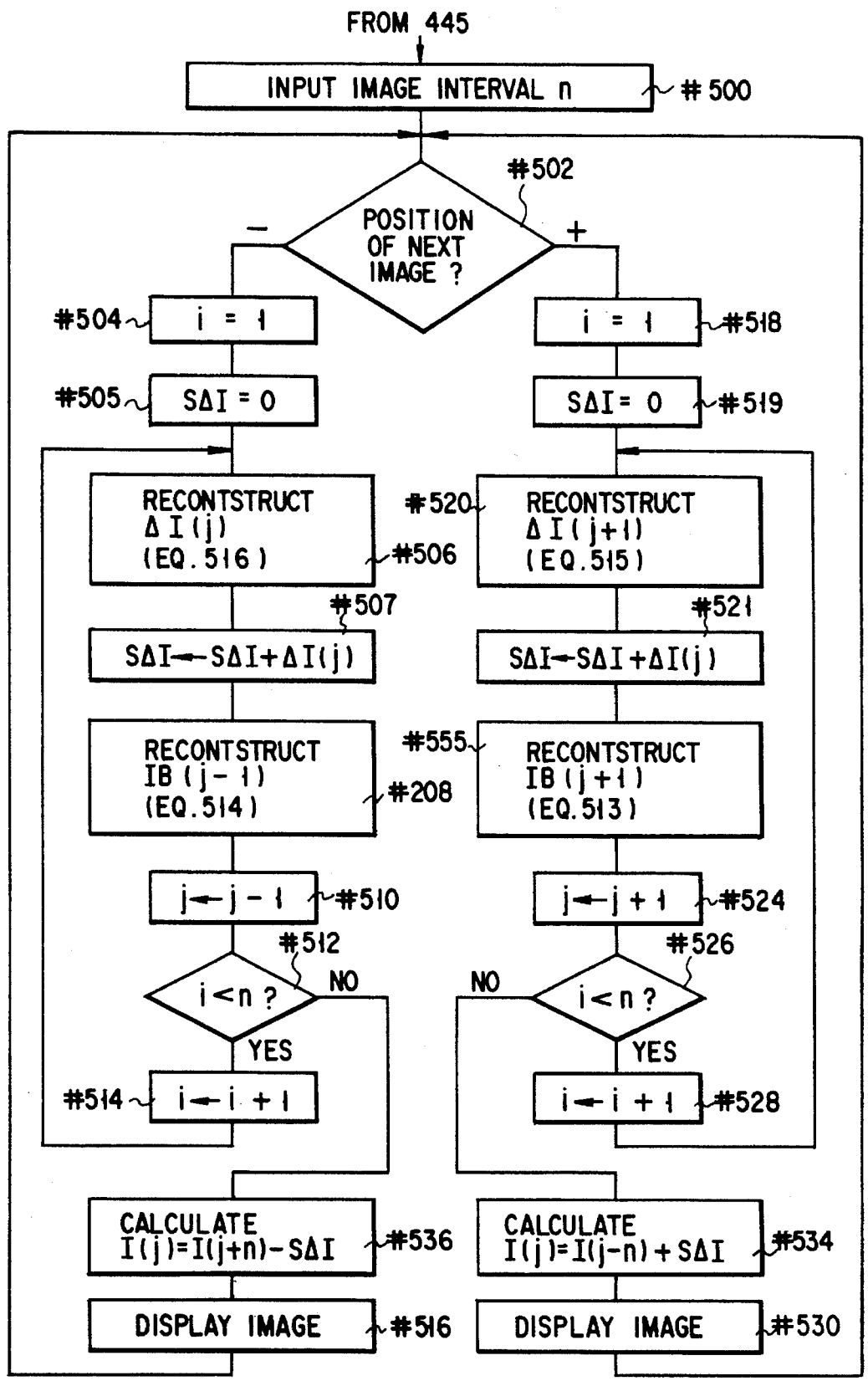
FIG. 20 is a flow chart showing an operation according to a sixth embodiment of the present invention.

FIG. 20 is a flow chart of the sixth embodiment including the above-mentioned calculations. More specifically, $\Sigma\Delta I(j+1)$ is calculated in step #521, $\Sigma\Delta I(j+1-i)$ is calculated in step #507, step #534 of calculating I(j+n) using Eq. (120) is added before step #530, and step #536 of calculating I(j−n) using Eq. (121) is added before step #516.

In each of the above embodiments, the image number is sequentially changed by changing the change direction by using the three-point switch. Alternatively, a desired image number may be input by means of a pointer such as a mouse, a track ball, or the like. In this case, in place of step #450 of the fourth embodiment or step #502 of the fifth or sixth embodiment, a signal from a pointer such as a mouse is read, and if the signal does not change, the control waits in step #450 or #502. If the signal changes, the number "n" of images to be displayed is calculated by multiplying an amount of change with a predetermined coefficient. If n>0, the process in the plus direction is executed; if n<0, the process in the minus direction is executed.

In each of the above embodiments, the reconstructed image is displayed but is not stored in the image memory 22 since a huge memory capacity is required to store all images. Alternatively, all images may be reconstructed, and only designated images may be stored in the image memory 22.

Furthermore, in place of storing a reconstructed image itself, a time curve may be calculated and stored. The time curve represents a change in a CT value (average value) of a certain portion (region of interest) over time.

A seventh embodiment will be described below. In the seventh embodiment, one of a plurality of axial images is partially reconstructed, and coronal, sagittal, and oblique images are calculated from the reconstructed partial images to attain an MPR (Multi-planar reconstruction) display. In a conventional MPR display, since the interval of axial images is large as compared to the pixels of the axial images, steps are undesirably observed in the ordinate (abscissa) of an MPR image. However, in this embodiment, since the interval of axial images can be shortened, an MPR image free from steps can be reconstructed. The seventh embodiment can be applied to both the third and fourth generation CT apparatuses.

Figure 21:
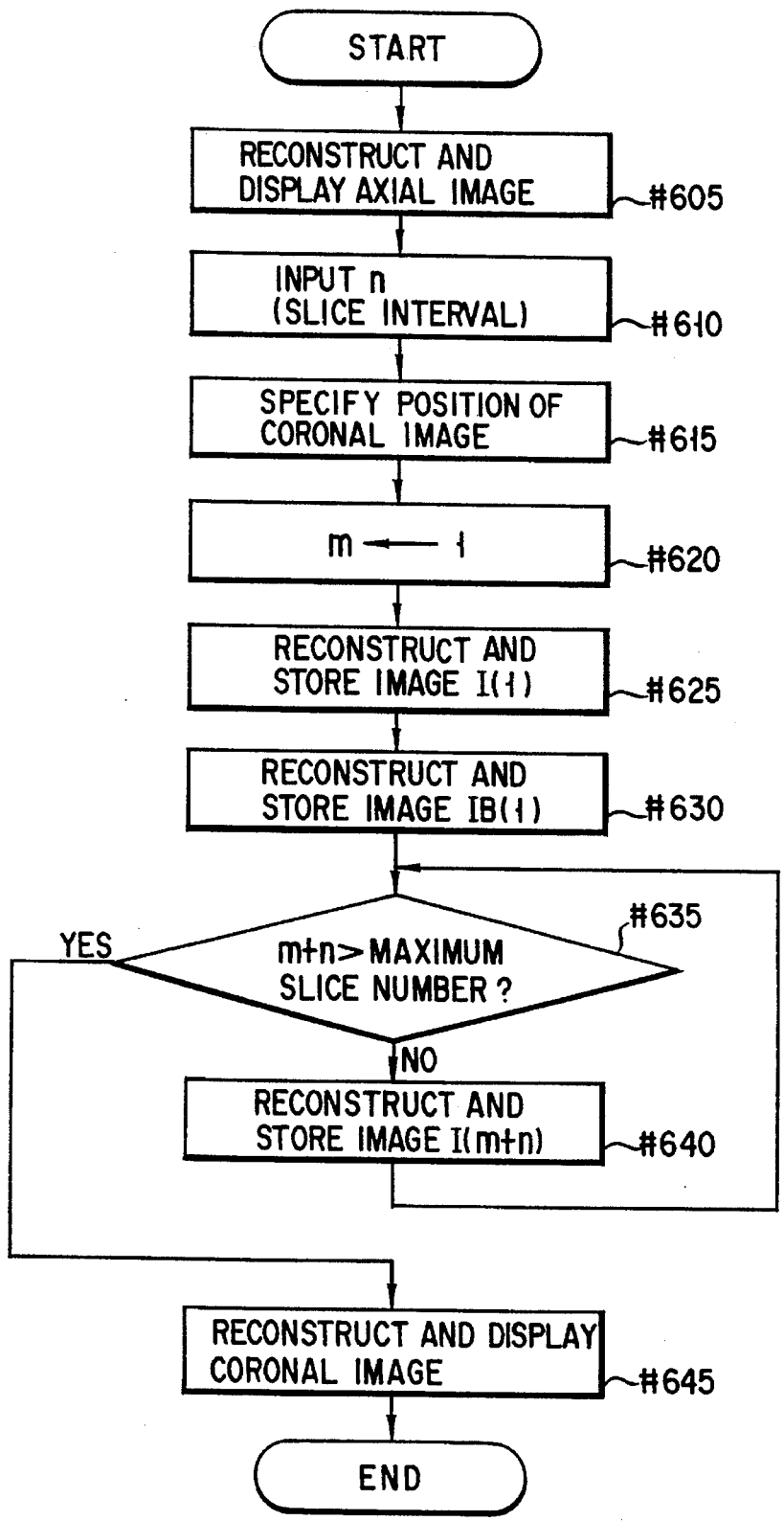
FIG. 21 is a flow chart showing an operation according to a seventh embodiment of the present invention.

FIG. 21 is a flow chart of the seventh embodiment used when a coronal image is to be reconstructed. Sagittal and oblique images can be similarly reconstructed by changing the direction of a line cursor.

In step #605, a proper axial image is displayed by a normal reconstruction method.

In step #610, a slice interval "n" of axial images to be reconstructed is input so as to obtain a coronal image.

In step #615, a position of the coronal image is specified on the axial image by using a horizontal ROI cursor.

In step #620, an image number "m" is set to be 1. In the following operation, convolution, back projection, and image storage are executed for only one line on which the horizontal ROI cursor is displayed.

In step #625, a first image I(1) is reconstructed and stored. The first image is reconstructed based on Eq. (111), as shown in step #35 in FIG. 12, in the third generation CT apparatus, or is reconstructed based on Eq. (511), as shown in step #435 in FIG. 17, in the fourth generation CT apparatus.

In step #630, a first IB image IB(1) is reconstructed and stored. The first IB image is reconstructed based on Eq. (112), as shown in step #45 in FIG. 12, in the third generation CT apparatus, or is reconstructed based on Eq. (512), as shown in step #445 in FIG. 17, in the fourth generation CT apparatus.

In step #635, it is checked if (m+n) is larger than a scanned maximum slice number. If NO in step #635, an (m+n)th image is reconstructed and stored in step #640, and the flow returns to step #635. In this case, only pixels in one line at the position of the horizontal ROI cursor are reconstructed. The (m+n)th image is reconstructed, as shown in steps #55 to #70 in FIG. 13, in the third generation CT apparatus, or is reconstructed, as shown in steps #455 to #470 in FIG. 18, in the fourth generation CT apparatus.

If it is determined in step #635 that (m+n) is larger than the scanned maximum slice number, a coronal image is reconstructed from the images stored so far by a known method, and the reconstructed image is displayed in step #645.

Note that the seventh embodiment presents the method of calculating a single MPR image. However, an axial image (including a line ROI cursor), and an MPR image may be simultaneously displayed, the line ROI cursor may be moved by a mouse, and an MPR image may be reconstructed in correspondence with the position of the line ROI cursor. In this manner, MPR images can be continuously observed.

An eighth embodiment for reconstructing a plurality of axial images, and calculating and displaying a three-dimensional display image (e.g., a surface display) from the reconstructed images will be described below. In a conventional three-dimensional display image, since the interval of axial images is large as compared to the pixels of the axial images, steps are undesirably observed in the slice thickness direction. According to this embodiment, since the interval of axial images can be shortened, a three-dimensional display image free from steps can be reconstructed.

Figure 22:
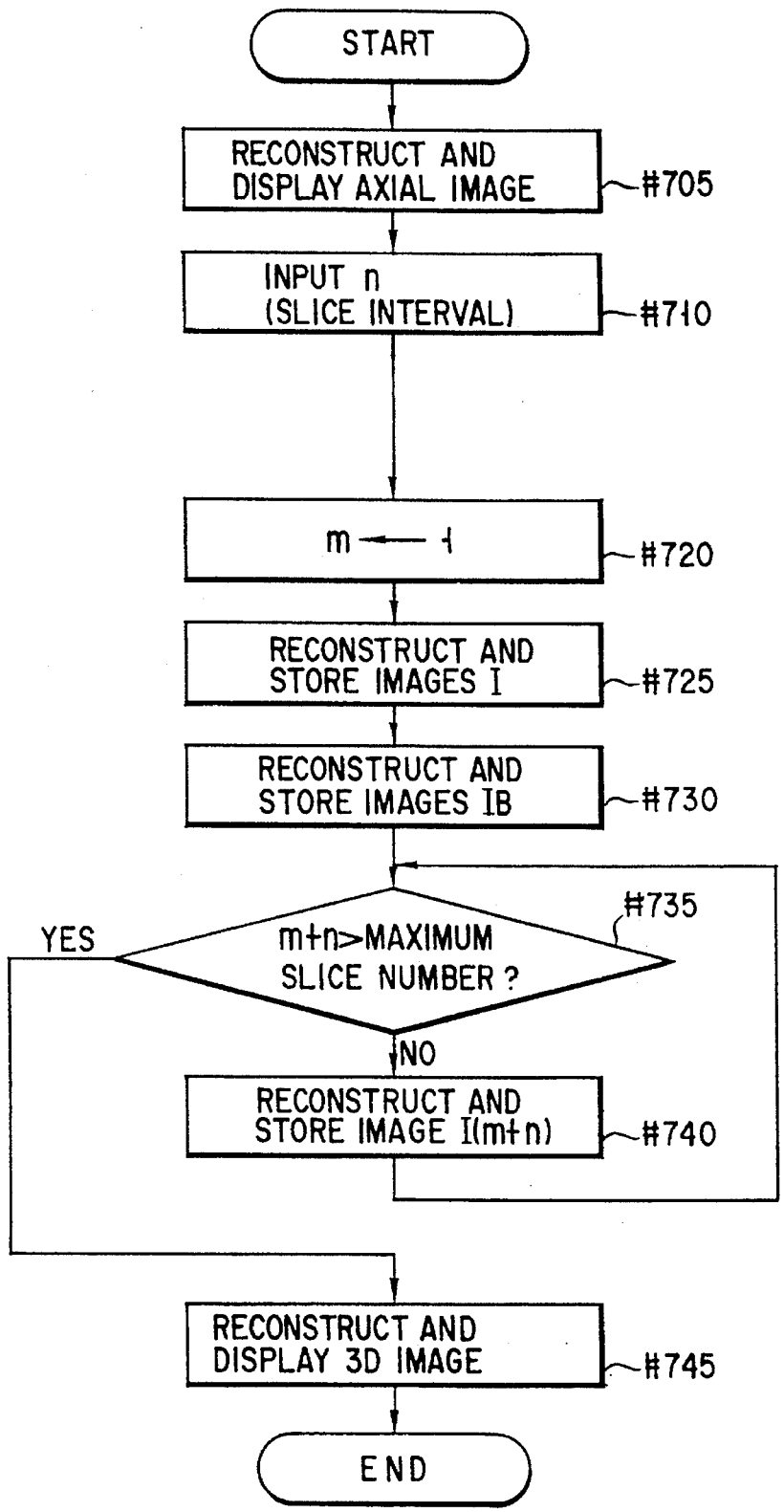
FIG. 22 is a flow chart showing an operation according to an eighth embodiment of the present invention.

FIG. 22 is a flow chart of the eighth embodiment. Referring to FIG. 22, steps #705 to #740 of reconstructing an (m+n)th image are the same as steps #605 to #640 in FIG. 21 in the seventh embodiment. However, reconstruction in steps #725, #730, and #740 are performed for all pixels. In place of reconstruction of a coronal image in step #645, a three-dimensional display image is calculated from the stored images by a known method, and the calculated image is displayed in step #745.

Note that the seventh and eighth embodiments can be similarly applied to the CT apparatus of both the R/R system and the S/R system.

In each of the above-mentioned embodiments, each slice and projection image are present at an identical position. However, even when the positions of each slice and projection image are shifted from each other, the above-mentioned embodiments can be practiced by modifying equations.

Furthermore, even when the interval of slice positions does not correspond to an integer multiple of the interval of projection positions, the present invention can be similarly practiced by modifying equations. Therefore, in the seventh embodiment and in the eighth embodiment as a modification of the seventh embodiment, the interval of slice positions can be adjusted to the pitch of pixels of an axial image.

Each of the above embodiments relates to an embodiment for continuously reconstructing a large number of tomographic images from a large amount of projection data acquired by a helical scan. However, the invention related to interpolation or extrapolation of virtual view data in the above embodiments can also be applied to a case wherein tomographic images are reconstructed one by one. Thus, a ninth embodiment related to reconstruction of a single tomographic image will be described below. Although the ninth embodiment will exemplify the third generation X-ray CT apparatus, it can be similarly applied to other system, e.g., the fourth generation X-ray CT apparatus.

The principle of the ninth embodiment will be described below. Since various definitions about projection data are the same as those in the first embodiment, a detailed description thereof will be omitted.

In this embodiment, reconstruction is executed based on Eqs. (28) and (29) in the first embodiment. Although the overall apparatus arrangement of this embodiment is the same as that of the first embodiment shown in FIG. 10, some circuits of the image reconstruction unit are different from those of the first embodiment. More specifically, since continuous reconstruction is not performed, the intermediate data calculating circuit 40 and the intermediate data memory 39 of the image reconstruction unit shown in FIG. 11 are omitted.

Figure 23:
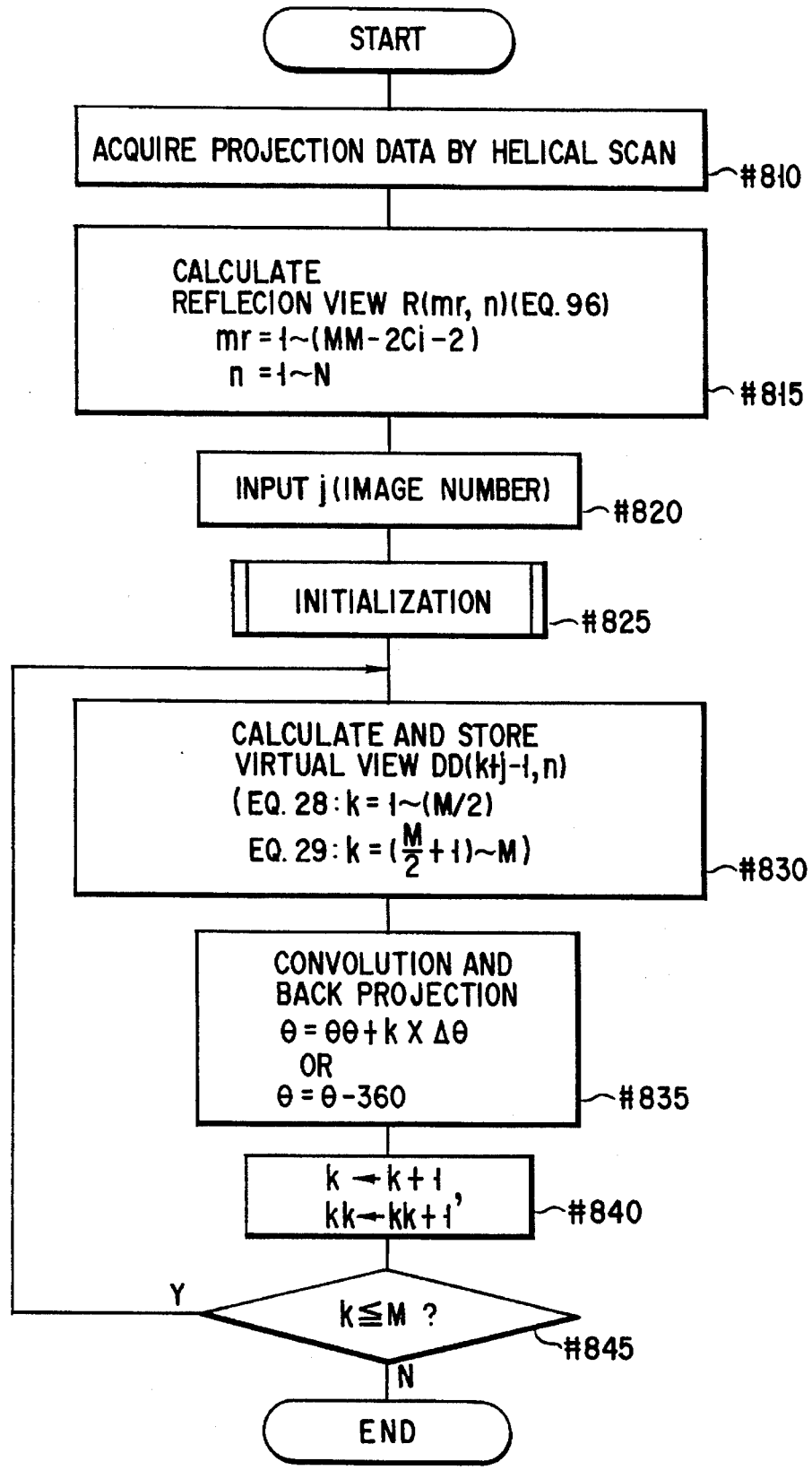
FIG. 23 is a flow chart showing an operation according to a ninth embodiment of the present invention.

The operation of the ninth embodiment will be described below with reference to FIG. 23. In step #810, a helical scan is performed to acquire projection data. The projection data are preprocessed by the preprocessing circuit 30, and are then stored in the raw data memory 32.

Upon completion of the scan or after a predetermined amount of raw data are acquired, reflection view data R(mr,n) are calculated based on Eq. (96), and are stored in the reflection view memory 38 in step #815.

In step #820, a number "j" of an image to be reconstructed is input.

In step #825, initialization is executed. FIG. 24 shows the details of initialization. More specifically, "1" is set in parameters "k" and "kk" in step #855, and the reconstructed image memory 50 is cleared in step #860. In step #865, θθ is calculated as follows in accordance with the image number "j":

$$\theta\theta = (j-1) \times \Delta\theta - \{\text{an integer part of } (j \times \Delta\theta/360)\} \times 360 \quad (150)$$

In step #830, the virtual view calculating circuit 41 calculates virtual view data of the first to Nth channels of the (k+j−1)th view. In this case, if k=1 to M/2, Eq. (28) is used; if k=M/2+1 to M, Eq. (29) is used. The calculated virtual projection data are stored at the (kk,n)th address of the virtual view memory 43.

The virtual view data calculated in step #830 are transferred to the CONV circuit 42, which executes a convolution calculation of the virtual view data, in step #835. Thereafter, the BP circuit 44 executes a back projection calculation of the convolution result. The projection angle θ in this case is given by θ=θθ+k×Δθ. However, if Δ≧360, θ=θ−360 is set.

In step #840, the parameters "k" and "kk" are updated.

in step #845, it is checked if k≦M. If k≦M, the flow returns to step #830 to repeat calculation of virtual view data. However, if k>M, reconstruction ends.

Thereafter, the reconstructed image is multiplied with a contrast scale to be converted into a CT image, and the converted image is displayed.

As described above, according to the ninth embodiment, since a virtual view at a slice position is calculated by a linear interpolation using not only an interpolation but also an extrapolation, the virtual view can be calculated using projection data and reflection data near the slice position. Therefore, an image, which is less blurred in the Z axis direction, and has less nonuniformity of the blur, can be reconstructed.

The ninth embodiment relates to a so-called fan direct method for directly reconstructing projection data (fan data) acquired based on a fan beam. A tenth embodiment, in which the principle of the ninth embodiment is applied to a method of reconstructing an image by converting fan data into parallel data (to be referred to as fan/parallel conversion hereinafter), will be described below.

First, fan/parallel conversion in the fixed position scan will be described below. If the number of views of fan projection data is sufficiently large, parallel beams can be acquired therefrom. The projection angle of a p-th view is $p \times \Delta\theta$, and a set of beams parallel to the center line of the p-th view will be refereed to as a parallel view hereinafter. The number of channels per view is represented by N. Projection data PA(p,q) of the q-th channel of the p-th parallel view is given by:

$$PA(p,q) = D(ppi,q) \times (1-ppp) + D(ppi+1,q) \times ppp \quad (151)$$

where $$pp = p + (N+1-2q) \times bb \quad (152)$$

ppi: an integral part of pp
ppp: a decimal part of pp $$bb = \Delta\alpha/(2 \times \Delta\theta) \quad (153)$$

A set of PA(p,q) obtained when "p" is constant, and q=1 to N is the p-th view of parallel beams. The p-th view corresponds to a set of projection data on an oblique line on a cynogram, as shown in FIG. 25.

Fan/parallel conversion in the helical scan will be described below. In the helical scan, since the gantry position is moved during rotation of an X-ray beam, no parallel beams are present. However, beams satisfying the relationships given by Eqs. (151) to (153) will be referred to as parallel beams hereinafter for the sake of simplicity.

Figure 25:
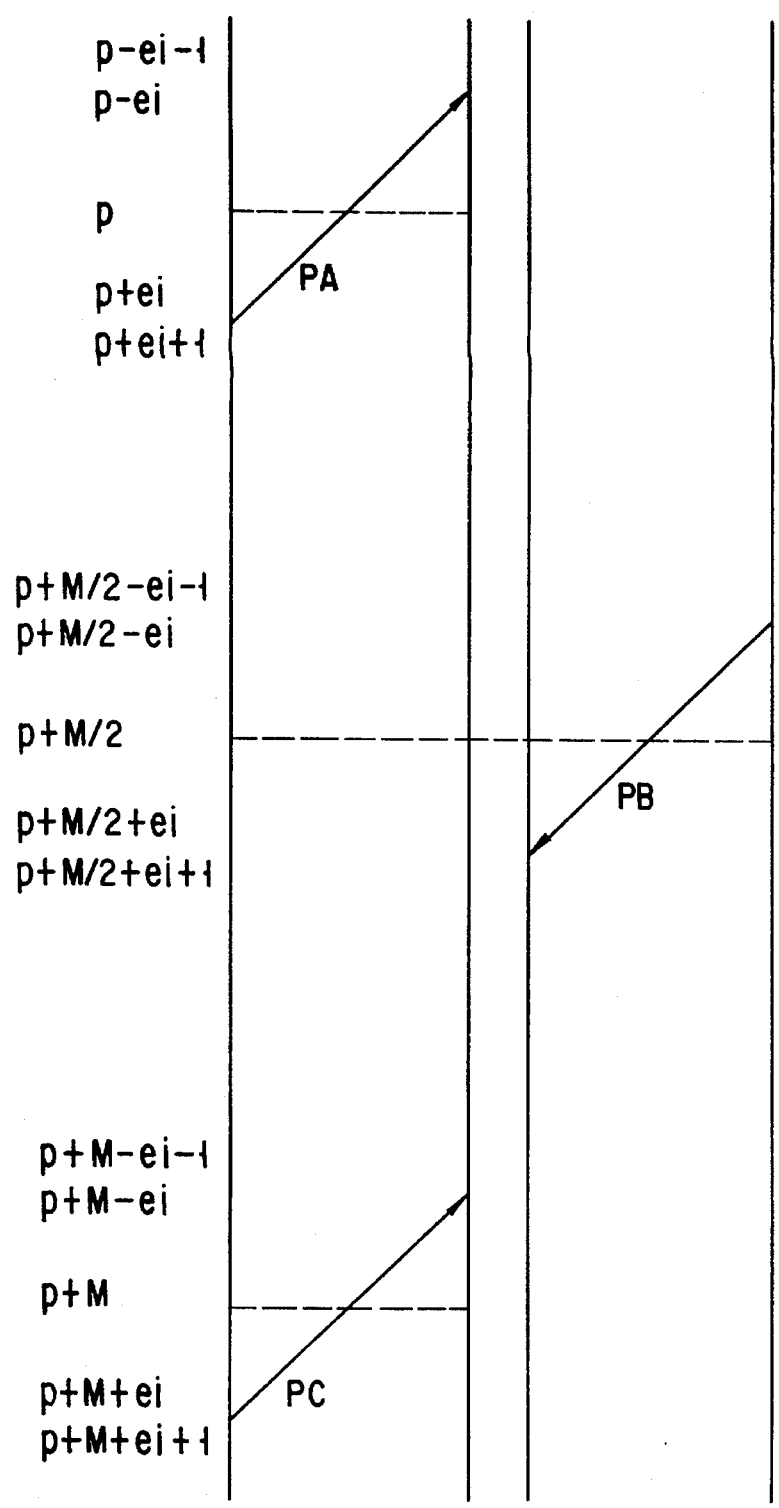
FIG. 25 is a cynogram showing fan/parallel conversion in a fixed position scan to explain the principle of a tenth embodiment.

As shown in FIG. 25, a parallel beam is present at a position separated by 180°. If this beam is represented by PB(p,q), PB(p,q) is given by:

$$PB(p,q) = PA(p+M/2, N-q+1) \quad (154)$$

Similarly, if a parallel beam at a position advanced by 360° is represented by PC(p,q), PC(p,q) is given by:

$$PC(p,q) = PA(p+M,n) \quad (155)$$

Calculation of virtual projection data at a slice position $p+(m-1)/2$ will be described below. As in the first embodiment, virtual view data of a slice are calculated by linearly interpolating or extrapolating two parallel beams as close to the slice as possible in accordance with the distance between the beams and the slice position. Therefore, if the positions of parallel beams PA and PB are represented by PAP and PBP, virtual parallel projection data PD(p,q) on the slice is given by:

$$PD(p,q) = [PA(p,q) \times \{PBP(p,q) - SP\} + \quad (156)$$

$$PB(p,q) \times \{SP - PAP(P,Q)\}]/\{PBP(p,q) - PAP(p,q)\}$$

where $p = j$ to $j+M/2$ $n = 1$ to $N$

As in the ninth embodiment, an image to be reconstructed using 180° virtual views having virtual views of number "j" to number $j+M/2-1$ is defined as a j-th image (j=ei+1 to MM−M−ei−1). The following parameters are introduced.

$$r = p - j + 1 \quad (157)$$

where r=1 to M/2

Therefore, the following relationship is obtained:

$$p = r + j - 1 \quad (158)$$

Therefore, Eq. (156) is modified as:

$$PD(r + j - 1, q) = \{PA(p, q) \times H4(r, q) + PB(p, q) \times \quad (159)$$

$$H5(r, q)\}/\{(M/2) - (N + 1 - 2q) \times aa\}$$

where r=1 to M/2
where $$H4(r,q) = r - \tfrac{1}{2} - (N+1-2q) \times bb \quad (160)$$

$$H5(r,q) = (M+1)/2 - r - (N+1-2q) \times bb \quad (161)$$

The arrangement of the tenth embodiment is the same as that of the ninth embodiment. The reflection view calculating circuit 36 can calculate parallel beams by changing parameters. The reflection view memory 38 stores parallel beam data. These circuits are controlled by the CPU 34.

Figure 26:
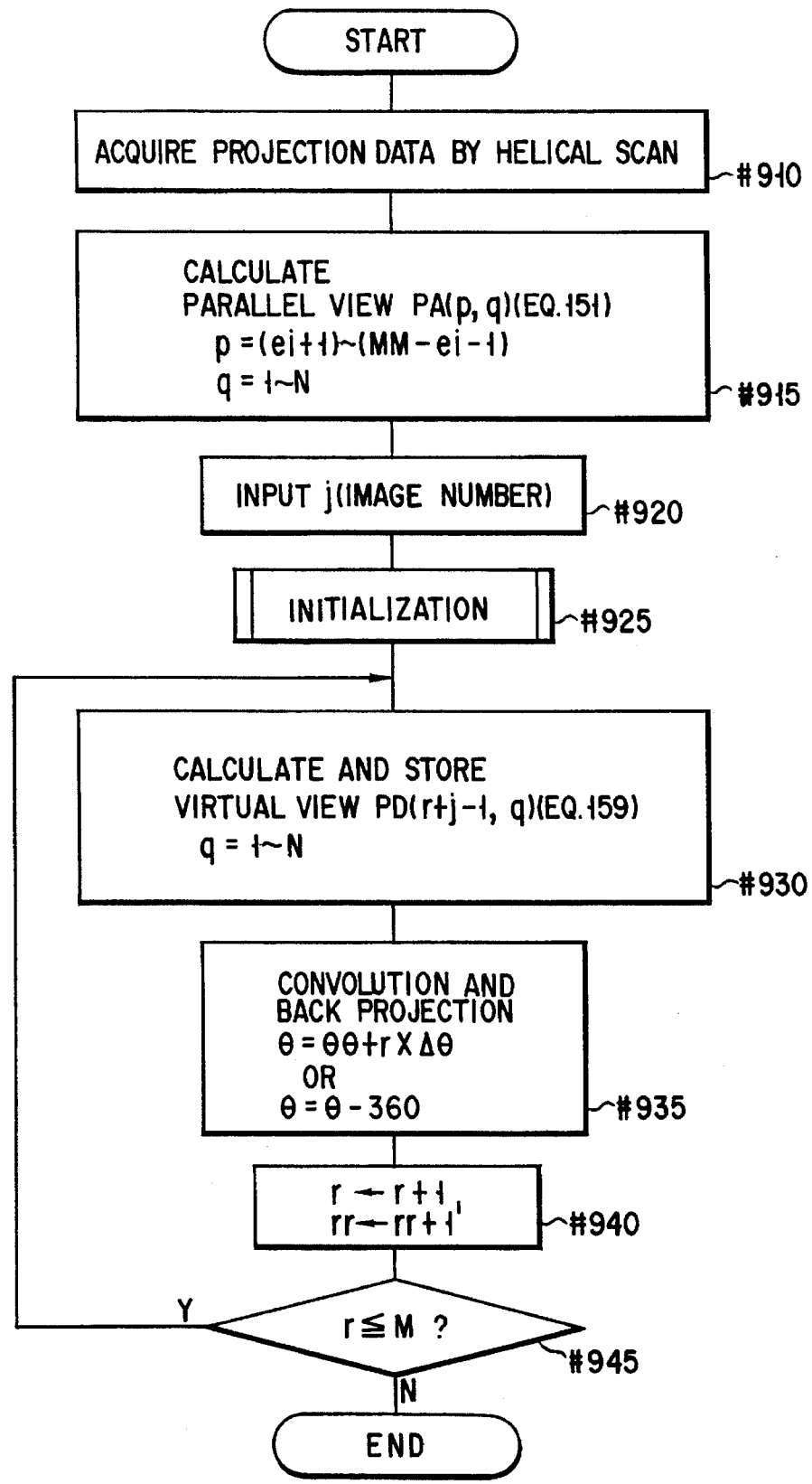
FIG. 26 is a flow chart showing an operation according to a tenth embodiment of the present invention.

FIG. 26 is a flow chart showing a reconstruction operation according to the tenth embodiment.

In step #910, a helical scan is performed to acquire projection data. The projection data are preprocessed by the preprocessing circuit 30, and the preprocessed data are stored in the raw data memory 32.

Upon completion of the scan or after a predetermined amount of raw data are acquired, parallel beam data PA(p,q) is calculated based on Eq. (151), and is stored in the reflection view memory 38 in step #915.

In step #920, a number "j" of an image to be reconstructed is input.

In step #925, initialization is executed. FIG. 27 shows the details of initialization. "1" is set in parameters "r" and "rr" in step #955, and the reconstructed image memory 50 is cleared in step #960. In step #965, θθ is calculated based on Eq. (150) in accordance with the image number "j".

In step #930, the virtual view calculating circuit 41 calculates virtual parallel projection data of the first to N-th channels of an (r+j−1)th view on the basis of Eq. (159). The calculated virtual view data are stored at the (rr,q)th address of the virtual view memory 43.

The virtual view data calculated in step #930 are transferred to the CONV circuit 42, which executes a convolution calculation of the virtual view data, in step #935. Thereafter, the BP circuit 44 executes a back projection calculation of the convolution result. The projection angle θ in this case is given by $\theta = \theta\theta + k \times \Delta\theta$. However, if $\theta \geq 360$, $\theta = \theta - 360$ is set.

In step #940, the parameters "r" and "rr" are updated.

In step #945, it is checked if r≦M. If ≦M, the flow returns to step #930 to repeat calculation of parallel beam data. If r>M, the reconstruction ends.

Thereafter, the reconstructed image is multiplied with a contrast scale to be converted into a CT image, and the converted image is displayed.

As described above, according to the tenth embodiment, even in the method wherein virtual view data are interpolated to obtain 360° projection data at a slice position after fan data are converted into parallel data, and the projection data are subjected to convolution and back projection calculations to reconstruct an image, since virtual view data at the slice position are calculated by not only a linear interpolation but also a linear extrapolation, the same effect as in the ninth embodiment can be obtained.

In the ninth and tenth embodiments, the third generation X-ray CT apparatus has been exemplified. However, these embodiments can be similarly applied to apparatuses of other systems, e.g., the fourth generation CT apparatus. The interpolation or extrapolation is not limited to a linear interpolation or a linear extrapolation, but may use a higher-order interpolation or extrapolation, such as a quadratic interpolation or extrapolation.

An embodiment for efficiently storing a large amount of projection data acquired by a helical scan or a continuous fixed position scan, or a large amount of image data obtained by continuous reconstruction in a small storage capacity will be described below.

Figure 28:
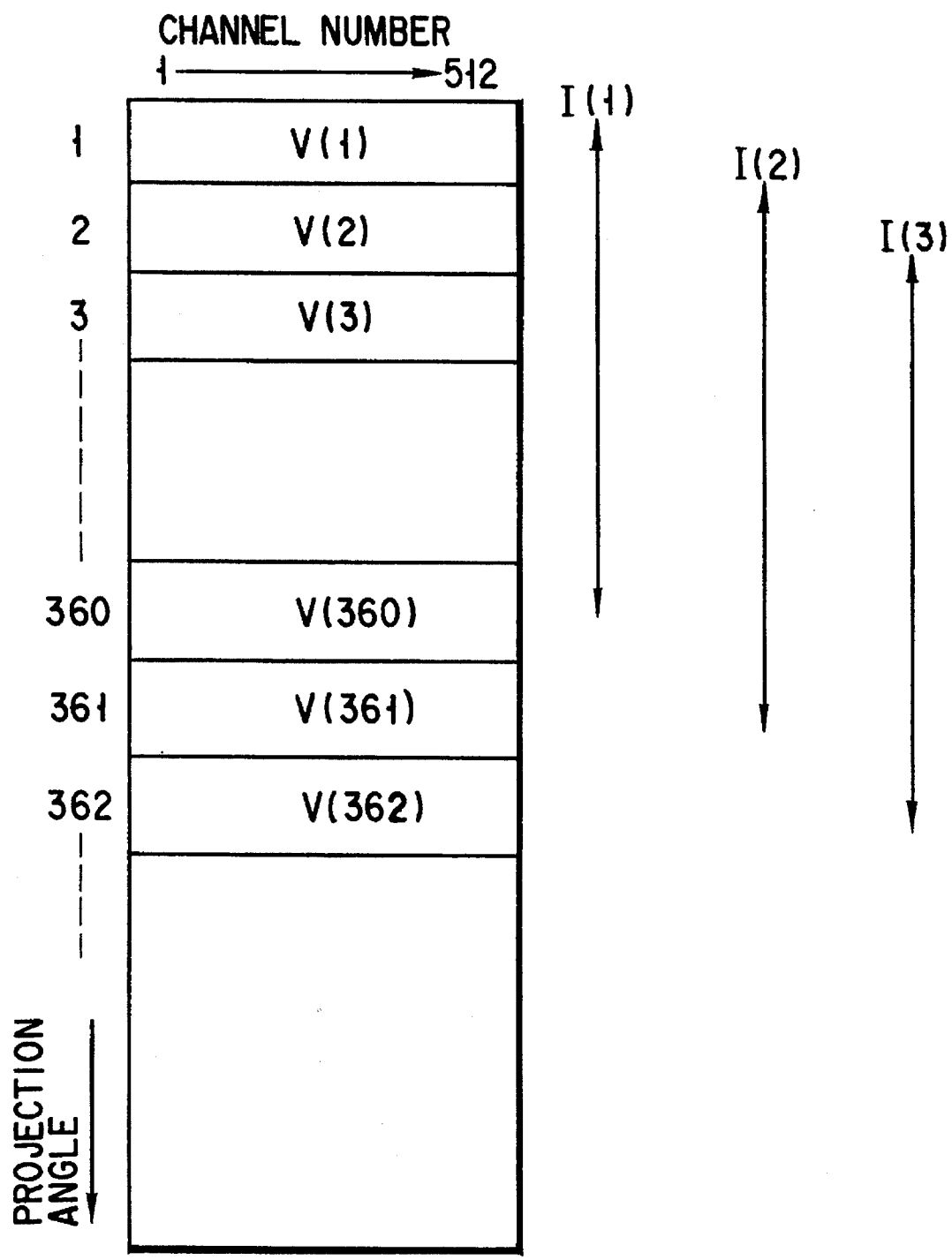
FIG. 28 illustrates views of a fixed position scan to explain the principle of an eleventh embodiment.

As an eleventh embodiment, a case will be described below wherein a large number of tomographic images are continuously reconstructed from projection data acquired by the fixed position scan. In order to explain continuous reconstruction in the fixed position scan, FIG. 28 shows a view of the fixed position scan. Since a fan beam spread in a fan shape in a slice plane is used as an X-ray beam, projection data for a large number of channels (lays) are simultaneously obtained in a single projection, and a set of projection data acquired in the single projection will be referred to as a view. For the sake of easy understanding, one view is acquired every time the projection angle (the position of an X-ray tube) changes by 1°. V(i) represents an i-th view, and the projection angle of V(i) is "i".

The first image I(1) is reconstructed by executing a convolution calculation (to be abbreviated as CONV hereinafter) and a back projection calculation (to be abbreviated as BP hereinafter) of the first view V(1) to the 360th view V(360) in units of views. Similarly, the second image I(2) is reconstructed by executing CONV and BP of the second view V(2) to the 361st view V(361) in units of views. Furthermore, the third image I(3) is reconstructed by executing CONV and BP of the third view V(3) to the 362nd view V(362) in units of views. The same applies to the subsequent images.

As is apparent from FIG. 28, the views used in reconstruction of the first image I(1) are substantially the same as those used in reconstruction of the second image I(2), except for the first view V(1) and the 361st view V(361). Since the CONV and BP calculations are linear calculations, and the first and 361st views V(1) and V(361) have the same projection angle, continuous images can be reconstructed as follows, as described in U.S. Pat. No. 4,495,645.

$$I(j+1)=I(j)+\Delta I(j+1) \quad (611)$$

$$I(j-1)=I(j)-\Delta I(j) \quad (612)$$

$$\Delta I(j)=BP[CONV\{V(j+359)-V(j-1)\}] \quad (613)$$

here I(j) is the j-th image, ΔI(j) is the subtraction image between I(j) and I(j−1), CONV is the convolution calculation, BP is the back projection calculation, and V(m)±V(n) is the calculation between the same lays of two views. Note that ΔI(j) normally assumes a small value.

Although the overall arrangement of the eleventh embodiment is the same as that of the first embodiment shown in FIG. 10, the details of the image reconstruction unit are different from those of the first embodiment.

Figure 29:
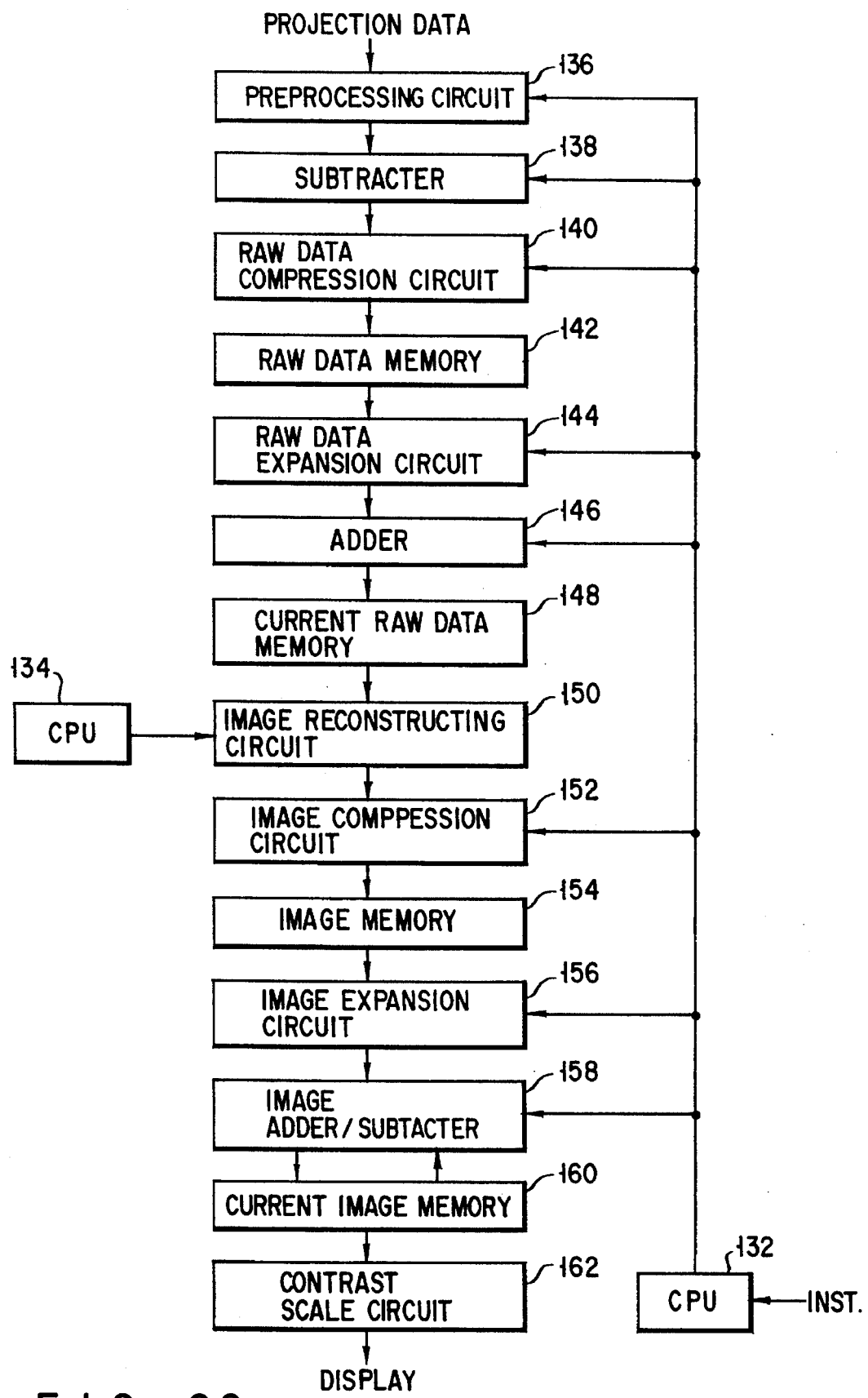
FIG. 29 is a block diagram showing the details of an image reconstruction unit according to the eleventh embodiment of the present invention.

FIG. 29 shows the details of the image reconstruction unit. The entire unit is controlled by CPUs 132 and 134. An instruction signal from the console is input to the CPU 132, and projection data from the data acquisition system is input to a preprocessing circuit 136. The output from the preprocessing circuit 136 is supplied to a raw data memory 142 via a subtracter 138 and a raw data compression circuit 140. The output from the raw data memory 142 is supplied to a current raw data memory 148 via a raw data expansion circuit 144 and an adder 146.

The output from the current raw data memory 148 is supplied to an image memory 154 via an image reconstructing circuit 150 and an image compression circuit 152. The output from the image memory 154 is supplied to a current image memory 160 via an image expansion circuit 156 and an image adder/subtracter 158. The output from the current image memory 160 is converted into a CT image by a contrast scale circuit 162, and the converted image is displayed. Note that data output from the current image memory 160 is also supplied to the image adder/subtracter 158.

The raw data memory 142 stores a large amount of raw data (projection data) acquired by continuous scan, and comprises a large-capacity storage device such as a hard disk device. The current raw data memory 148 stores raw data in a single continuous scan, and comprises a storage device such as a RAM disk.

FIG. 30 is a block diagram showing the detailed arrangement of the image reconstructing circuit 150 shown in FIG. 29. The output from the current raw data memory 148 is supplied to a CONV circuit 64 via an interpolator 62. A calculation result from the CONV circuit 64 and an output from a parameter generating circuit 66 are supplied to a BP circuit 68. The calculation result from the BP circuit 68 is temporarily stored in an intermediate image memory 70. The output from the intermediate image memory 70 is supplied to an image synthesizing circuit 72. The output from the image synthesizing circuit 72 is supplied to the image compression circuit 152. The overall circuit is controlled by the CPU 134.

Figure 33:
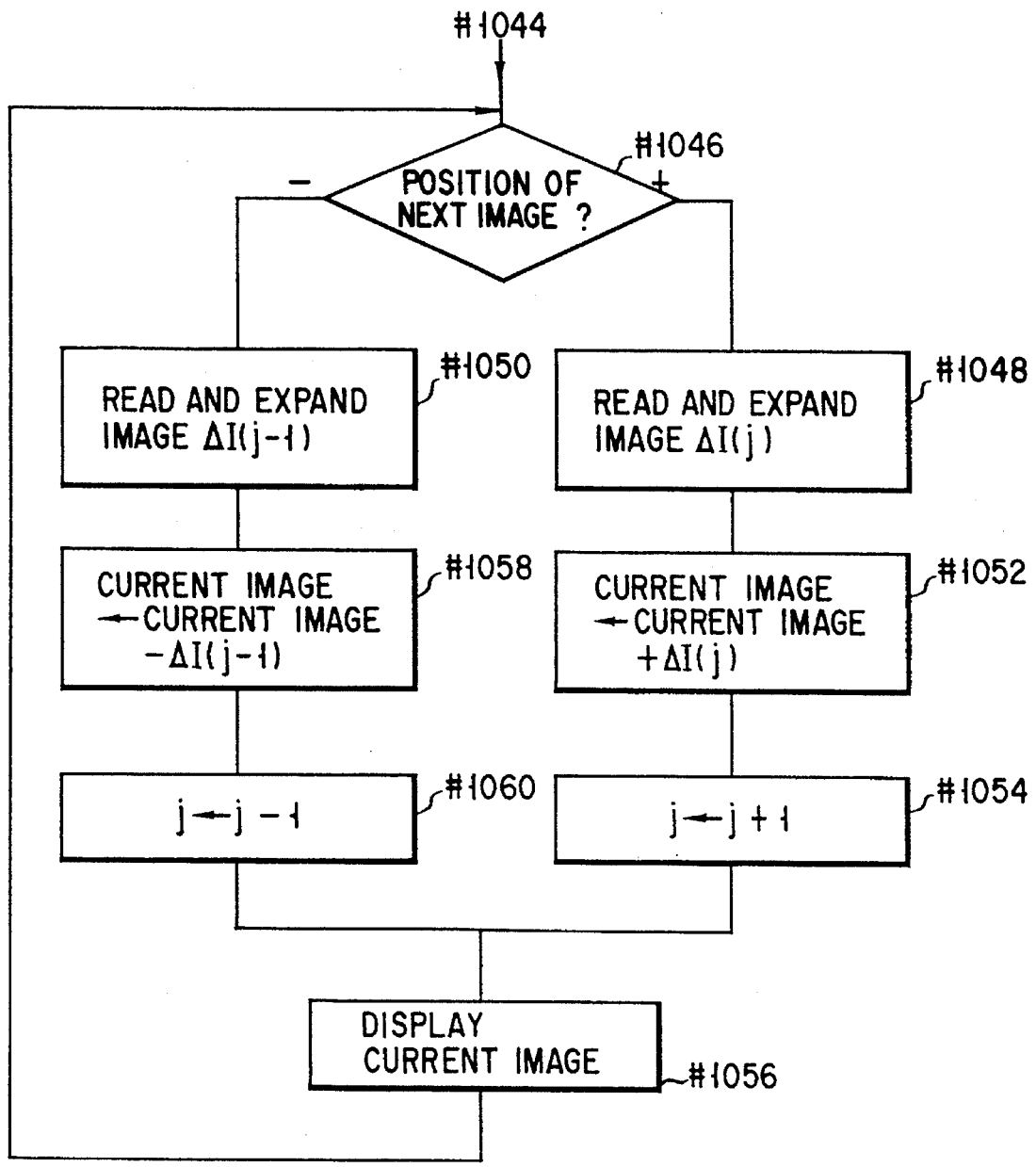
FIG. 33 is a flow chart showing a third part of the operation of the eleventh embodiment.

The operations of the eleventh embodiment will be described below with reference to FIGS. 31, 32, and 33. These operations are controlled by the CPUs 132 and 134.

In step #1010, a continuous fixed position scan is performed to acquire projection data. The projection data are preprocessed by the preprocessing circuit 136 in step #1012, and the preprocessed data are stored in the raw data memory 142 in step #1014. In the eleventh embodiment, the subtracter 138 and the raw data compression circuit 140 are not used, and the output data (raw data) from the preprocessing circuit 136 are stored in the raw data memory 142 without being compressed.

In step #1016, it is checked if the projection angle is equal to or larger than 360°. If YES in step #1016, the first to 360th views V(1) to V(360) are read out from the raw data memory 142, and are supplied to the image reconstructing circuit 150 in step #1018. In the eleventh embodiment, the raw data expansion circuit 144, the adder 146, and the current raw data memory 148 are not used, either, and the view data read out from the raw data memory 142 are directly supplied to the image reconstructing circuit 150.

In step #1020, the image reconstructing circuit 150 executes CONV and BP calculations of V(1) to V(360) in units of views, thereby reconstructing the first image I(1). In step #1022, the reconstructed first image I(1) is compressed by the image compression circuit 152, and the compressed image is stored in the image memory 154. Various compression methods have been proposed. For example, this embodiment adopts the following method. That is, a difference between pixel values (normally, 16 bits) of adjacent pixels is calculated, and if the difference falls within a range from −127 to 127, the difference value is directly stored as 8-bit data; otherwise, "80" (hexadecimal notation) is stored as a control code, and an original pixel value is stored after the control code. In this manner, since the difference value between the pixel values of adjacent pixels normally assumes a small value, the total number of bits of data can be compressed to almost half.

In step #1024, a parameter "j" is set to be 2. In step #1026, a (j−1)th view V(j−1) and a (j+359)th view V(j+359) are read out from the raw data memory 142, and are supplied to the image reconstructing circuit 150. The image reconstructing circuit 150 causes the interpolator 62 to calculate V(j+359)−V(j−1) in step #1028, and supplies the calculated difference as ΔV to the CONV circuit 64. In step #1030, the CONV circuit 64 executes a CONV calculation of ΔV, and supplies the calculation result to the BP circuit 68. The BP circuit 68 executes a BP calculation to reconstruct a j-th subtraction image.

In step #1032, the j-th subtraction image is compressed, and the compressed image is stored in the image memory 154. Various compression methods have been proposed, and any method may be adopted. In this case, reversible compression is preferable. Normally, a method different from the compression method of the first image is adopted. As an image compression method in step #1032, the following compression methods are available.

(i) The subtraction image assumes a small image. Therefore, the value is directly compressed to 8-bit data as in the compression method of the first image.

(ii) The value is compressed by directly converting it into a Huffman code.

(iii) A difference between adjacent pixels is calculated as in the first image, and is compressed by converting it into a Huffman code.

In step #1034, "j" is incremented by 1. In step #1036, whether or not "j" has reached a maximum value is discriminated to check if reconstruction of all images is completed. If images to be reconstructed still remain, the flow returns to step #1026. If reconstruction of all images is completed, the flow advances to step #1038.

In step #1038, the compressed first image stored in the image memory 154 is read out. The readout image is expanded in step #1040 to reproduce the first image. The first image is stored in the current image memory 160, and is displayed on the display 120 in step #1042. In step #1044, j=2 is set.

In step #1046, the state of a switch (not shown), arranged on the console, for instructing the position of the next image to be continuously reconstructed is read. If the switch is not depressed, the control waits. If the switch is depressed, the direction of the change is checked. If the plus direction is selected, the flow advances to step #1048; if the minus direction is selected, the flow advances to step #1050.

If the plus direction is selected, the j-th subtraction image is read out from the image memory 154, and is expanded in step #1048. In step #1052, the current image stored in the current image memory 160 is added to the expanded and reproduced j-th subtraction image, and the sum is stored in the current image memory 160 as a current image. In step #1054, "j" is incremented by 1, and the flow advances to step #1056.

If the minus direction is selected, the (j−1)th subtraction image is read out from the image memory 154, and is expanded in step #1050. In step #1058, the expanded and reproduced (j−1)th subtraction image is subtracted from the current image stored in the current image memory 160, and the difference is stored in the current image memory 160 as a current image. In step #1060, "j" is decremented by 1, and the flow advances to step #1056.

In step #1056, the current image is displayed, and the flow returns to step #1046.

As described above, according to the eleventh embodiment, the first (or last) slice image is reconstructed and stored using stored raw data. Then, subtraction images from slightly separated positions are continuously reconstructed, and are stored. Since the subtraction images assume small values, they can be compressed so that it can be stored with a small storage capacity even if a reversible compression method is employed. Furthermore, when the stored subtraction images are expanded and are continuously added to the first (last) image to display sum images, continuous images can be displayed. Thus, an X-ray CT apparatus, which can reconstruct a large number of tomographic images from a large amount of projection data acquired by the continuous fixed position scan within a short period of time, and can suppress the storage capacity of reconstructed image data, can be provided.

Note that the eleventh embodiment can be modified as follows.

In the above description, a so-called real-time display operation, in which the scan, reconstruction, and display are parallelly executed to allow image observation parallel to the scan, has been exemplified. However, these operations may be executed serially. More specifically, the reconstruction may be performed after all slices are scanned, and the display may be performed after all tomographic images are reconstructed. In the case of parallel processes as well, since the images are stored, the images may be displayed and observed after the scan is completed.

In the above description, only the first image is stored not as a subtraction image but as a complete image, and the second and subsequent images are stored as subtraction images. Alternatively, the first and last two images or images separated by a predetermined number of images may be stored as complete images, and images between the complete images may be stored as subtraction images.

In the above description, subtraction images in units of images are stored. However, subtraction images of designated images or separated by a designated number of images of the reconstructed images may be stored. The subtraction images separated by the designated number of images can be obtained by adding subtraction images therebetween.

The compression method of a subtraction image is not limited to the above-mentioned method, and various modifications may be made.

A twelfth embodiment will be described below with reference to FIGS. 34 and 35. In the eleventh embodiment, raw data are stored without being compressed, and subtraction images of reconstructed images are compressed and stored. The twelfth embodiment in which raw data are compressed and stored, and reconstructed images are stored without being compressed will be described below. Although the arrangement of the twelfth embodiment is the same as that of the eleventh embodiment, functions (process circuits), which are not used in the eleventh embodiment, are used in the twelfth embodiment. The operations of the twelfth embodiment are also controlled by the CPUs 132 and 134.

In step #1100, a continuous scan is started to acquire projection data V(1) of the first view. In step #1102, a preprocess is executed. In step #1104, the subtracter 138 does not perform subtraction, and sets the projection data V(1) of the first view in CV1. In step #1106, the raw data compression circuit 140 does not perform compression, and stores the projection data CV1 of the first view V(1) in the raw data memory 142. In step #1108, k=2 is set.

In step #1110, data of a k-th view V(k) are acquired. In step #1112, a preprocess is executed. In step #1114, the subtracter 138 performs subtraction processing to calculate ΔV(k)=V(k)–CV1, and supplies ΔV(k) to the raw data compression circuit 140. In step #1116, the projection data V(k) of the k-th view is set in CV1.

In step #1118, the raw data compression circuit 140 compresses ΔV(k), and stores compressed data in the raw data memory 142. As this compression method, although various methods can be used, a reversible compression method must be adopted. For example, the following compression methods are available.

(i) The subtraction image assumes a small image. Therefore, the value is directly compressed to 8-bit data as in the compression method of the first image in the eleventh embodiment.

(ii) The value is compressed by directly converting it into a Huffman code.

(iii) A difference between adjacent data is calculated, and is compressed by converting it into a Huffman code.

In step #1120, "k" is incremented by 1. In step #1122, it is checked if the scan is to be continued. If the scan is to be continued, the flow returns to step #1110; otherwise, the flow advances to step #1124.

The first view V(1) is read out from the raw data memory 142 in step #1124, and is set in CV2 in step #1126. In step #1128, the first view V(1) is stored in the current raw data memory 148. In step #1130, k=2 is set.

The raw data expansion circuit 144 reads out compressed ΔV(k) stored in the raw data memory 142 in step #1132, and expands the readout data in step #1134. In step #1136, CV2+ΔV(k) is calculated, and the sum is set in CV2. CV2 calculated in step #1136 is stored in the current raw data memory 148 as V(k) in step #1138.

In step #1140, "k" is incremented by 1. In step #1142, it is checked if processes are completed for all "k"s. If "k" does not reach a maximum value, the flow returns to step #1132; if the processes are completed for all "k"s, the flow enters a reconstruction process. The reconstruction process is the same as that in the eleventh embodiment, and step #1018 and subsequent steps in FIG. 31 are executed.

As described above, according to the twelfth embodiment as well, since differences of view data of the second and subsequent views are compressed and stored, an X-ray CT apparatus, which can reduce the storage capacity, can be provided as in the eleventh embodiment.

Note that the twelfth embodiment can be modified as follows.

In the above description, the scan, compression/storage of raw data, expansion of compressed raw data, reconstruction, and display are serially executed. However, these operations may be executed in parallel. Thus, since image observation can be performed parallel to the scan, a so-called real-time display operation can be realized. Since raw data are stored, images may be reconstructed again using another reconstruction function after the scan is completed.

In the eleventh and twelfth embodiments, both raw data and reconstructed images are stored. However, either of raw data or images may be stored, and the other one may not be stored. Furthermore, in the eleventh and twelfth embodiments, either of raw data or reconstructed images are compressed and stored. However, both the raw data and reconstructed images may be compressed and stored.

A thirteenth embodiment of the present invention will be described below. In the eleventh and twelfth embodiments, the fixed position scan continuous reconstruction method has been described. The thirteenth embodiment relates to a helical scan continuous reconstruction method. In this embodiment, the direction (slice direction) perpendicular to a tomographic image, i.e., the moving direction of an object to be examined is defined as a Z axis. The helical scan reconstruction method includes a method using 720° views and a method using reflection beams. In this embodiment, the method using 720° views will be described below. However, the present invention can be similarly applied to the method using reflection beams.

The basic principle of this continuous reconstruction method will be described below.

If an image at a given slice position is represented by an m-th image mI, the m-th image can be obtained in such a manner that projection data within a projection angle range of 720° before and after the slice position as the center are linearly interpolated to obtain projection data at the slice position, and the projection data are reconstructed. This reconstruction can be the same as a normal reconstruction process in the helical scan.

As image at a slice position adjacent to this slice position is obtained by the following process unique to the present invention, which is different from the above-mentioned normal process. Assume that the slice position number increases as the scan progresses. An image is reconstructed from 360° projection data acquired temporally before the slice position of the m-th image (in a direction to decrease the slice position number) without interpolation, and is defined as an mB-th image. Similarly, an image is reconstructed from 360° projection data acquired temporally after the slice position of the m-th image (in a direction to increase the slice position number) without interpolation, and is defined as an mF-th image. The moving distance of a gantry while an X-ray tube and an X-ray detector are rotated by a unit projection angle in order to acquire 360° projection data is represented by "d", and an image at a slice position temporally after the slice position of the m-th image by the distance "d" is defined as an (m+1)th image. In the following description, assume that the slice position coincides with the projection position (gantry position) for the sake of simplicity.

The following images are calculated to obtain the (m+1)th image:

$$(m+1)BI = mBI + BP[CONV(a-b)] \quad (191)$$

$$(m+1)FI = mFI + BP[CONV(c-a)] \quad (192)$$

where

BP: back projection calculation

CONV: convolution calculation a: projection data at slice position of (m+1)th image b: projection data at slice position before "a" by 360° c: projection data at slice position after "a" by 360°

In the present invention, the (m+1)th image is calculated as follows using Eqs. (191) and (192):

$$(m+1)I = mI + DW \times \{(m+1)FI - (m+1)BI\} \quad (193)$$

where

DW: inclination of linear interpolation

Similarly, the following images are calculated in order to obtain an (m−1)th image:

$$(m-1)BI = mBI + BP[CONV(e-d)] \quad (194)$$

$$(m-1)FI = mFI + BP[CONV(d-f)] \quad (195)$$

where d: projection data at slice position of (m−1)th image e: projection data at slice position before "d" by 360° f: projection data at slice position after "d" by 360°

In the present invention, the (m−1)th image is calculated as follows using Eqs. (194) and (195):

$$(m-1)I = mI - DW \times (mFI - mBI) \quad (196)$$

Since the projection data "a", "b", and "c" have the same projection angle, and the projection data "d", "e", and "f" have the same projection angle, if mFI=mBI=mFBI is defined, the following equation is obtained from Eqs. (191) and (192):

$$\begin{aligned}(m+1)FBI &= (m+1)FI - (m+1)BI \quad (197)\\ &= mFI + BP[CONV(c-a)] - \\ & \quad mBI - BP[CONV(a-b)] \\ &= mFI - mBI + BP[CONV(c-a)] - \\ & \quad BP[CONV(a-b)] \\ &= mFBI + BP[CONV(c+b-2a)]\end{aligned}$$

Similarly, the following equation is obtained from Eqs. (194) and (195):

$$\begin{aligned}(m-1)FBI &= (m-1)FI - (m-1)BI \quad (198)\\ &= mFI + BP[CONV(d-f)] - \\ & \quad mBI - BP[CONV(e-d)] \\ &= mFI - mBI + BP[CONV(d-f)] - \\ & \quad BP[CONV(e-d)] \\ &= mFBI - BP[CONV(2d-f-e)]\end{aligned}$$

When Eqs. (197) and (198) are respectively substituted into Eqs. (193) and (196), images at continuous slice positions can be reconstructed by the following equations:

$$(m+1)I = mI + DW \times (m+1)FBI \quad (199)$$

$$(m-1)I = mI - DW \times mFBI \quad (200)$$

In this manner, at each slice position, a tomographic image can be reconstructed by reconstructing only a difference from projection data at the slice position where a tomographic image has already been reconstructed, and neither interpolation nor reconstruction of 360° projection data in units of slice positions are required. Therefore, images at continuous slice positions in the helical scan can be calculated at high speed with a small calculation amount. When the slice position of the m-th image is continuously changed using, e.g., a mouse, images at the respective slice positions can be continuously displayed, and a region of interest inside a body can be continuously observed.

Symbols are replaced as follows:

$$I(j\pm1) = (m\pm1)I \quad (208)$$

$$I(j) = mI \quad (209)$$

$$FBI(j\pm1) = (m\pm1)FBI \quad (210)$$

$$FBI(j) = mFBI \quad (211)$$

$$\begin{aligned}\Delta I(j\pm i) &= DW \times (m\pm1)FBI \quad (212)\\ &= DW \times FBI(j\pm1)\end{aligned}$$

$$\begin{aligned}\Delta I(j) &= DW \times mFBI \quad (213)\\ &= DW \times FBI(j)\end{aligned}$$

-continued $$\begin{aligned}\Delta FBI(j+1) &= BP[CONV\{P(j+719) + \quad (214)\\ & \quad P(j-1) - 2 \times P(j+359)\}]\end{aligned}$$

$$\begin{aligned}\Delta FBI(j) &= BP[CONV\{P(j+718) + \quad (215)\\ & \quad P(j-2) - 2 \times P(j+358)\}]\end{aligned}$$

Therefore, Eqs. (199), (200), (197), and (198) are respectively rewritten as:

$$I(j+1) = I(j) + \Delta I(j+1) \quad (216)$$

$$I(j-1) = I(j) - \Delta I(j) \quad (217)$$

$$\Delta I(j+1) = DW \times FBI(j+1) \quad (218)$$

$$\Delta I(j) = DW \times FBI(j) \quad (219)$$

From Eqs. (216) to (219), the following equations can be derived:

$$FBI(j+1) = FBI(j) + \Delta FBI(j+1) \quad (220)$$

$$FBI(j-1) = FBI(j) - \Delta FBI(j) \quad (221)$$

Figure 36:
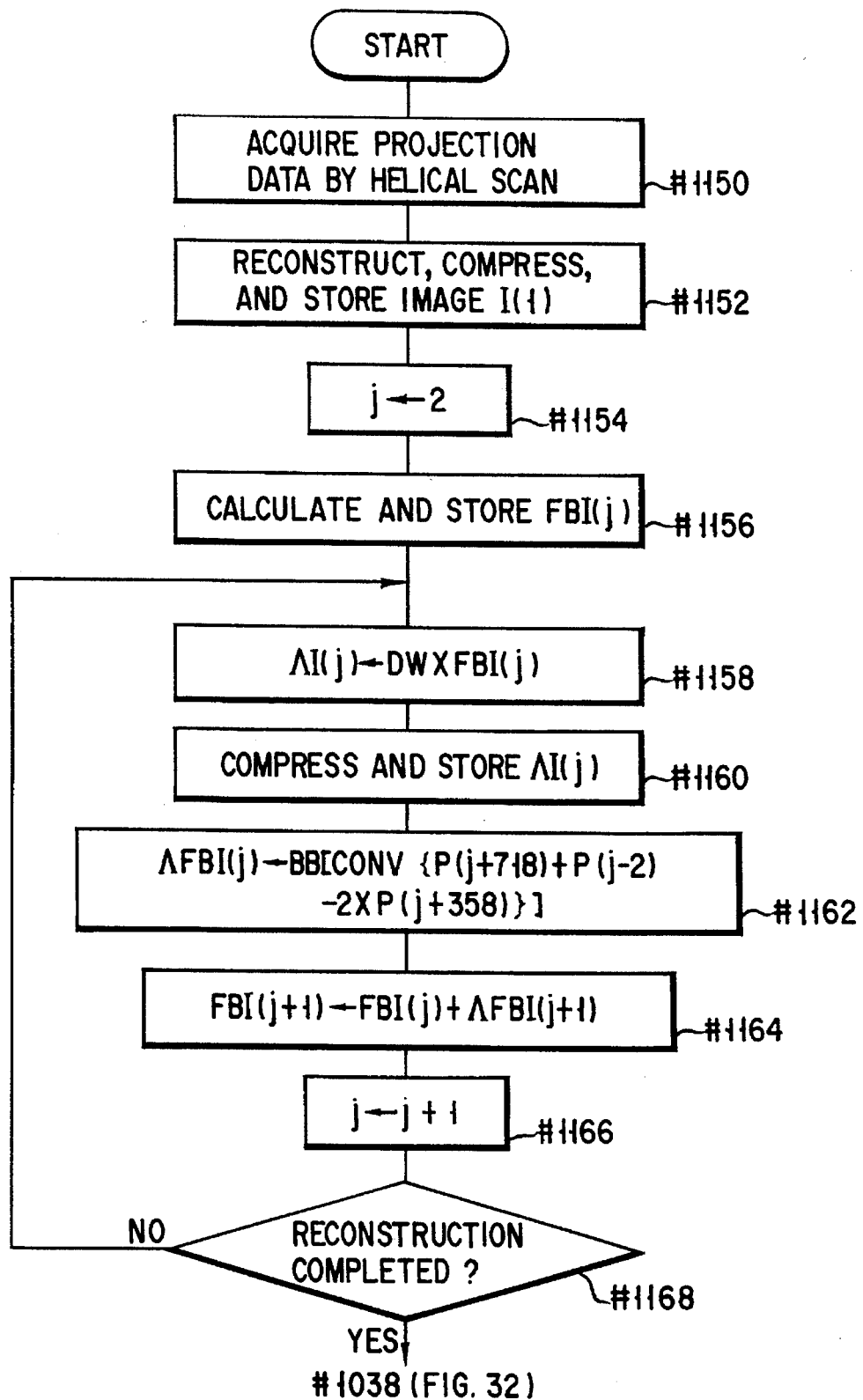
FIG. 36 is a flow chart showing an operation according to a thirteenth embodiment of the present invention.

The operations of the thirteenth embodiment will be described below with reference to FIG. 36. Since the arrangement of the thirteenth embodiment is the same as that of the eleventh embodiment shown in FIGS. 29 and 30, a detailed description thereof will be omitted. These operations are also controlled by the CPUs 132 and 134.

In step #1150, projection data are acquired by a helical scan.

In step #1152, an interpolation, CONV, and BP are normally executed to reconstruct the first image I(1). The reconstructed image is compressed, and is stored in the image memory 154. In step #1154, j=2 is set.

In step #1156, FBI(j) is calculated according to Eq. (210), and is stored in the intermediate image memory 70.

In step #1158, the image synthesizing circuit 72 calculates ΔI(j) according to Eq. (219). In step #1160, ΔI(j) is compressed, and is stored in the image memory 154. In step #1162, ΔFBI(j) is calculated based on Eq. (215). In step #1164, FBI(j+1) is calculated based on Eq. (220), and is stored in the intermediate image memory 70. In step #1166, "j" is incremented by 1.

In step #1168, it is checked if reconstruction of all images is completed. If images to be reconstructed still remain, the flow returns to step #1158. If reconstruction is completed, an image display is performed. The image display is the same as that in the eleventh embodiment. More specifically, processes in step #1038 and subsequent steps in FIG. 32 are executed.

As described above, according to the thirteenth embodiment, an X-ray CT apparatus, which can reconstruct a large number of tomographic images from projection data acquired by the helical scan using 720° views within a short period of time, and can suppress the storage capacity of data necessary for reconstruction, can be provided.

Note that the thirteenth embodiment can be modified as follows as in the eleventh embodiment.

In the above description, a so-called real-time display operation, in which the scan, reconstruction, and display are parallelly executed to allow image observation parallel to the scan, has been exemplified. However, these operations may be executed serially. More specifically, the reconstruction may be performed after all slices are scanned, and the display may be performed after all tomographic images are reconstructed. In the case of parallel processes as well, since the images are stored, the images may be displayed and observed after the scan is completed.

In the above description, only the first image is stored not as a subtraction image but as a complete image, and the second and subsequent images are stored as subtraction images. Alternatively, the first and last two images or images separated by a predetermined number of images may be stored as complete images, and images between the complete images may be stored as subtraction images.

In the above description, subtraction images in units of images are stored. However, subtraction images of designated images or separated by a designated number of images of the reconstructed images may be stored. The subtraction images separated by the designated number of images can be obtained by adding subtraction images therebetween.

Furthermore, raw data may also be compressed and stored.

A fourteenth embodiment of the present invention will be described below. In the thirteenth embodiment, the helical scan continuous reconstruction method using 720° views has been described. In the fourteenth embodiment, a method using views in a range of 360°+a double fan angle 4α using reflection beams as in the first and fourth embodiments will be described below. The continuous reconstruction process in the plus direction in the method using reflection beams is described in detail in the first and fourth embodiments. The basic principle of this continuous reconstruction process is expressed by the following equations:

$$IB(j+1) = IB(j) - BP[CONV\{-DE(j,n) + \quad (113)/(513)/(222)$$
$$RPE(j,n) - DF(j+M,n) +$$
$$RMF(j+M,n)\}] +$$
$$BP[CONV\{-DE(j+(M/2),n) +$$
$$RPE(j+(M/2),n) - DF(j+M,n) +$$
$$RMF(j+(M/2),n)\}]$$

$$I(j+1) = I(j) + \Delta I(j+1) \quad (114a)/(514A)/(223)$$

The following parameters are defined:

$$\Delta IB(j+1) = BP[CONV[DE(j,n) - RPE(j,n) + \quad (224)$$
$$DF(j+M,n) - RMF(j+M,n)] +$$
$$BP[CONV\{-DE(j+(M/2),n) +$$
$$RPE(j+M/2),n) - DF(j+M/2),n) +$$
$$RMF(j+(M/2),n)\}]]$$

The Eq. (222) is rewritten as follows:

$$IB(j+1)=IB(j)+\Delta IB(j+1) \quad (225)$$

The operations of the fourteenth embodiment will be described below with reference to FIG. 37. Since the arrangement of the fourteenth embodiment is also the same as that of the eleventh embodiment shown in FIGS. 29 and 30, a detailed description thereof will be omitted. These operations are also controlled by the CPUs 132 and 134.

In step #1170, projection data are acquired by a helical scan.

In step #1172, an interpolation, CONV, and BP are normally executed to reconstruct the first image I(1). The reconstructed image is compressed, and is stored in the image memory 154. In step #1174, j=1 is set.

In step #1176, IB(j) is calculated in the same manner as in the first embodiment, i.e., based on Eq. (112), and is stored in the intermediate image memory 170.

In step #1178, the interpolator 62, the BP circuit 164, and the CONV circuit 168 calculate $\Delta I(j+1)$ according to Eq. (115) or (515). In step #1182, $\Delta I(j+1)$ is compressed, and is stored in the image memory 154.

In step #1184, $\Delta IB(j+1)$ is calculated according to Eq. (223) and is stored in the intermediate image memory 70. In step #1188, j is incremented by 1.

In step #1190, it is checked if reconstruction of all images is completed. If images to be reconstructed still remain, the flow returns to step #1178. If reconstruction is completed, an image display is performed. The image display is the same as that in the eleventh embodiment. More specifically, processes in step #1038 and subsequent steps in FIG. 32 are executed.

As described above, according to the fourteenth embodiment, a large number of tomographic images can be reconstructed using reflection beams from projection data obtained by the helical scan within a short period of time. In addition, an image of the first (or last) slice is reconstructed and stored using directly stored raw data so as to continuously reconstruct subtraction images at slightly separate positions, and the subtraction images are compressed and stored. Furthermore, the stored subtraction images are expanded, and are continuously added to the first (last) image, so that continuous images can be displayed. Thus, an X-ray CT apparatus, which can reconstruct a large number of tomographic images from a large amount of projection data acquired by the helical scan, and can suppress the storage capacity of reconstructed image data, can be provided.

Note that the fourteenth embodiment can be modified as follows as in the eleventh embodiment.

In the above description, a so-called real-time display operation, in which the scan, reconstruction, and display are parallelly executed to allow image observation parallel to the scan, has been exemplified. However, these operations may be executed serially. More specifically, the reconstruction may be performed after all slices are scanned, and the display may be performed after all tomographic images are reconstructed. In the case of parallel processes as well, since the images are stored, the images may be displayed and observed after the scan is completed.

In the above description, only the first image is stored not as a subtraction image but as a complete image, and the second and subsequent images are stored as subtraction images. Alternatively, the first and last two images or images separated by a predetermined number of images may be stored as complete images, and images between the complete images may be stored as subtraction images.

In the above description, subtraction images in units of images are stored. However, subtraction images of designated images or separated by a designated number of images of the reconstructed images may be stored. The subtraction images separated by the designated number of images can be obtained by adding subtraction images therebetween.

Furthermore, raw data may also be compressed and stored.

A fifteenth embodiment related to continuous reconstruction of half images will be described below. A continuous reconstruction process, in the plus direction, of half images will be described below. The principle of this process is as follows.

The third generation X-ray CT apparatus will be exemplified below.

FIG. 38 illustrates the relationship between projection data acquired by continuous scan of five revolutions, and reflection data obtained from the projection data by the reflection method. In FIG. 38, "m" is the view number of projection data, "mm" is the view number of virtual projection data, and the number of views per revolution (360°) is 1,440. Although not shown, the fan angle 2α is 40°, and the number of channels is 800. As described above, the first image is reconstructed using the first to 880th views, and the 881st to 1,440th reflection views. The second image is reconstructed using the second to 881st views, and the 882nd to 1,441st reflection views. An image reconstructed using the m-th to (m+879)th views and the (m+880)th to (m+1,439)th reflection views is defined as an m-th image, and is represented by $I_m$. The first image $I_1$ can be reconstructed as follows:

$$\begin{aligned} I_1 = &\ BP[CONV(V_1)] + BP\{CONV(V_2)\} + \ldots + \\ &\ BP\{CONV(V_i)\} + \ldots + \\ &\ BP\{CONV(V_{888})\} + \ldots + \\ &\ BP\{CONV(RV_{881})\} + \\ &\ BP\{CONV(RV_{882})\} + \ldots + \\ &\ BP\{CONV(RV_j)\} + \ldots + \\ &\ BP\{CONV(RV_{1440})\} \end{aligned} \quad (230)$$

where $V_i$: i-th view $RV_j$: j-th reflection view

CONV: convolution calculation

BP: back projection calculation

Similarly, the second image $I_2$ can be reconstructed as follows:

$$\begin{aligned} I_2 = &\ BP\{CONV(V_2)\} + BP\{CONV(V_3)\} + \ldots + \\ &\ BP\{CONV(V_i)\} + \ldots + BP\{CONV(V_{888})\} + \\ &\ BP\{CONV(RV_{882})\} + BP\{CONV(RV_{883})\} + \ldots + \\ &\ BP\{CONV(RV_j)\} + \ldots + BP\{CONV(RV_{1441})\} \end{aligned} \quad (231)$$

When Eq. (232) is subtracted from Eq. (231), since CONV and BP are linear calculations, the difference between the first and second images is expressed as:

$$\begin{aligned} I_2 - I_1 = &\ BP\{CONV(V_{881})\} - BP\{CONV(V_1)\} + \\ &\ BP\{CONV(RV_{1441})\} - BP\{CONV(RV_{881})\} \\ = &\ BP\{CONV(V_{881} - RV_{881})\} + \\ &\ BP\{CONV(RV_{1441})\} - BP\{CONV(V_1)\} \end{aligned} \quad (233)$$

Note that $RV_{1441}$ and $V_1$ have the same view angle, i.e., 0.25°. Therefore, Eq. (233) is modified as:

$$I_2 - I_1 = BP\{CONV(V_{881} - RV_{881})\} + BP\{CONV(RV_{1441} - V_1)\} \quad (234)$$

When Eq. (234) is modified, the second image is given by:

$$I_2 = I_1 + BP\{CONV(V_{881} - RV_{881})\} + BP\{CONV(RV_{1441} - V_1)\} \quad (235)$$

As can be understood from Eq. (235), the second image can be reconstructed by executing CONV and BP of a view obtained by subtracting the 881st reflection view from the 881st view and a view obtained by subtracting the first view from the 1,441st reflection view on the first image. As compared to Eq. (231), which requires 1,440 CONV and BP calculations, Eq. (235) requires only two subtractions and two CONV and BP calculations. Therefore, images can be reconstructed at a very high speed.

Conversely, when the first image is reconstructed from the second image, Eq. (234) is modified as:

$$\begin{aligned} I_1 = &\ I_2 - BP\{CONV(V_{881} - RV_{881})\} - \\ &\ BP\{CONV(RV_{1441} - V_1)\} \\ = &\ I_2 + BP\{CONV(RV_{881} - V_{881})\} + \\ &\ BP\{CONV(V_1 - RV_{1441})\} \end{aligned} \quad (236)$$

Equations (235) and (236) are respectively generalized as:

$$\begin{aligned} I_{m+1} = &\ I_m + BP\{CONV(V_{m+880} - RV_{m+880})\} + \\ &\ BP\{CONV(RV_{m+1440} - V_m)\} \end{aligned} \quad (237)$$

$$\begin{aligned} I_{m-1} = &\ I_m + BP\{CONV(RV_{m+879} - V_{m+879})\} + \\ &\ BP\{CONV(V_{m-1} - RV_{m+1439})\} \end{aligned} \quad (238)$$

Therefore, the (m+1)th image can be reconstructed from the m-th image according to Eq. (237), and the (m−1)th image can be reconstructed from the m-th image according to Eq. (238).

The continuous reconstruction process, in the plus direction, of a half image given by Eq. (237) will be described below.

Symbols are replaced as follows:

$$I(j+1) = I_{m+1} \quad (240)$$

$$I(j) = I_m \quad (241)$$

$$\begin{aligned} \delta I(j+1) = &\ BP[CONV\{V(j+880) - RV(j+880)\}] + \\ &\ BP[CONV\{RV(j+1440) - V(j)\}] \end{aligned} \quad (242)$$

Therefore, Eq. (237) can be rewritten as:

$$I(j+1) = I(j) + \delta I(j+1) \quad (243)$$

Therefore, when $\delta I(j)$ is processed in the same manner as the subtraction image $\Delta I(j)$ in the eleventh embodiment, the present invention can be applied to continuous reconstruction of half images.

In the thirteenth, fourteenth, and fifteenth embodiments, compression/storage of raw data is not described. However, in these embodiments, raw data may be compressed and stored as in the twelfth embodiment.

As described above, according to the present invention, after the first image is calculated, continuous images before and after the first image can be reconstructed with a very small calculation amount as compared to normal reconstruction. Therefore, a CT apparatus, which can reconstruct a large number of images continuously photographed by the helical scan optical at high speed, can be provided.

According to the present invention, since virtual view data are calculated not only by an interpolation but also by an extrapolation as needed, an image, which is less blurred in the Z axis direction, can be reconstructed.

Furthermore, according to the present invention, a large number of tomographic images can be reconstructed from a large amount of projection data acquired by a continuous fixed position scan or a helical scan within a short period of time, and the storage capacity of data necessary for reconstruction can be reduced.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, in each of the above-mentioned embodiments, each slice and projection image are present at an identical position. However, even when the positions of each slice and projection image are shifted from each other, the present invention can be practiced by modifying equations.

What is claimed is:

1. A computed tomography apparatus for performing a helical scan using a fan-shaped radiation beam, the apparatus comprising:

first means for calculating 360° virtual projection data at a first slice position by executing an estimation process of projection data in a range of 360°+a double fan angle acquired before and after the first slice position, and reconstructing a tomographic image at the first slice position from the virtual projection data;

second means for calculating a subtraction image between a tomographic image at a second slice position adjacent to the first slice position, and the tomographic image at the first slice position by reconstructing a difference between 360° virtual projection data necessary for reconstructing the tomographic image at the second slice position, and the 360° virtual projection data at the first slice position; and third means for calculating the tomographic image at the second slice position by synthesizing the subtraction image and the tomographic image at the first slice position.

2. An apparatus according to claim 1, in which said first means comprises means for calculating 360° virtual projection data at an arbitrary slice position from projection data at a slice position near the slice and reflection beam data of the projection data by an estimation process, wherein when the projection data and the reflection beam data used in the estimation process sandwich the slice, the virtual projection data are calculated by interpolation, and when the projection data and the reflection beam data used in the interpolation do not sandwich the slice, the virtual projection data are calculated by an extrapolation.

3. An apparatus according to claim 1, wherein said second means compresses and stores the subtraction image.

4. An apparatus according to claim 1, wherein said third means compresses and stores the subtraction image.

5. An apparatus according to claim 1, which performs a Rotate/Rotate type helical scan.

6. An apparatus according to claim 1, which performs a Stationary/Rotate type helical scan.

7. An apparatus according to claim 1, wherein said first means comprises:

means for obtaining, from each projection data, reflection beam data having a direction opposite to a direction of a beam associated with the projection data; and means for calculating the 360° virtual projection data at the first slice position by interpolating and extrapolating the projection data and the reflection beam data.

8. An apparatus according to claim 7, wherein said 360° virtual projection data calculating means comprises means for interpolating the projection data and the reflection beam data when the projection data and the reflection beam data sandwich the first slice position and means for extrapolating the projection data and the reflection beam data when the projection data and the reflection beam data do not sandwich the first slice position.

9. A computed tomography apparatus for performing a helical scan using a fan-shaped radiation beam, the apparatus comprising:

first means for calculating 360° virtual projection data at a first slice position by executing an estimation process of projection data in a range of 360°+a double fan angle acquired before and after the first slice position, and subjecting the 360° virtual projection data at the first slice position to a predetermined reconstruction processing to reconstruct a tomographic image at the first slice position; and second means for reconstructing a tomographic image at a second slice position adjacent to the first slice position by subjecting the tomographic image at the first slice position and a difference between 360° virtual projection data necessary for the predetermined reconstruction processing to reconstruct the tomographic image at the second slice position and the 360° virtual projection data at the first slice position to the predetermined reconstruction processing.

10. An apparatus according to claim 9, which performs a Stationary/Rotate type helical scan.

11. An apparatus according to claim 9, which performs a Rotate/Rotate type helical scan.

12. An apparatus according to claim 9, in which said first means comprises means for calculating 360° virtual projection data at an arbitrary slice position from projection data at a slice position near the slice and reflection beam data of the projection data by an estimation process, wherein when the projection data and the reflection beam data used in the estimation process sandwich the slice, the virtual projection data are calculated by interpolation, and when the projection data and the reflection beam data used in the interpolation do not sandwich the slice, the virtual projection data are calculated by an extrapolation.

13. An apparatus according to claim 9, wherein said first means comprises:

means for obtaining, from each projection data, reflection beam data having a direction opposite to a direction of a beam associated with the projection data; and means for calculating the 360° virtual projection data at the first slice position by interpolating and extrapolating the projection data and the reflection beam data.

14. An apparatus according to claim 13, wherein said 360° virtual projection data calculating means comprises means for interpolating the projection data and the reflection beam data when the projection data and the reflection beam data sandwich the first slice position and means for extrapolating the projection data and the reflection beam data when the projection data and the reflection beam data do not sandwich the first slice position.

15. A computed tomography apparatus for acquiring projection data by executing a helical scan using a fan-shaped radiation beam, and calculating 360° virtual projection data at an arbitrary slice position from a projection data group at a slice position near the slice by an estimation process, the apparatus comprising:

means for calculating a first reflection beam data group relating to positions before the slice position from the projection data group;

means for calculating a second reflection beam data group relating to positions after the slice position from the projection data group;

means for calculating a first virtual projection data group by interpolating a first projection data group relating to positions in a range of 180° before the slice position and the first reflection beam data group when the first projection data group relating to positions in a range of 180° before the slice position and the first reflection beam data group sandwich the slice position and by extrapolating the first projection data group relating to positions in a range of 180° before the slice position and the first reflection beam data group when the first projection data group relating to positions in a range of 180° before the slice position and the first reflection beam data group do not sandwich the slice position;

means for calculating a second virtual projection data group by interpolating a second projection data group relating to positions in a range of 180° after the slice position and the second reflection beam data group when the second projection data group relating to positions in a range of 180° after the slice position and the second reflection beam data group sandwich the slice position and by extrapolating the second projection data group relating to positions in a range of 180° after the slice position and the second reflection beam data group when the second projection data group relating to positions in a range of 180° after the slice position and the second reflection beam data group do not sandwich the slice position; and means for reconstructing an image at the slice position from the first and second virtual projection data groups.

16. A computed tomography apparatus for performing a helical scan using a fan-shaped radiation beam, the apparatus comprising:

storage means for compressing and storing projection data;

reconstruction means for reconstructing a first tomographic image at a first slice position using the data stored in said storage means; and means for calculating a subtraction image between a second tomographic image at a second slice position adjacent to the first slice position, and the first tomographic image by using difference data between a first data group necessary to, reconstruct the first tomographic image, and a second data group necessary to reconstruct the second tomographic image in said storage means.

17. A computed tomography apparatus for performing a helical scan using a fan-shaped radiation beam, the apparatus comprising:

reconstruction means for reconstructing a first tomographic image at a first slice position;

calculating means for calculating a subtraction image between a second tomographic image at a second slice position adjacent to the first slice position and the first tomographic image using difference data between a first data group necessary for said reconstruction means to calculate the first tomographic image, and a second data group necessary for said reconstruction means to calculate the second tomographic image; and storage means for compressing and storing the subtraction image.

18. An apparatus according to claim 17, which further comprises:

expansion means for reading out the subtraction image, and expanding the readout subtraction image; and means for calculating the second tomographic image by synthesizing the subtraction image obtained by said expansion means and the first tomographic image.

19. An apparatus according to claim 17, wherein said reconstruction means, said subtraction means, and said storage means are simultaneously operated in parallel with the scan operation of an object to be examined.

* * * * *

UNITED STATES PATENT AND TRADEMARK OFFICE
CERTIFICATE OF CORRECTION

PATENT NO. : 5,524,130
DATED : June 04, 1996
INVENTOR(S) : Akinami OHHASHI

It is certified that error appears in the above-indentified patent and that said Letters Patent is hereby corrected as shown below:

Claim 16, Column 59, Line 27, after "to", delete ",".

Signed and Sealed this

Third Day of December, 1996

Attest:

BRUCE LEHMAN

*Attesting Officer*         *Commissioner of Patents and Trademarks*